United States Patent [19]
Taichman et al.

[11] Patent Number: 5,733,541
[45] Date of Patent: Mar. 31, 1998

[54] HEMATOPOIETIC CELLS: COMPOSITIONS AND METHODS

[75] Inventors: Russell S. Taichman, Ann Arbor, Mich.; Stephen G. Emerson, Wayne, Pa.

[73] Assignee: The Regent of the University of Michigan, Ann Arbor, Mich.

[21] Appl. No.: 426,792

[22] Filed: Apr. 21, 1995

[51] Int. Cl.$^6$ .............................. A01N 63/02; C12N 5/00; C12N 5/06
[52] U.S. Cl. .................. 424/93.1; 424/93.7; 435/325; 435/347; 435/377; 435/373; 435/375
[58] Field of Search ................................. 435/325, 347, 435/355, 373, 375, 384, 385, 386, 240.1; 424/93.1, 93.7

[56] References Cited

U.S. PATENT DOCUMENTS

| | | | |
|---|---|---|---|
| 5,192,553 | 3/1993 | Boyse et al. | 424/529 |
| 5,605,822 | 2/1997 | Emerson et al. | 435/172.3 |

OTHER PUBLICATIONS

Lasky et al. Size and density characterization of human committed and multipotent hematopoietic progenitors. Exp. Hematol., vol. 13, pp. 680–684, 1985.

Taichman et al. Human osteoblasts are a constitutive source of G–CSF in the bone marrow. Blood, vol. 82, p. 234A, 35th annual meeting of the American Society of Hematology, St. Louis, Missouri, Dec. 1993.

Amsel and Dell, "Bone Formation by Hemopoietic Tissue: Separation of Preosteoblast From Hemopoietic Stem Cell Function in the Rat," *Blood*, 39(2):267–273, Feb. 1972.

Benayahu et al., "Bone Formation by Marrow Osteogenic Cells (MBA–15) Is Not Accompanied by Osteoclastogenesis and Generation of Hematopoietic Supportive Microenvironment," *Journal of Bone and Mineral Research*, 9(7):1107–1114, 1994.

Benayahu et al., "Subpopulations of Marrow Stromal Cells Share a Variety of Osteoblastic Markers," *Calcif. Tissue Int.*, 49:202–207, 1991.

Benayahu et al., "Hemopoietic Functions of Marrow–Derived Osteogenic Cells," *Calcif. Tissue Int.*, 51:195–201, 1992.

Berardi et al., "Functional Isolation and Characterization of Human Hematopoietic Stem Cells," *Science*, 267:104–108, Jan., 1995.

Birch et al., "PCR Detection of Cytokines in Normal Human and Pagetic Osteoblast–like Cells," *Journal of Bone and Mineral Research*, 8(10):1155–1162, 1993.

Chaudhary et al., "Production of Various Cytokines by Normal Human Osteoblast–Like Cells in Response to Interleukin–1β and Tumor Necrosis Factor–α: Lack of Regulation by 17β–Estradiol," *Endocrinology*, 130(5):2528–2534, 1992.

Chaudhary and Avioli, "Dexamethasone Regulates Il–1β and TNF–α–Induced Interleukin–8 Production in Human Bone Marrow Stromal and Osteoblast–Like Cells," *Calcif. Tissue Int.*, 55:16–20, 1994.

Deldar et al., "Bone Lining Cells and Hematopoiesis: An Electron Microscopic Study of Canine Bone Marrow," *The Anatomical Record*, 213:187–201, 1985.

Dodds et al., "Expression of mRNA for IL1β, IL6 and TGFβ1 in Developing Human Bone and Cartilage," *J. of Histochemistry and Cytochemistry*, 42(6):733–744, 1994.

Elford et al., "Murine Osteoblastlike Cells and the Osteogenic Cell MC3T3–E1 Release a Macrophage Colony–Stimulating Activity in Culture," *Calcif. Tissue Int.*, 41:151–156, 1987.

Elias et al., "Cytokine and Hormonal Stimulation of Human Osteosarcoma Interleukin–11 Production," *Endocrinology*, 136(2):489–498, 1995.

Felix et al., "Production of Granulocyte–Macrophage (GM–CSF) and Granulocyte Colony–Stimulating Factor (G–CSF) by Rat Clonal Osteoblastic Cell Population CRP 10/30 and the Immortalized Cell Line IRC10/30–myc1 Stimulated by Tumor Necrosis Factor α," *Endocrinology*, 128(2):661–667, 1991.

Felix et al., "Production of Hemopoietic Growth Factors by Bone Tissue and Bone Cells in Culture," *Journal of Bone and Mineral Research*, 3(1):27–36, 1988.

Feyen et al., "Interleukin–6 Is Produced by Bone and Modulated by Parathyroid Hormone," *Journal of Bone and Mineral Research*, 4(4):633–638, 1989.

Gowen et al., Production of Tumor Necrosis Factor by Human Osteoblasts is Modulated by Other Cytokines, but not by Osteotropic Hormones," *Endocrinology*, 126(2):1250–1255, 1990.

Horowitz et al., "Parathyroid Hormone and Lipopolysaccharide Induce Murine Osteoblast–like Cells to Secrete a Cytokine Indistinguishable from Granulocyte–Macrophage Colony–Stimulating Factor," *J. Clin. Invest.*, 83:149–157, Jan. 1989.

Horowitz et al., "Osteotropic Agents Induce the Differential Secretion of Granulocyte–Macrophage Colony–Stimulating Factor by the Osteoblast Cell Line MC3T3–E1, *Journal of Bone and Mineral Research*, 4(6):911–921, 1989.

Horowitz et al., "Functional and Molecular Changes in Colony Stimulating Factor Secretion by Osteoblasts," *Connective Tissue Research*, 20:159–168, 1989.

Ishimi et al., "IL–6 is Produced by Osteoblasts and Induces Bone Resorption," *The Journal of Immunology*, 145(10):3297–3303, Nov. 1990.

(List continued on next page.)

Primary Examiner—Jasemine C. Chambers
Assistant Examiner—Deborah J. R. Clark
Attorney, Agent, or Firm—Arnold, White & Durkee

[57] ABSTRACT

Processes, compositions and uses of hematopoietic cells are disclosed. Hematopoietic cells are cells which can differentiate into mature blood cells when co-cultured with osteoblasts. Specifically, a process for propagating and maintaining the immature morphology of a hematopoietic cell by co-culturing with osteoblasts is disclosed. The osteoblasts provide cytokines and/or a microenvironment which propagates and maintains the immature morphology of a hematopoietic cell. Hematopoietic cells are useful in the treatment of certain blood related disorders and are useful for treatment of patients in need of hematopoietic cells.

41 Claims, No Drawings

OTHER PUBLICATIONS

Joos et al., "Mesenchymal Cells and Osteoblasts: Cytokines Promote a Shuttle Mechanism of Osteogenesis Versus Hematopoieses," *Calcif. Tissue Int.*, 44(Suppl.):S–41, 1989.

Keeting et al., "Evidence for Interleukin–1β Production by Cultured Normal Human Osteoblast–like Cells," *Journal of Bone and Mineral Research*, 6(8):827–833, 1991.

Lacey et al., "Interleukin 4 Enhances Osteoblast Macrophage Colony–Stimulating Factor, but Not Interleukin 5, Production," *Calcif. Tissue Int.*, 55:21–28, 1994.

Lacey et al., "IL–1–Induced Murine Osteoblast IL–6 Production is Mediated by the Type 1 IL–1 Receptor and Is Increased by 1,25 Dihydroxyvitamin $D_3$," *J. Clin. Invest.*, 91:1731–1742, Apr. 1993.

Linkhart et al., "Interleukin–6 Messenger RNA Expression and Interleukin–6 Protein Secretion in Cells Isolated from Normal Human Bone: Regulation by interleukin–1," *Journal of Bone and Mineral Research*, 6(12):1285–1294, 1991.

Long et al., "Expression of Human Bone–Related Proteins in the Hematopoietic Microenvironment," *J. Clin. Invest.*, 86:1387–1395, Nov. 1990.

Long et al., "Regulation of Human Bone Marrow–Derived Osteoprogenitor Cells by Osteogenic Growth Factors," *J. Clin. Invest.*, 95:881–887, Feb. 1995.

Löwik et al., "Parathyroid Hormone (PTH) and PTH–Like Protein (PLP) Stimulate Interleukin–6 Production by Osteogenic Cells: A Possible Role of Interleukin–6 in Osteoclastogenesis," *Biochemical and Biophysical Research Communications*, 162(3):1546–1552, Aug. 1989.

Marie et al., "In Vitro Production of Cytokines by Bone Surface–Derived Osteoblastic Cells in Normal and Osteoporotic Postmenopausal Women: Relationship with Cell Proliferation," *Journal of Clinical Endocrinology and Metabolism*, 77(3):824–830, 1993.

Marusic et al., "Production of Leukemia Inhibitory Factor mRNA and Protein by Malignant and Immortalized Bone Cells," *Journal of Bone and Mineral Research*, 8(5):617–624, 1993.

Meck and Mel, "A Test of Osteoblasts for Hematopoietic Competence," *Hemat.*, 1:159–164, 1973.

Meck et al., "Hematopoiesis Versus Osteogenesis in Ectopic Bone Marrow Transplants," *Blood*, 45(5):661–669, Nov. 1973.

Oursler et al., "Modulation of Transforming Growth Factor–β Production in Normal Human Osteoblast–Like Cells by 17β–Estradiol and Parathyroid Hormone," *Endocrinology*, 129(6):3313–3320, 1991.

Ralston, "Analysis of Gene Expression in Human Bone Biopsies by Polymerase Chain Reaction: Evidence for Enhanced Cytokine Expression in Postmenopausal Osteoporosis," *Journal of Bone and Mineral Research*, 9(6):883–890, 1994.

Sakagami et al., "Stimulation of Interleukin–6 Production by Either Calcitonin Gene–Related Peptide or Parathyroid Hormone in Two Phenotypically Distinct Bone Marrow–Derived Murine Stromal Cell Lines," *Journal of Bone and Mineral Research*, 8(7):811–816, 1993.

Sato et al., "Tumor Necrosis factor Type α (Cachectin) Stimulates Mouse Osteoblast–Like Cells (MC3T3–E1) to Produce Macrophage–Colony Stimulating Activity and Prostaglandin $E_2$," *Biochemical and Biophysical Research Communications*, 145(1):323–329, May 1987.

Taichman and Emerson, "Maintenance and Expansion of Human LTC–IC and Progenitor Cells by Human Osteoblasts In Vivo," *Abstract*, Annual Meeting of the American Society of Hematology, Dec. 5, 1994.

Taichman and Emerson, "Human Osteoblasts Support Hematopoiesis through the Production of Granulocyte Colony–stimulating Factor," *J. Exp. Med.*, 179:1677–1682, May, 1994.

Tavassoli, "Hemopoiesis in Ectopically Implanted Bone Marrow," *Kroc. Found Ser.*, 18:31–54, 1984.

Vaughan, "Osteogenesis and Haematopoiesis," *The Lancet*, II(8238):133–136, Jul., 1981.

Vlasselaer et al., "Interleukin–10 Stimulates Hematopoiesis in Murine Osteogenic Stroma," *Clinical Orthopaedics and Related Research*, 313:103–114, Apr. 1995.

Vlasselaer et al., "Interleukin–10 Inhibits the Osteogenic Activity of Mouse Bone Marrow," *Blood*, 82(8):2361–2370, Oct., 1993.

Vlasselaer et al., "Interleukin 10 Inhibits Transforming Growth Factor–β (TGF–β) Synthesis Required for Osteogenic Commitment of Mouse Bone Marrow Cells," *The Journal of Cell Biology*, 124(4):569–577, Feb. 1994.

Wallach et al., "Cytokines and Bone Metabolism," *Calcif. Tissue Int.*, 53:293–296, 1993.

Weir et al., "Macrophage Colony–Stimulating Factor Release and Receptor Expression in Bone Cells," *Journal of Bone and Mineral Research*, 8(12):1507–1518, 1993.

Weir et al., "Osteoblast–like cells secrete granulocyte–macrophage colony–stimulating factor in response to parathyroid hormone and lippopolysaccharide," *Endocrinology*, 124:899–904, 1989.

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

CAGTAGTGAC TCATCCGA                                                      18

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TTCCTTCCTC CTCTTCCTCC T                                                  21

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GGCCCACTCC ATGAAGGCTG CATG                                               24

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GTCAGTGATA GAGGGTGGCC CCCC                                               24

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GGATCCTTGA AGACAAGCTG GGTTAACTGC TCTAAC                                  36

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AAGCTTGATA TGGATTGGAT GTCGCGTGGG TGC 33

( 2 ) INFORMATION FOR SEQ ID NO:7:

( i ) SEQUENCE CHARACTERISTICS:
  ( A ) LENGTH: 33 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:7:

GGATCCTCCT TCTCCACAAG CGCCTTCGGT CCA 33

( 2 ) INFORMATION FOR SEQ ID NO:8:

( i ) SEQUENCE CHARACTERISTICS:
  ( A ) LENGTH: 34 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:8:

AAGCTTGTTC CTCACTACTC TCAAATCTGT TCTG 34

( 2 ) INFORMATION FOR SEQ ID NO:9:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:9:

TTCTCTTGGC TGTTACTGCC AGGA 24

( 2 ) INFORMATION FOR SEQ ID NO:10:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:10:

GTCTTCCTTG ATGGTCTCCA CACTC 25

( 2 ) INFORMATION FOR SEQ ID NO:11:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:11:

CACAGTGCAC TCTGGACAGT GCAGGAA 27

( 2 ) INFORMATION FOR SEQ ID NO:12:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:12:

CATTCCCAGT TCTTCCATCT GCTGCCAGAT           30

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GAGCATGTGA ATGCCATCCA GGAG           24

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CTCCTGGACT GGCTCCCAGC AGTCAAA           27

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GGCAGCGAGG TAGTGAAGAG           20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GATGTGGTCA GCCAACTCGT           20

( 2 ) INFORMATION FOR SEQ ID NO:17:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:17:

ACCACTGCCG CACAACTCCG GTGAC 25

(2) INFORMATION FOR SEQ ID NO:18:

(i) SEQUENCE CHARACTERISTICS:
  (A) LENGTH: 25 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:18:

ATCTATGACA AGTTCAAGCA GAGTA 25

(2) INFORMATION FOR SEQ ID NO:19:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:19:

GCAGTAAGAT CATCTTCTCG AACC 24

(2) INFORMATION FOR SEQ ID NO:20:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:20:

CAGATAGATG GGCTCATACC A 21

(2) INFORMATION FOR SEQ ID NO:21:

(i) SEQUENCE CHARACTERISTICS:
  (A) LENGTH: 23 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:21:

TGTTGGCCTC ACACCTTCAG CTG 23

(2) INFORMATION FOR SEQ ID NO:22:

(i) SEQUENCE CHARACTERISTICS:
  (A) LENGTH: 25 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:22:

```
ATCTGTGTGG GTGGATAGCT GGTCT                                          25
```

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
GAAGGGATCT GCAGGAATCG TGTG                                           24
```

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
GCCCTTGTAA GACCTGGCTG TCTC                                           24
```

( 2 ) INFORMATION FOR SEQ ID NO:25:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

```
CAGCCATGTA CGTTGCTA                                                  18
```

( 2 ) INFORMATION FOR SEQ ID NO:26:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

```
GGATCCAATA CGACTCACTA TAGGCTCCGA GGAATTACAG TGCGTG                   46
```

( 2 ) INFORMATION FOR SEQ ID NO:27:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

```
ATCCAGCTAC GAATCTCCGA C                                              21
```

( 2 ) INFORMATION FOR SEQ ID NO:28:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:28:

GTGCGTCCTG TCCATGTCTA A                   21

HEMATOPOIETIC CELLS: COMPOSITIONS AND METHODS

The United States government may own certain rights in the present invention pursuant to grant 5 R29 DE11283.

FIELD OF THE INVENTION

This invention relates generally to processes for propagating hematopoietic cells in the presence of osteoblasts and the compositions thereof. The invention relates as well to processes for maintaining the immature morphology of a hematopoietic cell. The hematopoietic cells of the present invention are capable of differentiating into mature blood cells.

BACKGROUND OF THE INVENTION

Hematopoietic stem cell differentiation occurs in direct proximity to osteoblasts within the bone marrow cavity. In adults the formed elements of the blood are produced in the bone marrow. The development of the bone marrow cavity is an coordinated process in which blood precursors migrate and colonize spaces carved out of embryonic bone and cartilage. Thus, an intimate physical association between bone cells and blood cells is established early in life.

It has long been appreciated that stromal cells in the marrow provide the structural scaffolding for hematopoiesis (Mayani et al., 1992). More recently, evidence has been acquired to indicate that stromal cells also produce several factors critical to the development of blood cells. In this context much work has been carded out using human and animal model systems of marrow reticular fibroblasts, macrophages, adipocytes and endothelial cells. In brief, these studies have demonstrated that: i) direct stromal cell-to-blood cell contact, ii) stromal cell production of the extracellular bone marrow matrix and iii) cytokine synthesis by stromal cells are all relevant to the formation of various blood cells (reviewed in Metcalf, 1988; Dexter et al., 1990; and Dexter et al., 1990). Although osteoblasts are also part of the stromal support system in the marrow, little is known about their relationship to hematopoietic stem cells.

During the early intrauterine period, blood formation takes place within the yolk sac, the liver and the spleen. By the sixteenth week of gestation the bone marrow begins to produce blood and from that point on hematopoiesis occurs almost exclusively within bone. Why the bone marrow becomes the exclusive site of hematopoiesis in adult primates and not in other mammals is not known.

The earliest attempts to understand the relationship between bone and hematopoiesis focused on the idea that the skeleton merely "protected" the hematopoietic organ (Trentin et al., 1989). This explanation is not satisfying in light of evidence that: i) During bone marrow transplantation, donor blood stem cells circulate to all body organs but "home" specifically to the bone marrow. When marrow cells lodge in other tissues they may undergo several rounds of division but hematopoiesis is not sustained in these sites (Trentin et al., 1989 and Tavassoli et al., 1993); ii) Host survival after marrow ablation occurs only if stem cells successfully engraft in the bone marrow; iii) Induction of ectopic bone formation in extraskeletal sites results in the formation of a functional hematopoietic marrow outside the protective confines of the skeleton (Reddi et al., 1981 and Urist et al., 1983).

Primitive hematopoietic stem cells are closely associated with the endosteal bone surfaces rather than randomly distributed throughout the marrow cavity. It is conceivable that integrin-like interactions produced by endosteal cells serve to position blood forming elements to their microenvironment. For example; i) integrin-ligand cell-to-cell interactions ii) growth factors synthesized in membrane bound forms (i.e. IL-1α and M-CSF, c-kit ligand) (Toksoz et al., 1992; Kurt-Jones et al., 1985; and Stein et al., 1990) iii) or soluble cytokines that localize to cell or extracellular matrix surfaces by way of intermediary glycosaminoglycans (IL-3, GM-CSF, TGF-$\beta_1$) have received some support in the literature (Gordon et al., 1987; Gordon et al., 1993; Roberts et al., 1988; Gordon et al., 1988; and Fava et al., 1987. In this context, direct contact with the stromal cells is necessary for stem cell maintenance in long term bone marrow culture (LTBMC). If the two tissues are separated in vitro, a precipitous decline in stem cell populations ensues (Dexter et al., 1987). Moreover, in cultures, discrete cellular elements of the stroma seem to support specific hematopoietic lineages. For instance, clones of lymphocytes, granulocytes as well as other hematopoietic cell populations occupy discrete "niches" in these cultures. This may be due to variations in the nature of the stromal cells in different locals with in the culture (Dexter et al., 1988; Dexter et al., 1987; and Trentin 1989).

Another mechanism to explain how stromal cells interact with hematopoietic cells is through the production of cytokine/growth factor(s) by endosteal cells. These molecules may influence the position and functions of stem and/or progenitor cells. Indeed, there is substantial evidence that cytokines derived from marrow stromal cells can support hematopoiesis (Dexter et al., 1990; Tavassoli et al., 1993; Brühl et al., 1988; Fibbe et al., 1988; Kincade et al., 1987; Citable et al., 1991; Heard et al., 1986; Johnson et at., 1986; Kittler et at., 1992; and Cuba et al., 1992). At present the list includes G-CSF, M-CSF, GM-CSF, c-kit ligand, IL-1, IL-5, IL-6, TNF-α, and TNF-β. Cytokines produced by stromal cells have been studied in LTBMC systems. In these cultures, limited in vitro hematopoiesis can be maintained for several months; by contrast, growth in soft agar can only be maintained for much shorter (days) periods of time unless exogenous growth factors are added to the cultures (Dexter et al., 1987). The major difference between these culture techniques is the presence of stromal cells in LTBMC system. Significantly, stroma from other tissues including spleen and liver do not support hematopoiesis in vitro (Mayani et al., 1992). Stem cells grown in the absence of stromal cells die (Johnson et al., 1986).

Even hematopoietic stem cell cultures maintained with stromal cells have a limited capacity for self-renewal, however (Dexter et al., 1974; Eastman et al., 1984; Eaves et al., 1991; and Caldwell et al., 1994). Despite the presence of stromal cells, LTBMC do not produce significant numbers of either non-adherent hematopoietic precursors or progenitor cells beyond several weeks without recharging the cultures with fresh marrow (Eastman et al., 1984; Eaves, Cashman et al., 1991; Caldwell et al., 1994; Eaves, Sutherland et al., 1991). In addition, not all hematopoietic lineages are equally represented relative to in vivo marrow production. The ultimate loss of stem cell populations probably reflects either a failure of stem cell renewal or lineage commitment of the progenitor cells (Srour et al., 1993; Gamer et al., 1990; and Zipori et al., 1992). The cause of LTBMC's failure to support stem cells is not known. Several recent reports suggest that stromal cell dysfunction is at the root of the problem. This dysfunction could either result from impaired or deficient cytokine production due to a primary defect in the stromal cells themselves, or arises secondarily to inadequate culture conditions (Caldwell et al., 1994; Schwartz, Emerson et al., 1991; Dexter et al., 1977; Schwartz, Polson et al., 1991; and Nicola et al., 1989). For example, evidence for a defect in stromal cell cytokine production comes from investigations where the normal source of G-CSF is explored. This factor is required for the proliferation and terminal differentiation of myeloid progenitor cells (Negata et al., 1990). In addition, G-CSF enhances granulocyte functions including phagocytosis, chemotaxis, and antibody-dependent cell-mediated cytotoxicity (Negata et al., 1990). Constitutive production of G-CSF in human LTBMC cannot be demonstrated despite evidence that these culture support limited granulopoiesis (Kittler et al., 1992 and Kittler et al., 1993). We know that stimulated stroma can produce G-CSF because G-CSF synthesis has been characterized in LTBMC under conditions that simulate inflammation including IL-1α, TNF-α and lipopolysaccharide stimulation (Fibbe et al., 1988). The source of G-CSF in the absence of inflammatory simulators, however, is unclear. Additional evidence for defective cytokine production by stromal cells comes from experiments where progenitor cell maintenance is significantly enhanced by stromal fibroblasts that are genetically engineered to constitutively produce cytokines at in vivo levels (Zipori et at., 1988).

Alternatively, recent investigations in rapid medium exchange culture techniques suggest that stromal dysfunction may result from culture undernourishment. Substantial improvement in hematopoietic cell proliferation and differentiation occurs simply by elevating the culture perfusion rate to in vivo levels. Nevertheless, even with genetically engineered fibroblasts and rapid medium exchange techniques, these systems do not fully reproduce the complexity of in vivo hematopoiesis (Calwell et al., 1994; Dexter et al., 1974; Zipori et al., 1988; Dexter et at., 1974; Dexter et al., 1977; and Whitlock et al., 1982). Whether the shortcoming in LTBMCs are first due to stromal dysfunction or inadequate culture conditions, or both is still not known. What is known however is that some factor or factors which are essential for normal hematopoiesis that are present at endosteal bone surfaces are missing from in vitro LTBMCs.

Long-term in vitro bone marrow culture systems which support either limited myelopoiesis (Dexter cultures) or limited lymphopoiesis (Whitlock-Witte cultures) are dependent on the formation of stromal cell layers derived from bone marrow ( Dexter et al., 1990, Dexter et al., 1974; Dexter et al., 1977; Whitlock et al., 1982; and Quesenberry, 1989). The apparent basis for these observations is the production of hematopoietic growth factors, albeit at low or subliminal levels, by the stromal cell layer (Tavassoli et al., 1993; Kittler et al., 1992; and Guba et al., 1992. Osteoblast-like cells have been observed within these stromal layers and share several phenotypic characteristics with stromal cell lines (Benayahu et al., 1992; Benayahu et al., 1991; Mathieu et al., 1992; Theis et al., 1992; and Dorheim et al., 1993. For example, the murine bone marrow stromal cell lines BMS2 and ±+2.4, share a number of osteoblast markers including high alkaline phosphatase, collagen (I) and bone sialoprotein-II (Dorheim et cl., 1993). In addition, mRNA for osteocalcin, a osteoblast specific protein also was detected in BMS2 cells (Dorheim et al., 1993).

In a series experiments using several stromal cell lines, Benayhu et al found that all cell types examined (MBA-1: fibroblasts, MBA-2 endothelial-like, MBA-13 fibroendothelial, 13F1.1 cloned preadipocyte, MBA-15 osteoblastic) possess some osteoblastic features, but differed in the degree of expression (Benayahu et al., 1992 and Benayahu et al., 1991). Thies et al found that recombinant human bone morphogenic protein-2 induces osteoblastic differentiation in the W-20-17 murine stromal cell line (Theis et at., 1992). Finally, ectopic marrow transplantation experiments clearly demonstrate that new formed bone marrow stroma and bone are derived from the donor, while blood cells are of host origin (Reddi et al., 1981; Urist et al., 1993; and Shinner et al., 1993).

Further evidence of a functional link between hematopoietic progenitor cells and osteoblasts is provided by observations that osteoprogenitor cells originate from the bone marrow. Several investigators have shown that both primary and transformed bone marrow stromal cells can acquire the osteoblast phenotype as bone formation is observed in vivo after implantation of these cells into diffusion chambers (Friedenstein et al., 1970; Ashton et al., 1994; and Grigoriadis et al., 1988). In vitro incubation of non-adherent low-density bone marrow cells in serum free conditions can also develop into osteoblast-like cells which can mineralize their extracellular matrix (Long et al., 1990 and Campell et at., 1987.

Recently Huang and Terstappen isolated a population of stem cells from human fetal bone marrow that were capable of extensive self renewal and differentiation into a variety of hematopoietic lineages (Huange et at., 1992). Three color immunofluorescence techniques were used to isolate several subsets of $CD34^+$ cells. Although most $CD34^+$ cells were already committed to their individual blood cell lineages, singly isolated $CD34^+$, $HLA-DR^-$, $CD38^-$ cells could differentiate into all hematopoietic and stromal lineages including osteoblasts (Huange et al., 1992). The early development of a stromal microenvironment from stem cells was subsequently found capable of establishing conditions favorable to induce the common $CD34^+$, $HLA-DR^-$, $CD38^-$ stem cells to differentiate into hematopoietic stem cells (Huange et al., 1992). Together these studies provide definitive proof of a osteogenic commitment with in the stromal cell population.

Perhaps the failure of LTBMCs is due to an insufficient presence of osteoblasts. Perhaps osteoblasts keep stem cells viable or out of replicative cell cycles. Evidence for such an hypothesis has recently been demonstrated for stromal cells Kincaide et al., 1991). Unfortunately, the inhibitory mechanisms that regulate the cell cycle status of primitive hematopoietic cells, and in particular osteoblasts role in these functions are poorly understood. It is possible that both positive and negative proliferative signals are derived from one cell. In this context, the positive signals produced by osteoblasts may be sufficient to assure the survival of progenitor cells, but insufficient in either quantity or quality for hematopoietic stem cells to overcome the negative regulatory signals either produced locally or by osteoblasts themselves to enter into replicative cycles. In fact, most osteoblasts basally produce $TGF-\beta_1$ and to a varying degrees $TNF-\alpha$ and $\beta$ (Robey et al., 1987 and Gowen et al., 1990). Both $TNF-\alpha$, $TNF-\beta$ and $TGF-\beta_1$ efficiently inhibit myeloid cell development (Zipori et al., 1986 and Broxmeyer et al., 1986) and $TGF-\beta_1$ restricts lymphocyte proliferation (lee et al., 1986). In addition, $TGF-\beta_1$ is a potent inhibitor of several proliferative activators for myelocytes and lymphoblasts including IL-3, G-CSF, GM-CSF (Masatsugu et al., 1987).

During the past decade, primary mouse osteoblasts have been shown to produce G-CSF (Felix et al., 1988), M-CSF (Elford et al., 1987 and Horowitz, Einhorn et al., 1989), GM-CSF (Elford et al., 1987 and Horowitz, Einhorn et al., 1989), IL-1 (Hanazawa et al., 1987), and IL-6 (Ishimi et al., 1990 and Feyen et al., 1989), while transformed mouse osteoblasts were reported to produce G-CSF (Horowitz, Coleman, Tyaby et al., 1989), M-CSF (Benayahu et al., 1992; Elford et al., 1987; and Horowitz, Einhorn et al., 1989), GM-CSF (Benayahu et al., 1992 and Hanazawa et al., 1985), IL-1 (Hanaza et al., 1987) and IL-6 (Benyayahu et al., 1992 and Ishimi et al., 1990). Where IL-1, TNF and LPS stimulated the production of several of these cytokines in primary culture, unstimulated constitutive production by murine osteoblasts has only been observed for M-CSF and IL-6 (Elford et al., 1987 and Hanazawa et al., 1987). The rat ROS 17/2.8 cell line, an osteoblast-like osteosarcoma cell line, constitutively produces GM-CSF (Weir et al., 1989).

Human osteoblasts have been less well characterized in terms of their production of cytokines which are relevant to blood development. While it is well known that human osteoblasts produce insulin and transforming growth factors [reviewed in Hauschka et al., 1989 and Robey et al., 1987], primary human osteoblasts have only been reported to produce IL-1β (Keeting et al., 1991) and TNF-α (Gowen et al., 1990) when stimulated with TNF-α and IL-1β, respectively. The human osteosarcoma cell line SaOS-2 constitutively makes IL-6 which can be stimulated with either PTH or 1,25 (OH)$_2$ dihydroxyvitamin D$_3$ (Feyen a al., 1989). At present however, it is not known which of the colony stimulating factors human osteoblasts can produce either under basal or stimulated conditions.

It is important to keep in mind that the majority of this fundamental work has been accomplished using bioassays for cytokine detection. These assays are not necessarily specific, and as a rule, leave much to be desired. The inherent limitation of such an approach is that the potential presence of cytokine inhibitors, synergism between suboptimal cytokine concentrations and contributions from as yet unidentified cytokines are not addressed. Also, most cell lines utilized in the bioassays respond to more than one growth factor. In addition, few of the investigations detected the cytokine-like activity in resting cultures (Table 1). Most importantly however, few if any of these investigations were performed using normal human tissues.

Osteoblasts are members of the hematopoietic stromal cell system responsible for blood development and providing the structural scaffolding for hematopoietic stem cells (Mayani et al., 1992; Benayahu et al., 1991; Mathieu et al., 1992; Theis et al., 1992; and Dorheim et al., 1993).

Because osteoblasts are a major source of the colony stimulating cytokines in bone marrow, the regulation of osteoblast-elaborated cytokines and the functional consequences of alterations in osteoblast metabolism are relevant to several clinical settings including: response to marrow injury as in osteomyelitis and/or infections in surrounding tissues such as in periodontal infections, bone marrow failure syndromes such as aplastic anemia and cyclic neutropenia as the result of primary or secondary defects in osteoblast function, and finally, bone marrow transplantation into patients for therapeutic treatments.

SUMMARY OF THE INVENTION

In one aspect, the present invention provides a process for propagating a hematopoietic cell. The process comprises the steps of obtaining an enriched population of hematopoietic cells and co-culturing the enriched population of hematopoietic cells in the presence of osteoblast cells. The enriched population of hematopoietic cells are prepared from a population of mammalian cells that include hematopoietic cells.

In a preferred embodiment, human hematopoietic cells are the subject of the present invention. In a preferred embodiment, hematopoietic cell are enriched from human bone marrow cells, umbilical cord cells, liver cells, spleen cells, or peripheral blood stem cells.

Hematopoietic cells can also be purified from a population of mammalian cells that include hematopoietic cells by stimulating the growth of cells that have already begun to differentiate into more mature blood cells with a cytokine and by exposing the cells that have already begun to differentiate into more mature blood cells with an antimetabolite that kills these cells.

TABLE 1

REVIEW OF OSTEOBLAST CYTOKINE PRODUCTION

| Cytokine | Cell | Assay | Blocking Antibody | Basal Production | STIMULATING AGENT | | | | | | | Author |
|---|---|---|---|---|---|---|---|---|---|---|---|---|
| | | | | | D3 | PTH | IL1 a | IL1 b | TNF a | TNF b | LPS | CSF GM / GM | |
| IL-1 | MOB | b | | − | | | | | | | ↑ | | |
| IL-1 | MC3T3E1 | b | | + | | | | | | | | | 67 |
| IL-1b | HOB + (sv40) | bn | + | − | | − | | ↑ | ↑ | | | | 71 |
| TNF-a | HOB | b | + | − | − | − | ↑ | | | | ↑ | ↑ | 74 |
| IL-6 | HOB | nr | + | − | − | | | ↑ | | | | | 58 |
| IL-6 | MOB | bn | | − | − | − | ↑ | ↑ | ↑ | | ↑ | | 76,77 |
| IL-6 | MOB | b | + | + | ↑ | | | | | | | | 68 |
| IL-6 | SAOS-2 | b | + | + | ↑ | ↑ | | | | | | | 69 |
| IL-6 | MC3T3E1 | bn | | − | − | ↑ | ↑ | ↑ | ↑ | | ↑ | | 68 |
| IL-6 | MBA15 | b | | + | | | | | | | ↑ | | 44 |
| G-CSF | MOB | b | | − | | | − | | | | ↑ | | 63 |
| G-CSF | ctROB | b | | − | | − | − | | ↑ | | | | 110 |
| GM-CSF | MOB | b | | − | ↑ | ↑ | | | | | ↑ | | 64 |
| GM-CSF | MOB | b | + | − | | | | | | | ↑ | | 63 |
| GM-CSF | MC3T3E1 | bn | | − | − | ↑ | ↑ | | | | ↑ | | 70 |
| GM-CSF | MBA15 | b | + | + | | | | | | | ↑ | | 44 |
| GM-CSF | ROS17/2.8 | b | | + | | ↑ | | | | | ↑ | | 72 |
| M-CSF | MOB | b | | + | ↑ | − | ↑ | | | | | | 65 |
| M-CSF | MOB | bn | | − | | | | | | | ↑ | | 66 |
| M-CSF | MC3T3E1 | b | | + | ↑ | − | ↑ | | | | | | 65 |
| M-CSF | MC3T3E1 | bn | | + | | | | | | | ↓ | | 66 |
| M-CSF | MBA15 | b | | + | | | | | | | ↑ | | 44 |

The enriched population of hematopoietic cells can be prepared by exposing bone marrow cells to a hematopoietic cell antibody immunoreactive with a hematopoietic cell antigen and removing bone marrow cells which do not immunoreact with the hematopoietic cell antibody. Hematopoietic cells can be further enriched by equilibrium-density centrifugation of bone marrow cells. Equilibrium-density centrifugation of bone marrow cells provides a population of cells enriched in hematopoietic cells with a density of between about 1.010 and about 1.090 gm/cm$^3$, preferably between 1.040 and 1.080 gm/cm$^3$. The population of hematopoietic cells can be further enriched by removal of adherent cells (typically stromal cells), when the mammalian cells used are bone marrow cells, by exposing bone marrow cells to an adherent surface, typically tissue culture plastic or glass.

Antibodies used to enrich the population of hematopoietic cells include any antibody immunoreactive with a hematopoietic cell. Hematopoietic cell antibodies contemplated by the present invention include anti-CD34, anti-HLA-DR, and anti-Thy-1. In another aspect, a second antibody immunoreactive with a hematopoietic cell antibody can be used to enrich the population of hematopoietic cells. In one embodiment, antibodies are conjugated to a solid substrate including tissue culture dish, agarose, polyacrylamide, and magnetic particles.

Hematopoietic cells are propagated by co-culturing the hematopoietic cells in the presence of osteoblasts. In one embodiment, the hematopoietic cells are co-cultured with a confluent or a non-confluent culture of osteoblasts. The osteoblasts can be primary cultures derived from animals or humans. Alternatively, the osteoblasts are immortal cell lines known to those skilled in the art. The hematopoietic cells of the present invention can be co-cultured with osteoblasts for between about 1 week and about 8 weeks. Preferably, the hematopoietic cells are co-cultured with the osteoblasts for between about 2 weeks and about 6 weeks. Even more preferably, the hematopoietic cells are co-cultured with the osteoblasts for between about 2 weeks and about 4 weeks.

The osteoblast culture produces a cytokine or cytokines that stimulate the propagation of hematopoietic cells. Alternatively, the osteoblasts produces a cytokine and/or provides a microenvironment that promotes the propagation of hematopoietic cells. Preferably, the cytokine is granulocyte colony stimulating factor, granulocyte macrophage colony stimulating factor or stem cell factor.

Yet another aspect of the present invention provides a hematopoietic cell prepared by co-culturing an enriched population of hematopoietic cells in the presence of osteoblasts. The hematopoietic cell that is provided by co-culturing have a morphology that is CD34$^+$, and has a density of between about 1.010 gm/cm$^3$ and about 1.09 gm/cm$^3$. The hematopoietic cell can also be HLA-DR$^+$, Thy-1$^+$, and Lin$^-$. The hematopoietic cell of the present invention is capable of differentiating into a blood cell including erythrocyte, platelet, monocyte, neutrophil, basophil, eosinophil, lymphocyte, or a mast cell.

The hematopoietic cell of the present invention can be separated from the osteoblasts which are co-cultured with the hematopoietic cell and collected. The hematopoietic cells can be separated from the osteoblasts by antibody purification, equilibrium-density centrifugation, exposure to an adherent surface as described herein. Alternatively, the hematopoietic cells can be separated and collected from the osteoblasts by exposing the co-culture (hematopoietic cells in co-culture with osteoblasts) to an antimetabolite that selectively kills osteoblasts.

In yet another embodiment, the hematopoietic cell propagated by the methods disclosed herein can be infused into a human in need of hematopoietic cells. The hematopoietic cells are infused into the human by injecting the hematopoietic cells directly into the bloodstream of the human. Alternatively, the hematopoietic cells can be introduced into the human by directly introducing the hematopoietic cells into the marrow cavity of a bone.

In another aspect, the present invention provides a process for maintaining the immature morphology of a hematopoietic cell. The process comprises the steps of obtaining an enriched population of hematopoietic cells and co-culturing the enriched population of hematopoietic cells in the presence of osteoblast cells. The enriched population of hematopoietic cells are prepared from a population of mammalian cells that include hematopoietic cells. The immature morphology of the hematopoietic cell that is maintained include CD34$^+$ and a density of between about 1.010 gm/cm$^3$ and about 1.09 gm/cm$^3$. Alternatively, the immature morphology of the hematopoietic cell that is maintained is CD34$^+$, HLA-DR$^+$, Thy-1$^+$, and Lin$^-$ and a density of between about 1.010 gm/cm$^3$ and about 1.09 gm/cm$^3$.

Finally, the present invention provides a hematopoietic cell produced by the processes described herein. The hematopoietic cell has an immature morphology and is CD34$^+$, and having a density of between about 1.010 gm/cm$^3$ and about 1.09 gm/cm$^3$. The hematopoietic cell can additionally display the antigens HLA-DR$^+$, Thy-1$^+$, and Lin$^-$. The hematopoietic cell of the present invention is capable of differentiating into a blood cell including erythrocyte, platelet, monocyte, neutrophil, basophil, eosinophil, lymphocyte, or a mast cell.

DETAILED DESCRIPTION OF THE INVENTION

The present invention provides a process for propagating a hematopoietic cell. The process comprises the steps of obtaining an enriched population of hematopoietic cells and co-culturing the enriched population of hematopoietic cells in the presence of osteoblast cells. The enriched population of hematopoietic cells are prepared from a population of mammalian cells that include hematopoietic cells. As used herein, the term "hematopoietic cell" is an immature cell (stem cell) derived from a mammalian animal that is capable of differentiating into blood cells. Differentiation of a hematopoietic cell into blood cells consists of a complex series of steps known to those of skill in the art.

In a preferred embodiment, human hematopoietic cells are the subject of the present invention. Hematopoietic cells can be enriched from human bone marrow cells, umbilical cord cells, liver cells, spleen cells, or peripheral blood stem cells. As shown in Example 2 hematopoietic cells were isolated from the ilium of a human volunteer.

Alternatively, hematopoietic cells can also be purified from a population of mammalian cells that include hematopoietic cells by stimulating the growth of cells that have already begun to differentiate into more mature blood cells with a cytokine and by treating the stimulated cells with an antimetabolite (Berardi, A. C., et. al., 1995). In this method, the population of mammalian cells that include hematopoietic cells is treated with a cytokine that stimulates the growth of cells that have already begun differentiating into more mature blood cells. As the cells that have already begun differentiating into more mature cells proliferate in response to the cytokine, they are selectively killed by exposing the cells to an anti-metabolite (metabolic poison). Preferred cytokines include any cytokine that does not stimulate the growth of hematopoietic cells including c-Kit ligand and interleukin-3 (IL-3). Preferred anti-metabolites includes any metabolic poison that is capable of killing cells that have already differentiated into more mature blood cells, including 5-fluorouracil (5-FU) or 4-hydroxycyclophosphamide (4-HC).

The enriched population of hematopoietic cells can be prepared by exposing bone marrow cells to a hematopoietic cell antibody immunoreactive with a hematopoietic cell antigen and removing bone marrow cells which do not immunoreact with the hematopoietic cell antibody. A preferred hematopoietic cell antibody is an antibody that is immunoreactive with a hematopoietic cell antigen including anti-CD34. In another aspect, a second antibody immunoreactive with a hematopoietic cell antibody can be used to enrich the population of hematopoietic cells.

When a second antibody is utilized, a second antibody that is immunoreactive with a hematopoietic cell antibody can be used to enrich the population of hematopoietic cells. The use of a secondary antibody is generally known in the art. Typically, secondary antibodies are antibodies immunoreactive with the constant regions of the first antibody (hematopoietic cell antibody). Preferred secondary antibodies include anti-rabbit, anti-mouse, anti-rat, anti-goat, and anti-horse and are available commercially. In a preferred embodiment, secondary antibodies are conjugated to a solid substrate including tissue culture dish, agarose, polyacrylamide, and magnetic particles. In this embodiment, a hematopoietic cell antibody is first immunoreacted to a hematopoietic cell. The hematopoietic cell with the attached antibody is next exposed to the secondary antibody that is conjugated to a solid substrate. Enrichment of hematopoietic cells is achieved because only cells that present a hematopoietic cell antibody immunoreact with the secondary antibody. There are commercially available kit which provide secondary antibodies conjugated to magnetic particles. In this system, hematopoietic cells that present a hematopoietic cell antibody are purified by exposure to a magnetic field.

The preparation of hematopoietic cell antibodies are well known in the art and hematopoietic cell antibodies are available commercially. Both polyclonal and monoclonal antibodies are contemplated by the present invention. Means for preparing and characterizing antibodies are well known in the art (See. e.g., *Antibodies "A Laboratory Manual*, E. Harlow and D. Lane, Cold Spring Harbor Laboratory, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster, a sheep or a guinea pig. Because of the ease of use and relatively large blood volume of rabbits, a rabbit is a preferred choice for production of polyclonal antibodies.

A monoclonal antibody can be readily prepared through use of well-known techniques such as those exemplified in U.S. Pat. No 4,196,265, herein incorporated by reference.

Typically, the technique involves first immunizing a suitable animal with a selected antigen (e.g., CD34 or any other hematopoietic cell antigen) in a manner sufficient to provide an immune response. After a sufficient time to induce an immune response, spleen cells from the immunized animal are then fused with cells of an immortal myeloma cell. A number of immortal myeloma cells are available and the choice of the immortal cell is within the skill of an artisan. Immortal myeloma cells lack the salvage pathway of synthesizing nucleotides.

The fused spleen/myeloma cells are cultured in a selective medium to select fused spleen/myeloma cells from the parental cells. Fused cells are separated from the mixture of non-fused parental cells by the addition of agents that block the de novo synthesis of nucleotides in the tissue culture media. Unfused myeloma cells lack the enzymes necessary to synthesize nucleotides from the salvage pathway and are selectively killed in the selective media. Unfused lymphocytes also do not continue to grow in tissue culture. Thus, only cells that have successfully fused (hybridoma cells) can grow in the selection media. The hybridoma cell produces a monoclonal antibody and can be continuously grown.

Hematopoietic cells can be further enriched by equilibrium-density centrifugation of bone marrow cells. Equilibrium-density centrifugation of bone marrow cells provides a population of cells enriched in hematopoietic cells with a density of between about 1.010 and about 1.090 $gm/cm^3$, preferably between 1.040 and 1.080 $gm/cm^3$. In one embodiment, equilibrium-density centrifugation can be performed before the antibody purification of step discussed above. In this embodiment, the antibody purification step is carried out on bone marrow cells with a density of between about 1.010 and about 1.090 $gm/cm^3$. In a second embodiment, equilibrium-density centrifugation can be performed after the antibody purification as discussed above. Alternatively, the equilibrium-density centrifugation purification step can be performed twice—once before the antibody purification of step, and once after the antibody purification step.

The population of hematopoietic cells can be further enriched by removal of adherent cells (typically stromal cells), when the mammalian cells used are bone marrow cells, by exposing bone marrow cells to an adherent surface, typically tissue culture plastic or glass. Stromal cells adhere to tissue culture plastic or glass while hematopoietic cells do not adhere to the surface. Stromal cells can be removed before or after the immune purification step. Preferably, stromal cells are removed prior to the antibody purification step. The use of solid surfaces such as tissue culture plastic or glass is well known in the art. Tissue culture plastic and glass can be treated (e.g. silicone, nitrocellulose, nickel, etc.) to promote or inhibit cell adhesion. Treated and untreated surfaces are available commercially.

Hematopoietic cells are propagated by co-culturing the hematopoietic cells in the presence of osteoblasts. In one embodiment, the hematopoietic cells are co-cultured with a confluent or a non-confluent culture of osteoblasts. Human osteoblasts can be obtained by using a modification of the methods described by Robey and Termine as detailed in Example 1. In this method, bone is cleaned of loosely adherent tissue and ground to produce a uniform particle size (<1mm²) and digested with collagenase to prepare explants. The explants are then cultured under low $CA^+$ conditions and fetal bovine serum until confluent. The confluent cells are osteoblasts as indicated by the expression of ostcoblast specific proteins. Thereafter, the osteoblasts are maintained in calcium replete media. The concentration of calcium in the media used for culturing osteoblasts can range from about 1 mM to about 200 mM. As used herein, the term "co-culturing" is defined as the culturing of hematopoietic cells in the presence of osteoblasts. The osteoblasts can be confluent or non-confluent cultures. Alternatively, hematopoietic cells can be cultured in the presence of osteoblasts in a liquid culture in which the hematopoietic cells and osteoblasts do not adhere to a growing surface such as tissue culture dishes and roller bottles. The hematopoietic cells of the present invention can be co-cultured with osteoblasts for between about 1 week and about 8 weeks. Preferably, the hematopoietic cells are co-cultured with the osteoblasts for between about 2 weeks and about 6 weeks. Even more preferably, the hematopoietic cells are co-cultured with the osteoblasts for between about 2 weeks and about 4 weeks.

Alternatively, osteoblasts may be prepared from bone progenitor cells purified from bone marrow. Bone progenitor cells are isolated according to the method of Long. The bone progenitor cells are then induced to differentiate into osteoblasts by treatment with osteoblastic growth factors.

In yet another embodiment, osteoblasts can be obtained from immortal osteoblast/osteosarcoma cell lines. These cells lines include cells derived from human, rat and mouse cell lines as shown in Table 2.

TABLE 2

OSTEOBLAST\OSTEOSARCOMA CELL LINES

| Human | Rat |
|---|---|
| TE85 | Ros 17/2.8 |
| MG-63 | Ros 17/25.1 |
| SaOS-2 | ROB |
| HOBIT | |
| HS-OS-1 | |
| HOS | |
| KHOS-NP | |
| HOs-MMNG | |
| Mouse | Unknown Origin |
| MC3T3-E1 | MHNX |
| UMR-106 | KPDX |
| | U-2 |
| | OSPR |
| | KR1B |
| | MOB3-4-F2 |

The osteoblasts produce one or more cytokines that stimulate the propagation of hematopoietic cells and/or provides a microenvironment that promotes the propagation of hematopoietic cells. Those of skill in the art will recognize that there are many cytokines, including those listed in Table 3 below. Preferably, the osteoblast produces granulocyte colony stimulating factor (G-CSF), granulocyte macrophage colony stimulating factor (GM-CSF), FLK2/3 ligand, interleukin-11, leukemia inhibitory factor (LIF), macrophage colony stimulating factor (M-CSF), stem cell factor, transforming growth factor beta family (TGF-$\beta$) including TGF-$\beta_1$ through TGF-$\beta_5$, thrombopoietin, tissue necrosis factor family (TNF) including TNF-$\alpha$ and TNF-$\beta$.

TABLE 3

CYTOKINES

Angiogenin
Chemokines

C10
Epithelial Neuturophil Activating Peptide-78 (ENA-78)
Growth Related (GRO)-$\alpha$
GRO-$\alpha$
GRO-$\beta$
GRO-gamma
Macrophage Inhibitory Protein-1 (MIP-1)
MIP-1$\alpha$
MIP-1$\beta$
Monocyte Chemoatractant Protein-1 2 and 3 (MCP)

TABLE 3-continued

CYTOKINES

Regulated upon Activation Normal T-cell Expressed and Secreted (RANTES)
Interleukin-8 (IL-8)
Epidermal Growth Factors (EGF)

Amphiregulin (AR)
Beta-Cellulin
Epidermal Growth Factor (EGF)
Heparin Binding-EGF
TGF-$\alpha$
Fibroblast Growth Factors (aFGF)

Acidic Fibroblast Growth Factors (aFGF)
Basic Fibroblast Growth Factors (bFGF)
FGF-4
FGF-5
FGF-6
FGF-7
Bone Morphogenic Factors of Proteins (BMPs)

BMP-1
BMP-2
BMP-3
BMP-4
BMP-5
BMP-6
BMP-7
BMP-7
BMP-8
Erythropoietin (EPO)
Granulocyte Colony Stimulating Factor (G-CSF)
Granulocyte-Macrophage Colony Stimulating Factor (GM-CSF)
Gro Alpha, Beta, Gamma (No other Name that I am aware of)
FLK2/3 Ligand (No other Name that I am aware of)
Insulin Like Growth Factors-I and II (IGF-I and II)
Interferons (IFN)

IFN-Alpha
IFN-Beta
IFN-Gamma
Interleukins

Interleukin-1 alpha
Interleukin-1 beta
Interleukin-2
Interleukin-3
Interleukin-5
Interleukin-6
Interleukin-7
Interleukin-8
Interleukin-9
Interleukin-10
Interleukin-11
Interleukin-12
Interleukin-13
Latency Associated Peptide (LAP)
Leukemia Inhibitory Factor (LIF)
Macrophage Colony Stimulating Factor (M-CSF)

$\beta$-Nerve
Oncostatin-M (OSM)
Osteoclast-Colony Stimulating Factor
Platelet Derived Growth Factors Alpha & Beta Heterodimers and Homodimers (PDGF)
Pleiokine Family Pleiotrophin
Midkine
Secretory Leukocyte Protease Inhibitor
Stem Cell Factor (SCF or c-Kit Ligand)
Transforming Growth Factor Beta Factors (TGF-Beta)

TGF-$\beta_1$ Through TGF-$\beta_2$
Thromobopoietin

TABLE 3-continued

CYTOKINES

Tumor Necrosis Factors (TNF's)

TNF-α
TNF-β (Lymphotoxin)
Vascular Endothelial Growth Factor

VEGF
Placenta Growth Factor

---

Yet another aspect of the present invention provides a hematopoietic cell prepared by co-culturing an enriched population of hematopoietic cells in the presence of osteoblasts. The hematopoietic cell that is provided by co-culturing have a morphology that is $CD34^+$, and has a density of between about 1.040 gm/cm$^3$ and about 1.09 gm/cm$^3$. In addition to $CD34^+$, the hematopoietic cell provided by the present invention can also display the antigens $HLA-DR^+$, $Thy-1^+$, and $Lin^-$. CD34 is a pan-hematopoietic antigen that is found in all blood cells that have been studied to date. HLA-DR is a class 2 HLA antigen (histocompatibility antigen) expressed on a wide variety of cells which are involved in the cooperation and communication between immune cells. Thy-1 antigens are antigens which are also expressed on a wide variety of cells of bone marrow origin including lymphocytes. The function of Thy-1 is not presently known. Lin, as known to those of skill in the art, is a collection of antigens including CD7, CD15, CD19, CD33, and CD38 which are found on more mature blood cells.

The hematopoietic cell of the present invention is capable of differentiating into a blood cell including erythrocyte, platelet, monocyte, neutrophil, basophil, eosinophil, or lymphocyte, including B-lymphocyte and T-lymphocyte, and mast cell. The morphology of these blood cells is known to those of skill in the art.

The hematopoietic cell of the present invention can be separated from the osteoblasts which are co-cultured with the hematopoietic cell and collected. The hematopoietic cells can be separated from the osteoblasts by antibody purification, equilibrium-density centrifugation, exposure to an adherent surface as described herein. Alternatively, the hematopoietic cells can be separated and collected from the osteoblasts by exposing the co-culture (hematopoietic cells in co-culture with osteoblasts) to an antimetabolite that selectively kills osteoblasts.

In yet another embodiment, the hematopoietic cell propagated by the methods disclosed herein can be infused into a human in need of hematopoietic cells. The hematopoietic cells are infused into the human by injecting the hematopoietic cells directly into the bloodstream of the human. Alternatively, the hematopoietic cells can be introduced into the human by directly introducing the hematopoietic cells into the marrow cavity of a bone.

Patients in need of hematopoietic cells typically include those with leukemias, requiring bone marrow transplantation, or those undergoing chemotherapy. Patients undergoing chemotherapy lose their own hematopoietic cells as a consequence of their exposure to the chemotherapeutic agents. In these patients, the hematopoietic cells of the present invention can be infused into the bloodstream of the patient concurrently with treatment or after treatment with the chemotherapeutic agent. Alternatively, the hematopoietic cells propagated by the present invention can be directly introduced into the marrow cavity of a bone of the patient.

In addition, the hematopoietic cells of the present invention are candidates for genetic therapy for genetic blood diseases. Genetic blood diseases include many well known diseases such as sickle cell anemia, Tay-Sachs disease, and thalassemia. When the hematopoietic cell is used for genetic therapy, the hematopoietic cell is first propagated according to the methods described herein. The genes of the hematopoietic cell is then manipulated by well know techniques including direct injection of genetic material into the hematopoietic cell, and introduction of genetic material through the use of vectors, including viral based vectors. The hematopoietic cell is then introduced into the patient where they propagate and differentiate into mature blood cells without the genetic defect.

In another aspect, the present invention provides a process for maintaining the immature morphology of a hematopoietic cell. The process comprises the steps of obtaining an enriched population of hematopoietic cells and co-culturing the enriched population of hematopoietic cells in the presence of osteoblast cells. The enriched population of hematopoietic cells are prepared from a population of mammalian cells that include hematopoietic cells. The immature morphology of the hematopoietic cell that is maintained include $CD34^+$, and have a density of between about 1.010 gm/cm$^3$ and about 1.09 gm/cm$^3$. The immature morphology can also include $HLA-DR^+$, $Thy-1^+$, and $Lin^-$. Preferably, the density is between about 1.040 gm/cm$^3$ and about 1.08 gm/cm$^3$. Even more preferably, the density is between about 1.070 gm/cm$^3$ and about 1.08 gm/cm$^3$.

EXAMPLE 1
HUMAN OSTEOBLASTS

Human osteoblasts were obtained using a modification of methods described by Robey and Termine (Robey et al., 1985). Normal human trabecular bone was obtained from patients undergoing orthopedic surgery in accordance with the University of Michigan's policies for Human Subjects. Bone cleaned of loosely adherent tissue was ground to produce a uniform particle size (size $\leq 1$ mm$^2$) (BioComp Minimill, W. Lorenz, Jacksonville, Fla.) and incubated in 1 mg/ml bacterial collagenase (Type P, Boehringer Mannheim Biologicals, Indianapolis, Ind.).

The explants were placed into culture until confluent monolayers were produced in a 1:1 (vol/vol) mixture of F12/DMEM medium (Biofluids, Rockville, Md.) with low $Ca^{+2}$ and 10% fetal bovine serum. Thereafter, cultures were maintained in calcium replete DMEM/F12 (1:1 vol/vol) medium containing 10% heat inactivated FBS, antibiotics, 10 mM β-glycerophosphate and 10 mg/ml L-ascorbate. To verify that the cells were osteoblasts, several histochemical assays were performed including in vitro mineralization, and expression of high levels of alkaline phosphatase Taichman et al., 1992).

Total cellular RNA was recovered from osteoblasts as reported in (Guba et al., 1992). RNA quantity and integrity were checked by gel electrophoresis with ethidium bromide and absorbance at $A_{260}/A_{280}$.

Sense and antisense primers were prepared by the oligonucleotide synthesis core at the University of Michigan. The primers utilized in these investigations were reported previously (Guba et al., 1992) with the exceptions of those for osteocalcin (nucleotides 1046 to 1066 sense) GGCAGC-GAGGTAGTGAAGAG (SEQ ID NO:15) and (nucleotides 1364 to 1384, antisense) GATGTGGTCAGCCAACTCGT (SEQ ID NO:16). The gene bank accession number for human osteocalcin is X04143.

Reverse transcriptase-polymerase chain reaction (RT-PCR) was performed for 35 cycles as previously reported (Guba et al., 1992). PCR products were electrophoresed in 3% agarose and visualized with ethidium bromide. As positive cytokine controls, RNA was isolated from either peripheral blood lymphocytes stimulated with PHA (3.0 µg/ml) and PMA (3 ng/ml) or IL-1α (25 U/ml) stimulated human bone marrow stromal cells. To control for DNA contamination, reverse transcriptase was omitted from the reverse transcriptase reaction.

G-CSF ELISAs were performed using the double-antibody sandwich method (R+D Systems). Based upon parallel assays of known diluted standards, the sensitivities of the assays for G-CSF in unconcentrated medium is 25 to 2,000 pg/ml. Aliquots of conditioned medium were concentrated 4–10 fold by centrifugation at 1,000 g in a 25° C. fixed angle JA-17 rotor (Beckman, Palo Alto, Calif.) in Centricon-10 concentrators (Amicon Division of W. R. Grace and Co, Danvers, Mass.) until the desired volume was reached. Used in conjunction with concentrated medium, the G-CSF ELISA was able to detect concentrations as low as 4 pg/ml.

Indirect immunohistochemistry phase-contrast microscopy was performed for G-CSF on 2% paraformaldehyde fixed primary human osteoblasts grown in 96-well tissue culture plates. Paraformaldehyde-fixed primary human osteoblasts were incubated with 10 µg/ml of a murine monoclonal anti-human G-CSF in PBS or an isotype control (FOPC-21, Sigma) at 4° C. for two hours followed by a rabbit anti-murine FITC-conjugated serum at a 1/64 dilution (Sigma Chemical Company, St. Louis, Mo.). Nonspecific binding was blocked with 10% normal rabbit serum.

EXAMPLE 2
HEMATOPOIETIC, CD34+ CELLS

Bone marrow cells obtained from healthy adult volunteers were diluted 1:4 (vol/vol) in IMDM and separated by density separation on Ficcol-Hypaque (specific gravity 1.077) to recover mononuclear cells. Following two rounds of plastic adherence at 37° C. for one hour each in IMDM medium with 20% FBS (to remove monocytes, platelets and megakaryocytes), the non-adherent cells were recovered. CD34+ hematopoietic progenitor populations were isolated utilizing an avidin-biotin immunoaffinity process (CellPro Inc., Bothwell, Wash.).

CD34+ or NFS-60 cells were seeded directly onto osteocalcin+, c-kit ligand− confluent osteoblast monolayers in 96-well tissue culture plates at a final density of 1×10$^4$ cells/well and incubated for 3–14 days. Either vehicle, 10 µg/well of an affinity purified IgG fraction of neutralizing goat anti-human G-CSF serum (R+D Systems), or 10 µg/well of normal goat IgG serum were added to cultures daily. Absolute cell numbers were determined by manual hemocytometer counting in PBS containing 0.4% trypan blue (Sigma).

EXAMPLE 3
CO-CULTURING OF HEMATOPOIETIC CELLS AND OSTEOBLASTS

Unstimulated primary human osteoblasts are a normal source of G-CSF. Primary osteoblasts were obtained utilizing the methods of Robey and Termine (Robey et al., 1985), where osteoblasts emerge from collagenase-digested human bone during the second to third week of culture. These cells express several functional characteristics of osteoblasts including the expression of mRNA for matrix Gla protein (not shown) and the osteoblast specific protein osteocalcin (bone Gla protein) (Taichman et al., 1992; Gerstenfeld et al., 1987; and Hauschka et al., 1989). Mineralization of their extracellular matrix, and the expression of alkaline phosphatase were examined by histochemical methods. (Taichman et al., 1992).

Primary human osteoblast cultures were examined for their expression of mRNA for several cytokines using reverse transcriptase (RT-PCR). Osteoblasts constitutively express mRNA for several cytokines including TNF-α, IL-6, GM-CSF, and G-CSF, but failed to express mRNA for IL-1α, IL-3, and c-kit ligand. As c-kit ligand is constitutively produced by stromal fibroblasts, the absence of detectable mRNA for this hematopoietic growth factor shows minimal fibroblast contamination in the primary cultures.

To further assure that these results are representative of normal osteoblast physiology, we induced the differentiation of osteoblasts from non-adherent low density bone marrow osteoprogenitors utilizing a serum deprivation method of Long, et al. The advantages of these methods are i) differences in osteoblast populations based upon maturational stage is eliminated ii) osteoblasts are obtained from sites actively involved in hematopoietic functions iii) samples can be obtained from younger individuals [age=18–40] (explant bone: mean patient age=64.5 years, range=53–91 years, N=14), and iv) the possibility that osteoblasts recovered from bone explants represent resting osteoblasts/osteocyte that have reentered replicative pools.

In this technique non-adherent low-density human marrow cells differentiate into osteoblast-like cells within a week in serum free culture. These cells mineralize their extracellular matrix, express alkaline phosphatase, express mRNA for osteocalcin and do not express c-kit ligand message. These data show that the cells have an osteoblasts phenotype and are not contaminated by fibroblasts. A similar cytokine profile was observed for these osteocalcin+, c-kit ligand− cells. In addition, a comparable pattern of cytokine mRNAs expressed by the human osteosarcoma cell lines, −MG-63 and SaOS-2 was shown. (See Table 4 below.)

TABLE 4

| Cell | Asc/βGP | LPS | G-CSF | GM-CSF |
|---|---|---|---|---|
| Experiment #1 (pg/ml/24 hours) | | | | |
| MG-63 | − | − | 28 ± 7 | 24 ± 3 |
| MG-63 | + | − | 0* | 0 |
| SaOS2 | − | − | 0 | 0 |
| SaOS2 | + | − | 0 | 0 |
| Experiment #2 (pg/ml/6 hours) | | | | |
| MG-63 | − | − | 0 | 6 ± 1 |
| MG-63 | − | + | 241 ± 17 | 60 ± 5 |
| MG-63 | + | − | 0 | 0 |
| MG-63 | + | + | 229 ± 1 | 16 ± 1 |

In Experiment #1, conditioned medium was collected over a 24 hour period (N = 3). In experiment #2, MG-63 cells were stimulated with 25 µg/ml E. coli LPS for 6 hours commencing on day 18 of culture (n = 2). Aliquots of conditioned medium were concentrated 2 fold by centrifugation in Centricon-10 concentrators. In conjunction with concentrated medium, the ELISAs was able to detect concentrations as low as 20 pg.ml for G-CSF and 4 pg/ml GM-CSF.
*Less than detection limit of assay. Data reported as mean ± S.D.

These results show that osteoblasts constitutively express G-CSF mRNA. We next determined that the G-CSF message is translated and that the protein is presented to hematopoietic cells. To determine whether G-CSF message is translated, immunohistochemical staining for G-CSF on paraformaldehyde-fixed primary human osteoblasts utilizing a monoclonal anti-human G-CSF antibody was performed. G-CSF is localized on the cell membrane of the osteoblasts and not in the interstitial extracellular matrix. To quantify G-CSF production from unstimulated osteoblasts expressing G-CSF mRNA, salt extracts of extracellular matrix (Gordon et al., 1987 and Roberts et al., 1988) and concentrated conditioned medium were analyzed for G-CSF by ELISA (Guba et al., 1992). As positive controls for –G-CSF production, osteoblasts or stromal cells were exposed to lipopolysaccharide (LPS) or IL-1 α, respectively (Felix et al., 1988; Felix et al., 1991; and Greenfield et al., 1993). LPS stimulation of osteoblasts resulted in the production of 21 pg/ml/24 hour/$10^4$ cells of soluble G-CSF. No G-CSF could be detected in the medium or extracellular matrix of unstimulated osteoblasts, showing that under basal conditions G-CSF may not be released as a soluble protein.

To determine whether the G-CSF detected by immunohistochemical methods had functional activity, the proliferation of the G-CSF dependent cell line NFS-60 in co-culture with osteocalcin$^+$, c-kit ligand$^-$ human explant osteoblasts were evaluated Shirafuji et al., 1989). A neutralizing antibody to human G-CSF was utilized to directly test whether osteoblast-derived G-CSF has biological activity. NFS-60 cells proliferated in the presence of osteoblast monolayers but not in medium alone. Inclusion of a neutralizing anti-G-CSF antibody in the cultures caused a 41% reduction in the proliferation of the NFS-60 cells. The proliferation of NFS-60 cells was not affected by a control antiserum nor were significant differences in proliferation of the NFS-60 cells observed when the cells were grown in osteoblast conditioned medium (50% vol:vol) alone, with or without the neutralizing anti-human G-CSF antibody.

These results obtained with the NFS-60 cell line show that osteoblasts stimulate the proliferation of human hematopoietic progenitors by producing G-CSF. To examine this possibility, CD34$^+$ hematopoietic progenitor cells were isolated and seeded onto confluent osteocalcin$^+$, c-kit ligand$^-$ osteoblast monolayers. At 14 days, the hematopoietic cells were recovered and counted.

The effect of G-CSF in this system was tested by the addition of an antiserum to human G-CSF. An 8-fold increase in cell recovery was observed for hematopoietic cells grown in co-culture with osteoblasts over a 2 week period. 55.4% of the osteoblast-induced increase in cell recovery was directly blocked by coincubation of neutralizing anti-G-CSF antibody in the culture. 44.5% of the growth activity produced by osteoblasts was not due to G-CSF, either alone or in combination with other osteoblast-derived cytokines.

Furthermore in Wright-Geimsa cytospin preparations many of the hematopoietic cells recovered after two weeks of co-culture maintained an immature morphology (23±6% myeloblasts/promyelocytes; 51.7±5.5% myelocytes/metamyelocytes; 21±5% bands/polymorphonuclear neutrophils and; 4.3±0.6% monocytes). These data show that osteoblasts might produce additional factors that support the survival and limited proliferation of primitive myeloid cells as well.

The biologic data utilizing CD34$^+$ and the NFS-60 cell line in conjunction with the mRNA, and immunohistochemistry results establishes that human osteoblasts produce G-CSF. Osteoblast-derived G-CSF is accessible to target cells when it is associated with osteoblast's cell membrane. The possible mechanisms by which growth factors become cell associated or retained by components of the extracellular matrix and presented to target cells have not yet been fully elucidated. Cell associated forms of M-CSF, c-kit ligand, IL-1α and matrix associated forms of IL-3 and GM-CSF have been described (Gordon et al., 1987; Roberts et al., 1988; Shirafuji et al., 1989; Toksoz et al., 1992; Kurt-Jones et al., 1985; Stein et al., 1990; Gordon et al., 1993; and Fava et al., 1987.

The conclusions of the experiments evaluating G-CSF production with bioassays verses ELISA of conditioned osteoblast medium are that either i) immunoreactive G-CSF is diffusible only over extremely short distances before inactivation ii) the neutralizing G-CSF antibody does not have access to the microenvironment between osteoblasts and stem cells, iii) directed cell-cell transfer of G-CSF occurs between the osteoblasts and hematopoietic progenitors, as has been reported for IL-2 (Poo et al., 1988) and iv) G-CSF or a closely related molecule is presented to hematopoietic cells as a cell membrane associated protein or bound in an active form to extracellular matrix molecules.

At least three forms of G-CSF have been identified on immunoblots, including 18, 28 and 32-kD forms (Singer et al., 1993). The major secreted species appears to be the 18 kD form, however, the biological nature of the higher molecular weight proteins are unknown but possibly represents cell-associated or inactive protein precursors (Singer et al., 1993).

The antibody to G-CSF neutralized only 55% of the CD34$^+$ cell's proliferative activity produced by the osteoblasts. Thus, it is likely that more than one factor produced by osteoblasts support the proliferation of hematopoietic stem cells. It is possible that unique osteoblast-derived cytokines are responsible for proliferative effects on NFS-60 and CD34$^+$ cells. These observations show that stem cell self renewal is influenced by either osteoblast-derived cytokines or adhesive interactions between the two cell types or possibly both.

Human osteoblasts produce cytokine signals which regulate hematopoiesis. Hematopoietic myeloid stem cell differentiation occurs in direct proximity to osteoblasts within the bone marrow cavity. It is likely that this intimate physical association established early in life facilitates interactions between bone and hematopoietic cells. Human osteoblasts are a constitutive source of the hematopoietic growth factor G-CSF.

EXAMPLE 4
HUMAN OSTEOSARCOMA CELL LINES MG-63 AND SAOS-2

It is known in the art that stromal cells of the bone marrow provide the structural scaffolding for hematopoiesis (Mayani et al., 1992). Recently however it has been determined that marrow stromal cells also produce several factors critical to the development of blood cells. In this context human and animal model systems have demonstrated that i) direct stromal cell-to-blood cell contact, ii) stromal cell production of the extracellular bone marrow matrix and iii) cytokine synthesis by stromal cells are all relevant to the formation of various blood cells (Metcalf, 1988; Dexter et al., 1990; and Dexter et al., 1987).

It is known that while diverse cell types reside within the bone marrow stromal microenvironment, the relative contributions of each cell type to hematopoiesis is still obscure. Bone marrow fibroblasts predominate in ex vivo bone marrow stromal cultures grown to confluence, although their relative contribution to the in vivo microenvironment is probably somewhat smaller. These cells constitutively secrete IL-6 and c-kit ligand (SCF) and likely other membrane-bound cytokines as well (Gimble et al., 1991; Guba et al., 1992; Toksoz et al., 1992; Kurt-Jones et al., 1985; and Stein et al., 1990).

Upon stimulation with the inflammatory monokines IL-1α and TNF-α, bone marrow fibroblasts also secrete G-CSF and GM-CSF (Kittler et al., 1992; Guba et al., 1992 and Fibbe et al., 1988). Similar activities are probably shared by bone marrow microvascular endothelial cells. Adipocytes are also plentiful within the bone marrow cavity, but their functional significance at present is largely unknown.

In the bone marrow, each of these cell types probably represents a local specialization of a widely expressed cell lineage. Osteoblasts, on the other hand, particularly those localized to the endosteal surfaces of marrow surfaces may represent a cell type with a more restricted expression. For detailed molecular and biochemical investigations therefore, osteoblast tumor cell lines represent an important useful alternative cell source for study.

The hematopoietic biochemistry of homogeneous osteoblasts cell lines including the non-mineralizing MG-63 human osteosarcoma cell line and the mineralizing SaOS-2 cell line were investigated. Specifically, we assayed these cells for the production of c-kit ligand, IL-1β, IL-3, IL-6, G-CSF, GM-CSF, LT, TGF-β$_1$, and TNF-α, both in the presence and absence of L-ascorbate and β-glycerol phosphate; biochemical signals which may further enhance the development of osteoblast phenotype from immature osteoblasts. The data show that G-CSF is indeed produced by these cells in several membrane forms. These results confirm that osteoblasts play a critical role in hematopoietic regulation, and demonstrate that these cell lines should offer the opportunity for more precise biochemical definition of these roles.

The human osteosarcoma cell lines MG-63 (ATCC CRL1424) and SaOS-2 (ATCC 85-HTB) were maintained in MEM with Earle's salts or McCoy's 5A medium with 10% heat inactivated fetal bovine serum. For these experiments, cells were replated to an initial density of 2.0×10$^5$ cells/cm$^2$ with complete medium changes on days 5, 7, 10 and 14. Freshly prepared β-glycerol phosphate (10 mM) and L-ascorbate (50 μg/ml) were added as required.

Total cellular RNA was recovered from the osteosarcoma by the methods of Chomczynski and Sacchi (Chomcynski et al., 1987). Cell layers were washed twice with PBS and lysed directly in GITC (4M guanidine isothiocyanate, 0.5% sarcosyl, 25 mM citric acid, pH 7.0 and 0.007% β-mercaptoethanol). RNA quantity and integrity were be checked by electrophoresis with ethidium bromide and absorbance at A$_{260}$/A$_{280}$.

Sense and antisense primers were prepared by the oligonucleotide synthesis were designed to cross intron/exon boundaries (Ponte et al., 1984; March et al., 1985; Yand et al., 1986; Hirano et al., 1986; Nagata et al., 1986; Wong et al., 1985; Huang et al., 1990; Gray et al., 1984; Celest et al., 1986; Derynck et al., 1985; and Marmenout et al., 1985). The β-Actin antisense primer incorporated additional sequences for the T7 promotor (Table 5).

TABLE 5

| | |
|---|---|
| CAGTAGTGACTCATCCGA | SEQ ID NO: 1 |
| TTCCTTCCTCCTCTTCCTCCT | SEQ ID NO: 2 |
| GGCCCACTCCATGAAGGCTGCATG | SEQ ID NO: 3 |
| GTCAGTGATAGAGGGTGGCCCCCC | SEQ ID NO: 4 |
| GGATCCTTGAAGACAAGCTGGGTTAACTGCTCTAAC | SEQ ID NO: 5 |
| AAGCTTGATATGGATTGGATGTCGCGTGGGTGC | SEQ ID NO: 6 |
| GGATCCTCCTTCTCCACAAGCGCCTTCGGTCCA | SEQ ID NO: 7 |
| AAGCTTGTTCCTCACTACTCTCAAATCTGTTCTG | SEQ ID NO: 8 |
| TTCTCTTGGCTGTTACTGCCAGGA | SEQ ID NO: 9 |
| GTCTTCCTTGATGGTCTCCACACTC | SEQ ID NO: 10 |

TABLE 5-continued

| | |
|---|---|
| CACAGTGCACTCTGGACAGTGCAGGAA | SEQ ID NO: 11 |
| CATTCCCAGTTCTTCCATCTGCTGCCAGAT | SEQ ID NO: 12 |
| GAGCATGTGAATGCCATCCAGGAG | SEQ ID NO: 13 |
| CTCCTGGACTGGCTCCCAGCAGTCAAA | SEQ ID NO: 14 |
| GGCAGCGAGGTAGTGAAGAG | SEQ ID NO: 15 |
| GATGTGGTCAGCCAACTCGT | SEQ ID NO: 16 |
| ACCACTGCCGCACAACTCCGGTGAC | SEQ ID NO: 17 |
| ATCTATGACAAGTTCAAGCAGAGTA | SEQ ID NO: 18 |
| GCAGTAAGATCATCTTCTCGAACC | SEQ ID NO: 19 |
| CAGATAGATGGGCTCATACCA | SEQ ID NO: 20 |
| TGTTGGCCTCACACCTTCAGCTG | SEQ ID NO: 21 |
| ATCTGTGTGGGTGGATAGCTGGTCT | SEQ ID NO: 22 |
| GAAGGGATCTGCAGGAATCGTGTG | SEQ ID NO: 23 |
| GCCCTTGTAAGACCTGGCTGTCTC | SEQ ID NO: 24 |

Reverse transcriptase polymerase chain reaction (RT-PCR) was performed by incubating 1.0 μg RNA, 10X RT buffer (1X RT buffer: 50 mM Tris, pH 8.3, 50 mM KCl 8.0 mM MgCl$_2$, and 10 mM dithiothreitol), 25 mM dXTP mix (25 mM of each dXTP (ACGT)), 3.0 μg oligo d(T), and 2.5 U reverse transeriptase (M-MLV Reverse Transcriptase, GIBCO-BRL, Gathersburg, Md.) at 38° C. for one hour.

One-fifth of the double stranded product was mixed with 10X Taq/RT buffer (1X Taq/RT buffer: of 10 mM Tris, pH 8.3, 50 mM KCl, 1.5 mM MgCl$_2$ 0.01% gelatin, and 2.0 mmol/L dithiothreitol), 1 mM dXTP mix, 500 ng of each sense and antisense oligonucleotides, and 2.5 U Taq polymerase (AmpliTaq DNA Polymerase; Perkin Elmer Cetus, Norwalk, Conn.). The samples underwent thermal cycling at 94° C. for 1 min and 72° C. for 3 minutes for 35 cycles, then finally a 10-minute extension at 72° C. (Perkin Elmer Cetus DNA thermal cycler).

The products were electrophoresed in 3% agarose and visualized using ethidium bromide. Positive RNA specimens were included in the analyses as controls. The samples amplified included IL-1α and TNF-α stimulated human bone marrow stroma (c-kit ligand, G-CSF, GM-CSF, TNF-α, LT) or peripheral blood lymphocytes stimulated with PHA (3.0 μg/ml) and PMA (3 ng/ml) for 18 hours (G-CSF, GM-CSF, IL-3). To control for false positives due to "overamplification" or DNA contamination reverse transeriptase was omitted from the reaction and primers were designed to cross intron\exon boundaries.

For determination of in vitro mineralization, osteoblast cultures were fixed in 10% normal buffered formalin and stained for bound phosphate by the Von Kossa technique using 5% (w/v) silver nitrate in PBS (Bellows et al., 1986). The black nodules (≧1 mm$^2$) were enumerated under a dissecting microscope (4X).

Assays for alkaline phosphatase activity were performed using P-nitrophenylphosphate as a substrate (Sigma). Cells grown in 24 well plates were scraped into ice cold harvest buffer (10 mM Tris HCl pH 7.4, 0.2% NP40 and 2 mM PMSF), homogenized on ice for 15 seconds at 15,000 rpm and assayed for activity at 37° C. in 96 well ELISA plates for 15 mins. The enzymatic reactions were terminated with 0.1N NaOH and read at $A_{405}$ on ELISA plate reader (Molecular Devices Corp.). The results are expressed as units of enzyme activity/min/$10^5$ cells (Reddi et al., 1972).

ELISAs were performed using the double-antibody sandwich method with commercially available kits for osteocalcin (Metra BioSystems, Palo Alto, Calif.), G-CSF and GM-CSF (R+D Systems, Minneapolis, Minn.). Based upon parallel assays of known standards, the sensitivities of the assays of unconcentrated conditioned medium were as follows: Osteocalcin 5 to 80 ng/mL; G-CSF 39 to 2500 pg/mL; GM-CSF 8 to 500 pg/mL. Aliquots of conditioned medium were concentrated 2 fold by centrifugation at 1,000g in a 25° C. fixed angle JA-17 rotor (Beckman, Palo Alto, Calif.) in Centricon-10 concentrators (Amicon Division of W. R. Grace and Co, Danvers, Mass.) until the desired volume was reached. Used in conjunction with concentrated medium, the G-CSF and GM-CSF ELISAs were able to detect concentrations as low as 19 and 4 pg/ml, respectively.

Indirect immunohistochemistry phase-contrast microscopy was performed for G-CSF, GM-CSF and IL-6 on cells grown for two weeks in 96-well tissue culture plates. Paraformaldehyde-fixed cells were incubated with either 10 μg/ml of a murine anti-human monoclonal antibodies to G-CSF or GM-CSF (Genzyme) in PBS or an isotype control (FOPC21, Sigma Chemical Company, St. Louis, Mo.) at 4° C. for two hours followed by a rabbit anti-murine FITC-conjugated serum at 1/64 dilution (Sigma). Nonspecific binding was blocked with 10% normal rabbit serum.

Osteosarcoma cells grown for 14 days in T75 flasks were incubated for an additional 12 hours with 1 μCi Trans$^{35}$S-labeled (SA: 1108 Ci/mmol,ICN Biochemicals, Irvine Calif.) in 5 ml cysetine and methionine free DMEM and 0.5% BSA (w/v) (Life Technologies)$^{35}$S metabolic labeling of G-CSF. The cells were lysed in ice-cold PBS-TD lysis buffer (1% Triton X-100, 0.5% deoxycholic acid, 1 μg/ml phenylmethylsulfonyl fluoride, 1 μg/ml aprotinin, 1 μg/ml leupeptin, 1 μg/ml pepstatin (Sigma)) using a rubber policeman and passage through a 27G needle on ice for 10 min.

The nuclei and cellular debris were removed by centrifugation at 16,000xg for 15 min at 4° C. Lysates were normalized for total TCA precipitable counts ($5 \times 10^6$ cpm) and incubated for 4 hours at 4° C. with 10 ug rabbit anti-human G-CSF IgG (Genzyme) or nonimmune rabbit IgG. Immune complexes were collected with protein A sepharose (Sigma), washed extensively and eluted into 1xlaemmli buffer and electrophoresed in 12% polyacrylamide gels under reducing conditions. Final detection was accomplished by autoradiography.

MG-63 and SaOS-2 human osteosarcoma cell lines have been extensively studied as potential models of osteoblast function (Aronow et al., 1990; Gerstenfeld et al., 1987; and Owen et al., 1990). To first confirm that the cell lines do indeed display an osteoblast phenotype, these cells were cultured for 18 days in the presence or absence of L-ascorbate and β-glycerol phosphate. During the culture interval MG-63 and SaOS-2 cell number increased 7 to 9 fold, respectively. After 7-10 days in culture SaOS-2 cells begin to mineralize their extracellular matrix. Under similar conditions the MG-63 osteosarcoma cells failed to mineralize their extracellular matrix, but did express alkaline phosphatase and secreted osteocalcin albeit at lower levels than SaOS-2 cells. Thus, both cell lines exhibit several features of osteoblast function although the MG-63 cell line expression of the osteoblast phenotype is not as pronounced is SaOS-2 cells.

To determine whether these two cell lines express messages for hematopoietic cytokines the cells were cultured in the presence or absence of L-ascorbate and β-glycerol phosphate for 18 days. On days 7, 10, 14 and 18 RNA was isolated and examined for mRNA for osteocalcin and several cytokines using reverse transcriptase polymerase chain reaction. MG-63 cells constitutively express mRNA for osteocalcin as well as for G-CSF, IL-1 β, TGF-$β_1$, TNF-α and G-CSF, but failed to express mRNA for IL-3 or LT. The expression of mRNA for GM-CSF and IL-6 arose later in the culture period. MG-63 cells did express c-kit ligand but only in the absence of L-ascorbate and β-glycerol phosphate.

RNA message expression by SaOS-2 cells for osteocalcin, G-CSF, TGF-$β_1$, and TNF-α was similar to the mRNA expression pattern of the MG-63 cells. SaOS-2 cells also failed to express mRNA for 1L-3 and LT, and expressed mRNA for c-kit ligand only in the absence of L-ascorbate and β-glycerol phosphate. Like the MG-63 cells, mRNA expression for GM-CSF and IL-6 appeared to develop later in the culture period. In contrast with the MG-63 cells however, IL-1β mRNA expression by SaOS-2 cells arose later in the culture period. Thus, both of these cell lines constitutively express mRNA for G-CSF, TGF-$β_1$ and TNF-α in the presence and absence of L-ascorbate and β-glycerol phosphate, however c-kit ligand mRNA was expressed only in the absence of ascorbate and β-glycerol phosphate induction and GM-CSF and IL-6 expression appeared to develop with increasing culture age.

Since G-CSF and GM-CSF RNA messages were detected for these cells in the presence or absence of L-ascorbate and β-glycerol phosphate treatments, we next determined that these proteins are produced as soluble proteins as determined by ELISA. G-CSF or GM-CSF was not detected following a 24 hour collection period commencing on days 6, 9, 13 (not shown), but was detectable in day 18 conditioned medium. Under these conditions only MG-63 cells produced detectable levels of G-CSF and GM-CSF in the absence of L-ascorbate and β-glycerol phosphate induction despite 2-fold medium concentration.

Next we determined that the biochemically induced (L-ascorbate and β-glycerol phosphate) osteosarcoma cell lines maintain the capacity to produce soluble G-CSF and GM-CSF following inflammatory stimulation. For these investigations the MG-63 were exposed to E. coli lipopolysaccharide (LPS) for 6 hours. The data showed that MG-63 cells maintain the capacity to produce G-CSF and GM-CSF regardless of L-ascorbate and β-glycerol phosphate treatments. Similar results were obtained for SaOS-2 cells. Thus osteosarcoma cells are capable of producing soluble G-CSF and GM-CSF under unusual conditions such as LPS stimulation, however, under basal (non-inflammatory) conditions, produce detectable GM-CSF and G-CSF levels only in the absence of ascorbate and β-glycerol phosphate induction.

Since RNA messages for G-CSF and GM-CSF were detected by RT-PCR but no protein was identified by ELISA, we next determined that these cells produce these G-CSF and GM-CSF as membrane associated forms. For these investigations, indirect immunohistochemistry phase-contrast microscopy was performed on day 14 L-ascorbate and β-glycerol phosphate treated cells using G-CSF, GM-CSF and IL-6 anti-human monoclonal antibodies. Second stage detection employed an anti-murine FITC-conjugated serum. For both MG-63 and SaOS-2 cells, G-CSF and GM-CSF was observed bound either to the extracellular matrix or the cell membrane of the osteosarcoma cells.

In contrast, no IL-6 could be detected by immunohistochemistry. Therefore these data illustrate that MG-63 and SaOS-2 cells translate the RNA messages for G-CSF and GM-CSF but they appear to be produced in insoluble forms. That is, they are likely to be membrane bound.

While insoluble forms of GM-CSF have been described, at present little is known, about the insoluble forms of G-CSF (18, 28 and 32-kD forms have been described) (Zipori, 1992). Therefore these cells provide an unique opportunity to study in further detail the nature and function of insoluble G-CSF. To determine what molecular weight species were detected by immunohistochemical staining of MG-63 and SaOS-2 cells, 35S metabolic labeling was performed on cultures grown in the presence of L-ascorbate and β-glycerol phosphate on day 14. Immune-complexes prepared from MG-63 and SaOS-2 lysates but not conditioned medium contained the 28 and 32-kD molecular weight species of G-CSF. Thus, the MG-63 and SaOS-2 osteosarcoma produce membrane-associated G-CSF and GM-CSF under basal conditions, and are capable of producing secreted proteins following LPS stimulation.

These studies show that the intimate physical association between hematopoietic cells and endosteal osteoblasts may exist in part because osteoblasts are constitutive producers of G-CSF as well as mRNAs for other factor(s) which are active on human $CD34^+$ hematopoietic cells. These studies included the non-mineralizing MG-63 and the mineralizing SaOS-2 human osteosarcoma cell lines.

mRNA for the osteoblast-specific protein osteocalcin was well as G-CSF, TGF-$β_1$ and TNF-α was produced by the MG-63 and SaOS-2 cells, in the presence and absence of biochemical signals (L-ascorbate and β-glycerol phosphate) that enhance the osteoblast phenotypic expression from osteoblast committed mesenchymal cells. In contrast, both cell lines expressed c-kit-ligand mRNA only in the absence of such induction. Expression of GM-CSF and IL-6 mRNA appeared to develop in vitro with increasing culture age. In contrast with primary human osteoblasts, no mRNA was detected for LT by RT-PCR over the 18 day culture period.

No IL-3 mRNA was detected in the osteosarcoma cell lines in our culture conditions (Birch et al., 1993), and only the MG-63 cells constitutively produced mRNA for IL-1β. We found that several membrane forms of G-CSF protein including the 28 and 32-kD species are produced, but not the 18 kd species. In addition, GM-CSF was found to associate with cellular membranes.

These two cell lines are useful as models for relatively early (MG-63) and late (SaOS-2) osteoblast development from osteoblasts committed meschymal cells based upon the phenotypic expression of a variety of osteoblastic markers (Majeska et al., 1988). Of particular interest, both the MG-63 and SaOS-2 cell lines expressed c-kit ligand mRNA only in the absence of L-ascorbate and β-glycerol phosphate induction. c-kit ligand is constitutively produced by bone marrow stromal fibroblasts which by itself exhibits little activity but synergizes with many colony stimulating factors (Guba et al., 1992). Once the osteosarcoma were induced however, no message for c-kit-ligand was detected by RT-PCR. The treatment of osteoblast-like cells with L-ascorbate and β-glycerol phosphate promotes the enhanced expression of the osteoblast phenotype including osteocalcin synthesis, alkaline phosphatase activity and extracellular matrix mineralization.

The molecular mechanisms where by these factors promotes mineralization appears to be through the induction of type I collagen cross linking with β-glycerol phosphate acting as an high energy phosphate source (Aronow et al., 1990; Gerstenfeld et al., 1987; and Owen et al., 1990). Therefore, when viewed in the context that the osteoblast phenotype shares "primitive" mesenchymal "fibroblast-like" precursors with bone marrow stromal fibroblasts in the bone marrow, then the loss of c-kit-ligand expression represents a useful marker of osteoblast commitment (Huange et al., 1992).

MG-63 and SaOS-2 also displays G-CSF on their cell membranes as identified by immunohistochemistry which is biologically active as determined by the proliferation of a G-CSF sensitive murine cell line. Using immunoprecipitation of metabolically labeled cells, we showed that two of the three of the known molecular weight species of G-CSF are present in the osteosarcoma cell membranes (Gordon et al., 1993). These were the 28 and 32-kD forms. Under unusual circumstances such as LPS stimulation these cells can secrete G-CSF similar to primary human osteoblasts. Here, soluble G-CSF as detected by ELISA was observed only in the conditioned medium of LPS treated, non-ascorbate and β-glycerol phosphate induced MG-63 cells, but not in conditioned medium of L-ascorbate and β-glycerol phosphate induced cells.

The biologic relevance of these different molecular weight species or secretion patterns is not known, although it appears that the major secreted species is the 18 kD form (Gordon et al., 1993). The higher molecular weight proteins probably represent cell-associated forms or G-CSF protein precursors. Presently only two mRNA species for G-CSF are known by three amino acids which differ (Nagat et al., 1986).

Whether the full length or the truncated mRNA transcripts, or differences in the protein glycosylation are responsible for the diversity of molecular weight forms of G-CSF produced by osteoblasts remains to be determined. Nevertheless the mechanisms regulating the switch from a largely secreted molecule to a membrane-associated form represents an additional marker that can be utilized to delineate an osteoblast commitment from a precursor pool shared with stromal fibroblasts.

Using immunohistochemistry we observed that both osteosarcoma cell lines produce cell-associated GM-CSF but not IL-6. Whether osteoblast-derived cell-associated or matrix bound GM-CSF is biologically active has yet to be determined. These results are not unique for osteoblasts however as stromal cells and endothelial cells produce biologically active matrix/cell-associated forms of c-kit ligand, IL-3, GM-CSF, M-CSF and TGF-β Gordon et al., 1987; Gordon et al., 1993, Roberts et al., 1988; and Gordon et al., 1988).

Bone is unique as a tissue because of its abundance of mineralized extracellular matrix which sequesters many growth factors (Hauschka, 1989). Thus, osteoblasts have a primary role in the bone marrow microenvironment by virtue of their secretion of extracellular matrix which then serves to sequester and present cytokines to be utilized by diverse cell types, in addition to direct production of cytokines.

The significance of cell-cell or cell-to-matrix bound cytokine contact for cytokine presentation to hematopoietic cells in the bone marrow microenvironment is unclear. Immobilization of cytokines on substrates may be a more efficient means for activating signal transduction mechanisms in target cells (Kincade et al., 1987; Citable et al., 1991; Heard et al., 1986; Johnson et al., 1986; and Kittler et al., 1992. In addition, fewer molecules might be needed.

Cell-to-cell contact may also trigger de novo cytokine expression. For example, adhesion of the NFS-60 myeloid leukemia cells to MC3T3-G2/PA6 stromal cells stimulates enhanced stromal cell G-CSF synthesis (Yoshikubo et al., 1994). Lastly, several reports now suggest that cytokines themselves may serve integrin-like activities mediating cell-to-cell adhesion of hematopoietic progenitors to bone marrow stromal cells (Toksoz et al., 1992; Caruana et al., 1993; and Jirillo et al., 1992).

This example shows that two osteosarcoma cell lines, MG-63 and SaOS-2 produces cytokines which are useful for propagating hematopoietic cells.

EXAMPLE 5
HUMAN OSTEOBLASTS SUPPORT HUMAN HEMATOPOIETIC PROGENITOR CELLS IN LONG TERM IN VITRO BONE MARROW CULTURES

The ability of osteoblasts to support the development of hematopoietic colonies from progenitors as well as osteoblasts ability to maintain long term culture initiating cells (LTC-IC) in vitro was examined. The data show that in culture osteoblasts support the maintenance of immature hematopoietic phenotypes. In methylcellulose assays, osteoblasts secrete factors that directly stimulate the development of hematopoietic colonies from progenitor cells and, over a 4 week period, are able to maintain these populations in vitro.

Human osteoblasts and hematopoietic cells were obtained using a modification of methods described in Example 1. Hematopoietic $CD34^+$ cells were seeded directly onto osteocalcin$^+$, c-kit ligand$^-$ confluent osteoblast monolayers at a final density of $1\times10^4$ cells/cm$^2$ for 14 or 28 days in DMEM/F12 (1:1 vol/vol) containing 10% heat inactivated FBS, antibiotics, 10 mM β-glycerol phosphate and 10 mg/ml L-ascorbate. For stromal cell cultures, $CD34^+$ cells were seeded directly onto stromal cells in IMDM medium with 10% FCS, 10% ES, 1 µM hydrocortisone.

Progenitor cell derived differentiation in methylcellulose was used to assay osteoblast-derived activity on progenitors in vitro. $CD34^+$ cells were cultured for 2–4 weeks in the presence or absence of human osteoblasts, whole bone marrow stroma or recombinant IL-3 (10 ng/ml), GM-CSF (20 ng/ml)(Life Technologies), and Erythropoietin (2 units/ml Epo; Stem Cell Technologies, Vancouver, B.S.). Aliquots of recovered hematopoietic progenitors were plated in triplicate-gridded 35 mm dishes (Nunc, Naperville, Ill.) under fully humidified conditions in an atmosphere of 5% $CO_2$ and 5% $O_2$ at 37° C. in 1 ml methylcellulose (Methocult H4330; Stem Cell Technologies) containing IL-3, GM-CSF and Epo. Clonogenic cells were scored at 14 days as CFU-GM, BFU-E, or CFU-GEMM.

The effect of osteoblasts or fibroblast layers on the survival and proliferation of LTC-IC was determined by measuring LTC-IC numbers before and after a two week incubation period. To measure Long Term Culture Initiating Cell (LTC-IC) content, before and after culture, decreasing dilutions (5000, 10130, 500, 100, 50) of bone marrow cells are cultured for 5 weeks on an irradiated (2000 R) bone marrow fibroblast monolayer. After 5 weeks (week 7) each well was harvested, and the cells are replated in colony forming methylcellulose assays. By enumerating each secondary colony assay as "positive" or "negative" for hematopoietic colony growth, a statistical calculation was derived for frequency of cells in the undiluted starting population capable of initiating a (5 week) culture producing progenitor cells. This assay enumerates the most primitive human hematopoietic stem cell yet identifiable by any in vitro culture technique (Sutherland et al., 1990).

As described herein, primary human osteocalcin$^+$, c-kit ligand$^-$ osteoblasts produce G-CSF in an membrane-associated form, as well as several other cytokine mRNAs which have activity on hematopoietic cells. In addition, osteoblasts were capable of stimulating the limited proliferation of human $CD34^+$ human hematopoietic cells in co-culture.

Human $CD34^+$ hematopoietic bone marrow cells were seeded directly onto osteoblast monolayers or in the presence or absence of recombinant G-CSF for two weeks. At the conclusion of the culture period the hematopoietic cells were recovered and prepared for light microscopy. Under these conditions hematopoietic cells grown in the presence of exogenously supplied G-CSF differentiated along the granulocytic pathway into bands/polymorphonuclear neutrophils, while the majority of the hematopoietic cells grown in the absence of G-CSF died. In the presence of osteoblasts however the majority of the recovered hematopoietic cells maintained an immature morphology.

We hypothesized that either the deficient production of c-kit ligand by osteoblasts or the production of TGF-$\beta_1$ by osteoblasts was responsible for the failure of the hematopoietic cells to develop mature phenotypes. Therefore we added either c-kit ligand or neutralizing TGF-$\beta_{1,2,3}$ antibody directly to the osteoblast/hematopoietic cell cultures. Neither the addition of exogenous c-kit ligand (50 µg/ml; Genzyme, Cambridge, Mass.) nor the addition of neutralizing TGF-$\beta_{1,2,3}$ antibody significantly altered the morphology of the hematopoietic cells.

However, the number of hematopoietic cells recovered from the co-cultures was enhanced through the addition of neutralizing TGF-$\beta_{1,2,3}$ antibody. Thus, based upon the morphology of the recovered hematopoietic cells, osteoblasts maintained the immature phenotype of the blood cells that did not appear to be due to the deficient production of c-kit ligand or the production of TGF-$\beta_1$ by osteoblasts.

Human osteoblasts can directly support the development of hematopoietic colonies from $CD34^+$ hematopoietic progenitor cells. For these experiments we directly seeded $CD34^+$ cells onto confluent mixed human bone marrow stroma or osteocalcin$^+$, c-kit ligand$^-$ osteoblast monolayers in methylcellulose in the presence or absence of exogenous cytokines (IL-3, GM-CSF and erythropoietin).

After 2 weeks, hematopoietic colonies were scored as ether CFU-GM, BFU-E or CFU-GEMM by light microscopy. As expected, greater than a 20 fold increase in hematopoietic colonies were formed in the presence of cytokines compared to the number of colonies formed in their absence.

Osteoblast or mixed bone marrow stromal cell monolayers significantly enhanced the formation of colonies over the no cytokine alone controls. The enhanced frequency of colonies developing in the presence of the feeder layers was largely due to an expansion of the CFU-GM compartment, representing 58 (osteoblasts) and 80 (bone marrow stroma) percent of the number of CFU-GMs formed in the cytokine treated control. In the presence of exogenously supplied cytokines, no significant differences were observed between the number of colonies formed by osteoblasts and bone marrow stroma cells.

Thus osteoblasts produce factors that directly stimulate the formation of hematopoietic colonies without the addition of exogenous supplied growth factors, and in the presence of cytokines osteoblasts do not inhibit the formation of hematopoietic colonies as might be expected based upon our morphologic data.

Human osteoblasts can support long-term myelopoiesis in vitro. $CD34^+$ hematopoietic progenitor cells were placed directly onto confluent osteocalcin$^+$, c-kit ligand$^-$ osteoblast monolayers, for one month. At 4 weeks the hematopoietic cells were recovered and placed into a methylcellulose assay to determine the number of colony forming progenitor cells that survived the 4 week treatment. As controls, CD34+ cells were placed into culture in the presence or absence of IL-3, GM-CSF, erythropoietin.

Over the initial 4 week period the number of CFU progenitors increased several fold over input when cultured on osteoblasts. Colony forming activity (CFU) also increased several fold when the hematopoietic cells were cultured in the presence of whole bone marrow stroma or cytokines. No CFU's were recovered from the no-cytokine control groups. Consequently, osteoblasts maintain and/or expand the hematopoietic progenitor pool over a 4 week period in vitro.

To determine whether human osteoblasts can support the maintenance of LTC-IC in vitro, human CD34+ bone marrow progenitors were placed on to homogeneous osteoblast and mixed bone marrow stromal (BMS) cell monolayers, or in the presence or absence of GM-CSF, IL-3 and erythropoietin. Following two weeks of co-culture, the hematopoietic cells were recovered, counted, and assayed for the presence of CFU activity (in methylcellulose) or for LTC-ICs (Limiting dilutional bone marrow cultures).

Over the initial two week period the number of clonogenic progenitors increased several fold over input when cultured on osteoblasts. CFUs also increased several fold when cultured in the presence of whole BMS or cytokines, but none were recovered from the no-cytokine groups. During the same period, a 3–4 fold expansion in the LTC-IC compartment over input occurred in the presence of osteoblasts comparing favorably with BMS. No LTC-IC were recovered from the cytokine control groups. Therefore osteoblasts stimulate the expansion of hematopoietic progenitors while supporting the limited expansion and maintenance of the LTC-IC compartment.

To evaluate whether osteoblasts support hematopoietic stem cells several related assays were employed. In the first assay, colony forming progenitor cells were directly plated on osteoblasts in the presence or absence of stimulating cytokines in methylcellulose. This assay allowed us to directly determine whether factors produced by osteoblasts directly activate the development of hematopoietic colonies from progenitor cells. The majority of colonies formed in the presence of osteoblasts were of the granulocyte/macrophage lineage (CFU-GM). Furthermore, in the presence of differentiating growth factors, osteoblasts do not inhibit the development of the CFU-GM or BFU-E as was expected from our morphologic data that showed hematopoietic cells maintain an immature phenotype in the presence of osteoblasts.

In the second assay, the ability of (colony forming) progenitor cells to survive in liquid culture was determined. When cultured in standard medium, human progenitor cells become undetectable within 72 hours. If progenitor cell stimulating cytokines, such as IL-3, GM-CSF and EPO are added, progenitor cells differentiate over the next two weeks in culture and are therefore unable to form colonies in the methylcellulose assay. Here we found that osteoblasts stimulate an expansion of the progenitor cell population.

To directly determine whether osteoblasts preserve the long term culture initiating cells (LTC-IC) in vitro, we took advantage of the fact that over a five week period on bone marrow stromal cells, hematopoietic cell differentiation is not accompanied by self renewal [10]. As such this assay enumerates the most primitive human hematopoietic stem cell yet identifiable by any in vitro culture technique (Sutherland et al., 1990). Replicates of increasing dilutions of bone marrow cells were cultured for 5 weeks (culture weeks 2–7) on irradiated allogenic bone marrow stromal cell monolayers immediately following a 2 week culture period on osteoblasts.

After 5 weeks on bone marrow stromal cells, each replicate was harvested and replated in colony forming methylcellulose assays (weeks 7–9). By enumerating each secondary colony as "positive" or "negative" for hematopoietic colony growth, a statistical calculation for frequency of cells in the undiluted starting population capable of initiating a culture producing progenitor cells was determined. By these methods it was determined that a 3–4 fold expansion in the LTC-IC compartment over input occurred in the presence of osteoblasts comparing favorably or better with bone marrow stroma.

Therefore osteoblasts stimulate the expansion of hematopoietic progenitors while supporting the limited expansion and maintenance of the LTC-IC compartment. These observations correlate well with the morphologic data showing that in culture osteoblasts support the maintenance of immature hematopoietic phenotypes.

In vivo blood formation takes place within the yolk sac, the liver and the spleen during the early intrauterine period. By the fourth month of fetal life the bone marrow begins to produce blood and from that point on hematopoiesis occurs almost exclusively within bone. Earliest attempts to understand this relationship have focused on a protective function that bone serves for the hematopoietic organ (Trentin, 1989). Although initially promising, more recent data call into question this explanation.

Specifically, during bone marrow transplantation, donor blood stem cells circulate to all body organs but "home" specifically to the bone marrow. When marrow cells lodge in other tissues they may undergo several rounds of division but hematopoiesis is not sustained in these sites (Trentin, 1989 and Tavassoli et al., 1993). Furthermore following the induction of ectopic bone formation in extraskeletal sites functional hematopoietic marrow resides outside the protective confines of the skeleton (Reddi et al., 1981 and Urist et al., 1983) and human fetal bone fragments implanted in immunodeficient scid/scid (SCID) mice sustain active human hematopoiesis (Kyoizumi et al., 1992).

Recently the human bone/blood relationship has been reevaluated in light of the suggestion that osteoblasts are members of the stromal network that supports normal hematopoiesis. The basis for these observations are several fold.

First, isolated human osteoblasts constitutively synthesize mRNAs for G-CSF, GM-CSF, IL-1, LT, TGF-$\beta$, TNF-$\alpha$ (Taichman et al., 1994), as well as LIF and M-CSF (Ohtsuki et al., 1993 and Ohtsuki et al., 1992). Primary murine osteoblasts have been shown to produce several activities that appear to be G-CSF, M-CSF, GM-CSF, IL-1, and IL-6 (Benayahu et al., 1992; Felix et al., 1988; Horrowitz, Coleman, Flood et al., 1989; Hanazawa et al., 1987; Hanazawa et al., 1985; Keeling et al., 1991; and Gowen et al., 1990.

Second, osteoblast-like cells have been observed in long-term in vitro bone marrow stromal dependent cultures which support either limited myelopoiesis (Dexter cultures) or lymphopoiesis (Whitlock-Witte cultures).

Third, stromal cells share several phenotypic characteristics with osteoblasts (Benayahu et al., 1992; Benayhu et al., 1991; Mathieu et al., 1992; Theis et al., 1992; and Dorheim et al., 1993. For example, the murine bone marrow stromal cell lines BMS2 and +/+2.4, express high levels of alkaline phosphatase enzyme activity, collagen (I) and bone sialoprotein expression (Dorheim et al., 1993).

In addition, mRNA for osteocalcin, an osteoblast specific protein has been detected in stromal cell lines. In fact, many stromal cell lines possess some osteoblastic features, but differ mainly in the degree of expression (Benayahu et al., 1992 and Benayahu et al., 1991).

Lastly, recent data suggest that osteoblasts and stromal cells are derived from a common stem cell at least in fetal human marrow as $CD34^+,HLA^-DR^-CD38^-$ cells can be induced to form either osteoblasts, stroma or hematopoietic cells. In fact, recombinant bone morphogenic protein-2 has been shown to induce osteoblastic differentiation in the W-20-17 murine stromal cell line (Theis et al., 1992), and considerable efforts are now directed at obtaining osteoprogenitor cells from murine and human bone marrow (Long et al., 1990).

This example shows that primary human osteocalcin$^+$ c-kit ligand$^-$ osteoblasts support the limited expansion of $CD34^+$ human hematopoietic progenitors over a two week period in vitro. Furthermore in Wright-Geimsa cytospin preparations many of the hematopoietic cells recovered after the co-culture maintained an immature morphology showing that osteoblasts are able to maintain the progenitors in an immature state. The mechanisms whereby osteoblasts maintain the immature morphology of the hematopoietic cells is likely to be due the production of maturation inhibitors or by the failure of osteoblasts to produce all the maturation factors required for terminal progenitor differentiation, or possibly both. At least in part, the limited expansion of $CD34^+$ cells is due to secreted or cell bound cytokines. Osteoblasts make a membrane form of G-CSF and express mRNA for IL-6, GM-CSF, TNF-$\alpha$, TNF-$\beta$(LT), TGF-$\beta_1$ but not c-kit ligand or IL-3.

EXAMPLE 6
PRODUCTION OF COLONY STIMULATION FACTORS BY OSTEOBLASTS

Primary human osteoblasts are obtained either from outgrowths of bone explants or from serum free cultures of non-adherent low density marrow progenitors. The osteoblast phenotype are verified by a two step screening method. The primary screening method utilizes RT-PCR to verify the presence of osteoblasts (BSP$^+$ and osteocalcin$^+$) and to screen for contaminating marrow fibroblasts (c-kit ligand$^+$). The secondary screening procedures of representative samples verifies the osteoblast phenotype by functional and morphological assays including the following criteria: expression of alkaline phosphatase, osteocalcin, collagen (type I), osteonectin, osteopontin, high cyclic AMP responsiveness to PTH and mineralization of extracellular matrix. In addition, the osteoblast cultures are c-kit ligand$^-$, osteocalcin$^+$, express alkaline phosphatase, collagen (type I), have a high cAMP responsiveness to PTH and mineralize their extracellular matrix (Sutherland et al., 1990). The pattern of cytokine expression in purified resting osteoblast is determined. Expression of these cytokines are determined at the transcriptional level by RT-PCR and Northern hybridization analysis, and at the post-translational level by ELISA and Western Blot analysis.

Normal human bone is obtained from otherwise healthy patients undergoing knee or hip replacement. Osteoblasts are obtained by modifications of methods described in Robey and Termine (Robey et al., 1985). Trabecular bone is removed by scraping the surfaces with a bone curette, washed extensively, and ground in a BioComp Minimill (W. Lorenz, Jacksonville, Fla.) to produce a uniform particle size of (size$\leq 1$ cm$^2$) and incubated in 1:1 mixture of Ham's F12/Dulbeco's minimum essential medium (F12/DMEM) containing 1 mg/ml bacterial collagenase (Type P, Boehringer Mannheim Biologicals, Indianapolis, Ind.) and placed into T225-tissue culture flasks (Costar).

Cells from the treated chips migrate onto the tissue culture plastic after 1–2 weeks, and after another 2 weeks become confluent. Cultures are maintained in 1:1 mixture F12/DMEM medium with low $Ca^{+2}$ and 10% fetal bovine serum. Several assays are used verify the maturity of the osteoblasts obtained; in vitro mineralization, expression of alkaline phosphatase, and osteocalcin synthesis using commercially available reagents and methods described in (Taichman and Hauschka, 1992). Northern hybridization analysis is performed using cDNA probes for osteocalcin, BSP, type I collagen.

To assure that these investigations are representative of normal human osteoblast physiology, primary human osteoblasts can be obtained from other sources utilizing a modification of Long et al (Long et al., 1990 and Campell et al., 1987). Bone marrow cells are obtained from healthy adult volunteers by iliac crest puncture and aspiration. The tissue is collected in preservative-free heparin and PBS after informed consent is obtained. The bone marrow cells are layered on Ficoll-Hypaque (specific gravity 1.077) and separated by centrifugation at 1000×g.

Mononuclear cells are aspirated from the medium-Ficoll interface and adherence depleted by two rounds of plastic incubation at 37° C. for one hour each in IMDM medium with 20% fetal bovine serum. This procedure removes monocytes, platelets, and megakaryocytes and the non-adherent cells are recovered (53,54). The non-adherent low density cells are cultured in serum-free McCoy's 5A medium (GIBCO, Grand Island, N.Y.) supplemented with 1% ITS-plus (insulin, transferrin, selenious acid, BSA, linoleic acid; Collaborative Research, Bedford, Mass.) and 20 pg/ml TGF-$\beta_1$ (Collaborative Research) at a density of $5\times10^{10}$ cells/ml/cm$^2$ in multiwell tissue culture plates (Costar) for 7 days at 37° C. in 5% $CO_2$. The osteoblasts are removed by 0.5% Trypsin-EDTA and replated in McCoy's 5A medium containing 10% (v/v) FBS, 10 mM $\beta$-glycerophosphate, 10 mg/ml L-ascorbate and antibiotics.

Total cellular RNA is recovered from osteoblasts by the methods of Chomczynski and Sacchi (Chomcynski et al., 1987). Cells are suspended in GITC solution (final concentrations are 4M guanidine isothiocyanate, 0.5% sarcosyl, 25 mM citric acid, pH 7.0 and 0.007% $\beta$-mercaptoethanol then sequentially mixed with 3M sodium acetate, (pH 4.0), 1 vol phenol, and 1/10 vol 49:1 chloroform:isoamyl alcohol. The aqueous layer is collected and precipitated at −20° C. in isopropanol. The RNA is reprecipitated in equal volumes of GITC solution and isopropanol, dried, and resuspended in RNAse-free water. RNA quantity and integrity is checked with gel electrophoresis with ethidium bromide and absorbance at $A_{260}/A_{280}$.

The primers to be utilized in these investigations are as follows:

TABLE 6

| Protein | Nuc | Direction | Oligonucleotides |
|---------|-----|-----------|------------------|
| β-Actin | 430–447 | S | CAGCCATGTACGTTGCTA (SEQ ID NO:25:) |
|         | 666–683 | AS | GGATCCAATACGACTCACTATAGGCTCCGAGGAATTACAGTGCGTG (SEQ ID NO: 26:) |
| IL-1β   | 142–164 | S | ATCCAGCTACGAATCTCCGAC (SEQ ID NO: 27:) |
|         | 544–564 | AS | GTGCGTCCTGTCCATGTCTAA (SEQ ID NO: 28:) |

TABLE 6-continued

| Protein | Nuc | Direction | Oligonucleotides |
|---|---|---|---|
| IL-3 | 90–120 | S | GGATCCTTGAAGACAAGCTGGGTTAACTGCTCTAAC (SEQ ID NO: 5:) |
|  | 339–368 | AS | AAGCTTGATATGGATTGGATGTCGCGTGGGTGC (SEQ ID NO: 6:) |
| IL-6 | 26–53 | S | GGATCCTCCTTCTCCACAAGCGCCTTCGGTCCA (SEQ ID NO: 7:) |
|  | 421–450 | AS | AAGCTTGTTCCTCACTACTCTCAAATCTGTTCTG (SEQ ID NO: 8:) |
| G-GSF | 95–115 | S | CACAGTGCACTCTGGACAGTGCAGGAA (SEQ ID NO: 11:) |
|  | 480–510 | AS | CATTCCCAGTTCTTCCATCTGCTGCCAGAT (SEQ ID NO: 12:) |
| GM-CSF | 100–124 | S | GAGCATGTGAATGCCATCCAGGAG (SEQ ID NO: 13:) |
|  | 415–442 | AS | CTCCTGGACTGGCTCCCAGCAGTCAAA (SEQ ID NO: 14:) |
| c-kit-ligand | 258–282 | S | GAAGGGATCTGCAGGAATCGTGTG (SEQ ID NO: 23:) |
|  | 899–923 | AS | GCCCTTGTAAGACCTGGCTGTCTC (SEQ ID NO: 24:) |
| LT | 210–232 | S | TGTTGGCCTCACACCTTCAGCTG (SEQ ID NO: 21:) |
|  | 612–638 | AS | ATCTGTGTGGGTGGATAGCTGGTCT (SEQ ID NO: 22:) |
| Osteocalcin | 1046–1066 | S | GGCAGCGAGGTAGTGAAGAG (SEQ ID NO: 15:) |
|  | 1364–1384 | AS | GATGTGGTCAGCCAACTCGT (SEQ ID NO: 16:) |
| TGF-β¹ | 1658–1684 | S | ACCACTGCCGCACAACTCCGGTGAC (SEQ ID NO: 17:) |
|  | 1901–1926 | AS | ATCTATGACAAGTTCAAGCAGAGTA (SEQ ID NO:18:) |
| TNF-α | 382–405 | S | GCAGTAAGATCATCTTCTCGAACC (SEQ ID NO: 19:) |
|  | 725–746 | AS | CAGATAGATGGGCTCATACCA (SEQ ID NO: 20:) |

RNA, 1.0 μg, 10X RT buffer (1X RT buffer consists of 50 mM Tris, pH 8.3, 50 mM KCL, 8.0 mM $MgCl_2$, and 10 mM dithiothreitol), 25 mM dXTP mix (25 mM of each dXTP [ACGT]), 3.0 μg oligo d(T), and 2.5 U reverse transcriptase (AMV-Reverse Transcriptase, GIBCO-BRL, Gathersburg, Md.) are incubated at 42° C. for one hour. One-fifth of the double stranded product is mixed with 10X Taq/RT buffer (1X Taq/RT buffer consists of 10 mM Tris, pH 8.3, 50 mM KCl, 1.5 mM $MgCl_2$, 0.01% gelatin, and 2.0 mmol. L dithiothreitol), 1 mM dXTP mix, 500 ng each of the sense and antisense oligonucleotides of interest, and 2.5 U Taq polymerase (AmpliTaq DNA polymerase; Perkin Elmer Cetus, Norwalk, Conn.).

The reaction mixture is subjected to thermal cycling at 94° C. for 1 min and 72° C. of 3 minutes for 35 cycles, then finally a 10-minute extension at 72° C. (Perkin Elmer Cetus DNA thermal cycler). PCR products are electrophoresed in 3% agarose and visualized using ethidium bromide. The bands of the sizes expected for the primers used are 85P, 292 nt; IL-12, 668 nt; IL-3, 279 nt; IL-6, 398 nt; IFN-8, 247 nt; G-CSF, 415 nt; GM-CSF, 332 nt; osteocalcin, 137 nt; TFG-$β_1$; 268 nt; TNF-2, 382 nt; TBF-β, 447 nt.

As positive and negative controls for the reverse transcriptase and polymerase chain reactions, we will either omit or include RNA from specimens in which the mRNA of interest is known to be expressed including: IL-1α stimulated human bone marrow stroma (c-kit ligand, G-CSF, GM-CSF, TNF-α,β) or peripheral blood lymphocytes stimulated with PHA (3.0 μg/ml) and PMA (3 ng/ml) for 18 hours (TNF-α,β), G-CSF, GM-CSF, IL-3, IFN-Γ). To control for false positives due to "overamplification" or DNA contamination, IFN-gamma primers is prepared as only T-lymphocytes are known to express IFN-Γ message (Metcalf, 1988).

To determine in vitro mineralization, the osteoblast cultures are maintained essentially as previously described. Cultures are fixed in 10% normal buffered formalin for three hours. Following fixation the cells are stained using the Von Kossa technique for bound phosphate using 5% (w/v) silver nitrate in PBS. The black nodules are counted and identified under a dissecting microscope (10X).

Alkaline phosphatase is an enzyme that has been associated with an osteoblast phenotype. Several possible activities in bone have been proposed. These include regulation of cell division, removal of inhibitors of crystal growth, transportation of phosphate and a possible role as a calcium binding protein (Wutier et al., 1988). As a marker of the osteoblast phenotype, alkaline phosphatase content is a useful second parameter for monitoring osteoblast maturational status, as it is not always linked with osteocalcin synthesis.

Assays for alkaline phosphatase activity are performed using a modification of the method of Reddi and Huggins (Reddi et al., 1972). P-nitrophenylphosphate (Sigma) is used as a substrate, and the activity is read at an absorbance of 400 nm. The results are expressed in units of enzyme activity based upon levels of p-nitrophenol generated from the substrate in a given amount of time per μg of DNA. Appropriate dilutions are prepared in assay buffer (0.15M NaCl, 3 mM $NaHCO_3$, pH 7.4) Standard p-nitrophenol (Sigma) solutions are prepared by dissolving stock solutions in buffer. To 10 μl of diluted sample, blank (buffer), standard, 70 μl of 0.1 M Na barbital pH 9.4, and 20 μl of 0.025M PNPP (PNPP, Sigma phosphatase substrate) are added. All plates are incubated for 15 minutes at 37° C. Following the incubation period, the reactions are stopped with 100 μl of 0.1M NaOH.

Histochemistry for alkaline phosphatase is performed on osteoblasts grown in Lab-Tec tissue culture chambers (Miles Laboratories Inc., Naperville, Ill.) with a commercially available staining kit (Sigma).

Cyclic AMP (cAMP) levels in osteoblast monolayers are determined using a rapid and specific assay kit based upon the competition between unlabeled cAMP and a known quantity of labeled cAMP binding to a protein which has high specificity and affinity for cAMP (Amersham Corp., Arlington heights, Ill.). Quantification is measured in a competitive radioimmunoassay where the amount of labeled cAMP-protein complex formed is inversely proportional to the concentration of unlabeled cAMP in the assay sample. Osteoblasts are removed from culture, and washed with warm PBS without calcium and magnesium. Warm media containing recombinant human (1–34) PTH (Boheringer Mannheim) in medium with 1% BSA, β-glycerophosphate and L-ascorbate is added. The cultures are incubated for 0.5–5 minutes at 37° C. in 5% $CO_2$. Following the incubation period the culture medium is removed and the cells are washed (3 times) in ice cold PBS. The cell layers are scraped into 2.0 ml centrifuge tubes and prepared for cAMP enumeration following the directions of a commercial kit (Amersham).

Investigations of Transcription of osteoblast-derived cytokines determines i) if mature protein is synthesized from the RNA transcripts, and ii) the rate at which the protein is produced and consumed in culture.

ELISAs are performed using the double-antibody sandwich method, using commercially available kits. The cytokines to be tested include IL-1, IL-3, IL-6, G-CSF, GM-CSF, c-kit ligand, TGF-$\beta_1$ (R+D Systems) and the osteoblast specific protein osteocalcin (Metra BioSystems, Palo Alto, Calif.). Based upon parallel assays of known diluted standards, the sensitivities of the assays using unconcentrated medium are as follows:IL-3 30 to 2,000 pg/mL, IL-6, 30 to 2000 pg/mL, G-CSF 25 to 2,000 pg/mL, GM-CSF 2 to 500 pg/mL. Used in conjunction with concentrated medium, these assays detect concentrations as low as: IL-3, 3 pg/mL; IL-6, 3 pg/mL, G-CSF 4 pg/mL, GM-CSF 200 fg/mL. To determine whether supernatant concentration substantially alters the ELISA results, control experiments are performed in which known standards were concentrated and reassayed. In these experiments, preconcentration and postconcentration sample assays gave similar results ±15%.

The cDNA probes for osteocalcin, collagen (Type I$\alpha$), BSP, osteonectin, osteopontin, IL-3, and GM-CSF are prepared from random hexanucleotide labeling with $^{32}$P-dCTP of gene specific inserts (25ng). The GM-CSF probe is a 700-bp EcoRI-HindIII fragment. IL-3 probe is a 1.0-kb Xho I cDNA fragment. Synthetic oligonucleotides for G-CSF, IL-6, and TGF-$\beta_1$ are endlabeled using polynucleotide kinase and 32P-gATP (Felix et al., 1991).

Experiments using RT-PCR indicate that message for G-CSF as well as other cytokines are expressed by human osteoblasts. In order to quantitate the steady state levels of cytokine message produced, Northern hybridization analysis is performed using $^{32}$P-labeled cDNAs to detect mRNA immobilized on nitrocellulose to i) validate the PCR results ii) quantify the relative levels of cytokine mRNA (as well as type I collagen, osteocalcin, BSP) and iii) explore whether the control of cytokine synthesis by osteoblasts is at the level of transcription or translation. Total cellular RNA is quantified by absorption $A_{260}/A_{280}$, the probes are labeled with $^{32}$P-dCTP by the random primer method of Feinberg and Vogelstein (Broxmeyer et al., 1986 and Feinberg et al., 1984).

The blots are prehybridized and hybridized in 50% formamide, 0.25M NaHPO$_4$, 0.25M NaCl, 7% sodium dodecyl sulfate (SDS) (w/v) and 1 mM EDTA at 45° C. At the completion of the hybridization the membranes are washed in the following solutions; 2X SSC/0.1% SDS, 0.5X SSC/0.1% SDS, 0.1X SSC/0.1% SDS (65° C.) (two 30 minute washes each) and prepared for auto radiography. Auto radiographic signals are quantified relative to actin controls (American Tissue Type Collection, Rockville, Md.) by scanning laser densitometry (LKB Ultrascan). Peripheral blood mononuclear cell or RNA and bone marrow stromal cells are utilized for cytokine positive controls. RNAase protection assays can be performed if these assays do not prove sufficiently sensitive.

Validation of the RT-PCR products present in agarose gels is preformed by alkaline Southern blot analysis. The DNA gels are transferred to nylon (Zeta-Probe blotting membranes: Biorad, Richmond, Calif.) in 0.4 mol/L NaOH, and then hybridized with the appropriate $^{32}$P-labeled cDNAs. Hybridization with cDNA probes is performed in final concentrations of 6X standard saline citrate (SSC; 1X SSC is 0.15 mM NaCl and 0.015 mM sodium citrate), 0.5% blotto, 0.1% SDS, 0.01 mM EDTA, and 100 mg/ml denatured sonicated salmon sperm DNA and probed with the appropriate $^{32}$P-labeled cDNAs. Alternatively, hybridization of immobilized DNA with oligonucleotide DNA probes is performed in final concentrations of 6X NET (1X NET is 0.14 mol/L NaCl, 15 mM tris, pH 8.0 and 1.0 mM EDTA) 10X Denhardt's solution, and 1% SDS.

Osteoblast conditioned media is prepared as follows. Primary osteoblasts are removed by trypsin and replated at a density of 1×10$^5$ cells/cm$^2$ in multiwell tissue culture plates (Costar) for 14 days in calcium replete DMEM/F12 (1:1 vol/vol) medium containing 10% heat inactivated FBS, antibiotics, 10 mM $\beta$-glycerophosphate and 10 mg/ml L-ascorbate. In some cases 1% ITS can be substituted for the serum to evaluate the effects of serum on cytokine synthesis. The conditioned media is collected and the cell layers are washed in HBSS and fresh medium is added back to the cells for an additional 1–7 days. In some cases, osteoblasts are treated with 25 µg/ml E. coli LPS (Sigma Chemical Corp) for the final six to 24 hours of culture.

Aliquots of conditioned medium is concentrated 4–10 fold by centrifugation at 1,000 g in a 25° C. fixed angle JA-17 rotor (Beckman, Palo Alto, Calif.) in Centricon-10 concentrators (Amicon Division of W. R. Grace and Co, Danvers, Mass.) until the desired volume is reached.

To determine whether osteoblasts present cytokines on their cell membranes to hematopoietic progenitors, indirect immunohistochemistry phase-contrast microscopy is performed. Paraformaldehyde-fixed primary human osteoblasts grown in 96-well tissue culture plates is incubated with monoclonal antibodies incubated at 4° C. for two hours or isotype matched control. Detection is accomplished using a FITC-conjugated antiserum. All reagents are commercially available.

As an alternative to the immunohistochemistry approach for determining whether osteoblast-derived cytokines are present in the matrix/cell layers, two step Westerns are performed. Osteoblasts are washed in PBS and lysed in ice-cold lysis buffer (1% NP-40, 10 mM Tris (pH 7.6), 50 mM NaF, 100 mM NaCl, 1 mM phenylmethylsulfonyl fluoride, 0.23 U/ml aprotinin, 10 µg/ml leupeptin, 10 µM pepstatin, 1 mM sodium orthovanadate) at 4° C. for 10 min. Nuclei and cellular debris are removed by centrifugation at 16,000×g for 15 min at 4° C.

Lysates normalized for either cell numbers or total protein and are incubated antibodies specific for the cytokine of interest. Immune complexes are collected using fixed *Staphyloceus aureus* (Pansorbin$^R$, Calbiochem. LaJolla, Calif.) that are preincubated with lysis buffer containing 1% nonfat dry milk. In some cases, recombinant cytokine (10 µg) is included to verify the specificity of antibodies. Immunoprecipitates are washed, eluted into 2X laemmli buffer, electrophoresed in polyacrylamide gels, and transferred to nitrocellulose. Blots are preblocked with 4% bovine serum albumin (BSA).

After extensive washes the blots are incubated for 12 hours in a 1/50 (v/v) dilution of the goat antihuman cytokine specific antiserum (available through commercial sources), washed 4-times, and preblocked again prior to incubation for 90 minutes with 200 µg/ml of 133 µg/ml horseradish peroxidase(HRP)-conjugated Rabbit anti-goat molecule IgG (Sigma, St. Louis, Mo.). Final detection will accomplished by the emission chemiluminescence luciferase (ECL) method using a kit from Amersham, Inc. (Arlington Heights, Ill.).

Previous work on fetal rat calvaria osteoblasts suggests a sequential developmental pattern of gene expression by osteoblasts (Aronow et al., 1990; Gerstenfeld et al., 1987; and Owen et al., 1990). If tumor lines represent alterations in osteoblast maturation, then our data shows that even relatively "immature" osteoblasts constitutively produce G-CSF, while "mature" osteosarcoma lose the ability to synthesize c-kit ligand. Based upon the known orderly pattern of gene expression by maturing osteoblasts questions are raised: i) When do the various cytokine messages first appear in the progressive maturation of osteoblast to osteocytes? ii) Do stage-specific changes in protein composition of the extracellular matrix parallel the modifications in cytokine gene expression?

Cytokine synthesis during the three key periods of osteoblast maturation as defined by the temporal pattern of osteoblast specific gene expression is compared. In culture, these include an i) initial burst of proliferative activity characterized cell cycle genes and growth gene expression (i.e. Histone H1), ii) decline of the proliferative activity with the initial expression of genes encoding alkaline phosphatase and non-collagenous bone associated proteins, and finally iii) increased expression of osteoblast specific proteins with the onset of mineralization. The following gene markers; osteocalcin, osteonectin, osteopontin, BSP and collagen (Type I) synthesis are examined. Functional assays include examinations of mineralization, cAMP responsiveness, alkaline phosphatase activity and proliferation.

Statistical evaluation of the main values calculated from proliferation assays, alkaline phosphatase, cAMP levels, in vitro mineralization, and ELISA values are performed by analysis of variance using the paired student's t test. Densitometric evaluation are performed for the Northern, Western and Southern apoptosis investigations.

EXAMPLE 7
PROPAGATION OF PRIMITIVE HEMATOPOIETIC STEM CELLS AND THEIR PROGENITORS BY OSTEOBLASTS

Primary human osteoblasts obtained either from outgrowths of bone explants or from serum free cultures of marrow progenitors are utilized in a combination of co-culture and molecular biological approaches to determine whether cytokines derived from osteoblasts influence hematopoietic stem cell survival, proliferation and maturation, based upon identification of osteoblast derived cytokines of Example 6.

The effects of osteoblasts on the survival and proliferation of primary hematopoietic CD34$^+$ human stem cells and factor dependent cell lines in co-culture and methylcellulose assays are characterized. The influence of osteoblasts on the prevention of apoptotic cell death of primitive human stem cells by examining DNA fragmentation into integer-multiples of the internucleosomal distance is determined.

Bone marrow cells obtained from healthy adult volunteers are diluted 1:4 in IMDM and separated by density separation on Ficcol-Hypaque (specific gravity 1.077) to recover mononuclear cells. Following two rounds of plastic adherence at 37° C. for one hour each in IMDM medium with 20% FBS to remove monocytes, platelets and megakaryocytes, the non-adherent cells are recovered and CD34$^+$ hematopoietic progenitor populations are isolated utilizing a commercially available disposable separation system using an avidin-biotin immunoaffinity process which can process $25-500\times10^6$ cells (CellPro Inc., Bothwell, Wash.).

CD34$^+$ or NFS-60 cells are placed in co-culture with osteocalcin$^+$, c-kit ligand$^-$ confluent osteoblast monolayers in 24-well TransWell$^R$ tissue culture plates at a final density of $1\times10^4$ cells/well (Costar) and incubated for 3-14 days. For investigations of the role of G-CSF in CD34$^+$ stem cell proliferation as an representative example, where appropriate i) vehicle, ii) 10 µg/well of an affinity purified IgG fraction of neutralizing goat anti-human G-CSF serum (R+D Systems), or 10 µg/well of normal goat IgG serum are added to quadruplicate cultures daily. c-kit ligand (50 ng/ml) can also be added to the cultures. The rational for this strategy is that as osteoblasts do not appear to produce this factor, which by itself has no known biologic activity, we may be able to amplify the cytokine signal to detectable levels by synergy. Absolute cell numbers are determined by manual hemocytometer counting in PBS containing 0.4% trypan blue (Sigma).

The growth factors used in these studies are recombinant proteins, with the exception of WEHI-3 cell conditioned medium for maintenance of the NFS-60 cells. The other factors included in methyl cellulose colony assays include rhGM-CSF, (Amgen, Thousand Oaks, Calif.), rhIL-3 (Genetics Institute, Cambridge Mass.), Erythropoietin (EPO, Terry Fox Labs, Vancouver, Canada), c-kit ligand (GIBCO BRL, Grand Island, N.Y.). and rhG-CSF as a positive control for colony growth (Amgen).

Colony growth in methylcellulose is utilized to determine if osteoblasts are functionally competent in maintaining hematopoietic progenitors in vitro. To determine the original size of progenitor forming population in the column isolated marrow, CD34$^+$ cells ($5\times10^4$/ml methylcellulose) are inoculated in colony assay medium (Terry Fox Laboratories, Vancouver, BC) containing 0.9% methylcellulose, 30% FBS, 1% bovine serum albumin, 100 µM β-mercaptoethanol to which 2 mM glutamine, 5 ng/ml rhGM-CSF, 100 ng/ml rh c-kit ligand, and 2 U/ml rh Epo is added.

Aliquots of 1 ml are plated in triplicate-gridded 35 mm dishes (Nunc, Naperville, Ill.) under fully humidified conditions in an atmosphere of 5% $CO_2$ and 5% $O_2$ in $N_2$ for at 37° C. Colonies of greater than 50 cells are scored with a darkfield stereo microscope (Nikon, Garden City, N.Y.) for CFU-GM and BFU-E colonies. After 14 days in the absence of either exogenous cytokines or stromal cells, no hematopoietic progenitors are recovered from liquid culture (Emerson et al., 1989). To determine the effects of osteoblast co-culture on the survival of CD34$^+$ hematopoietic progenitor populations, CD34$^+$ cells are recovered from the various experimental treatments, normalized for cell number and inoculated into the methyl cellulose assay and scored for colony growth. For morphologic studies, cytospin preparations are made from individual colonies and stained with Wright-Giemsa stain (Sigma).

Two related assays are employed to study the ability of osteoblasts and osteoblast-derived supernatants to support the survival of primitive human hematopoietic cells. In the first assay, the ability of (colony forming) progenitor cells to survive in liquid culture is assayed. When cultured in standard medium ±serum (the typical standard is IMDM +10% FCS +10% HS), human hematopoietic cells become undetectable within 72 hours. If progenitor cell stimulating cytokines, such as IL-3 or GM-CSF, are added, progenitor cells differentiate over the next two weeks in culture. However, under these typical culture conditions, this differentiation is not accompanied by self renewal, so that the numbers of progenitor cells remaining after 14 days declines (Sutherland et al., 1990). Therefore, maintenance of clonogenic cells (CFU-GM, BRU-E, CFU-GEMM) over 14 days in osteoblast cultures is evidence for their secretion of a novel cytokine.

In the second assay system, maintenance of long term culture initiating cells (LTCIC) is measured. In these assays, 20 replicates of decreasing dilutions (10,000, 5000, 1000, 500, 100, 50) of bone marrow cells are cultured for 5 weeks on an irradiated (2000 R) bone marrow fibroblast monolayer. After 5 weeks each well is harvested, and the cells are replated in colony forming methylcellulose assays. By enumerating each secondary colony assay as "positive" or "negative" for hematopoietic colony growth, a statistical calculation is derived for frequency of cells in the undiluted starting population capable of initiating a (5 week) culture producing progenitor cells. This assay enumerates the most primitive human hematopoietic stem cell yet identifiable by any in vitro culture technique (Sutherland et al., 1990).

When human hematopoietic cells, either as whole bone marrow populations or isolated enriched CD34$^+$ cell populations, are incubated either alone or in the presence of any of the known hematopoietic growth factors, cells capable of initiating these long term liquid cultures (LTCICs) decline after as little as 4–5 days. In addition, the presence of a fibroblast feeder layer does not prevent this decline.

Withdrawal of cytokines from factor-dependent NFS-60 and CD34$^+$ cells has been reported to result in cell death through induction of apoptosis (Duke et al., 1986). This form of cell death is an active process typically requiring new RNA and protein synthesis, and culminates in the activation of endogenous endonuclease that fragment nuclear DNA into integer-multiples of the internucleosomal distance (Wyllie et al., 1984). To determine if the relative levels of DNA-fragmentation in these cells in the presence or absence of osteoblasts in which neutralizing cytokines or control antibodies is included is characterized. DNA from equal numbers of viable cells are size-fractionated by gel-electrophoresis and stained with ethidium bromide, and examined for a characteristic ladder of DNA bands representing integer-multiples of ~180 base pairs.

NFS-60 and CD34$^+$ cells grown in either the presence or absence of osteoblast cell layers are recovered on days 0, 3, 6, 9, 12 and 14 days from after culture initiation by trypsinization and washed twice in PBS and are resuspended in 15 µl of a buffer containing 15% Ficoll, 10 mg/ml boiled ribonuclease-A, and 0.01% (w/v) bromophenol blue in TBE electrophoresis buffer (89 mM Tris [pH 8.0], 89 mM Boric acid, 2.5 mM EDTA).

Cell lysates are stored at −80° C. until analysis of the cellular DNA by a gel-electrophoresis method that minimizes sample handling and manipulations by performing SDS and proteinase K treatments directly in the agarose gels (Feinberg et al., 1984). Briefly, 100 ml 2% agarose gels containing TBE buffer is prepared in 11 cm×14 cm supports. The area above the gel-comb (1 cm) is removed and this space is filled with TBE containing 0.8% agarose, 1.25 mg/ml proteinase K, and 2% SDS. Cell samples (15 µl ) are transferred to the wells of these gels and electrophoresis is performed at 20 volts for 1 hour, followed by 90 volts for 3 hours. After electrophoresis, gels are gently agitated overnight in TE buffer (10 mM Tris, 1 mM EDTA [pH 8.0] containing 20 µg/ml RNAse-A and stained with 5 µg/ml ethidium bromide for 30 mins. Gels are destained in water for 4 hours prior to photographing with UV-transillumination. Freezing of the samples prior to analysis does not alter the results.

For morphologic studies, cytospin preparations of CD34$^+$-ostcoblast co-cultures or CD34$^+$ colonies plucked from methylcellulose are and stained with Wright-Giemsa stain (Sigma).

EXAMPLE 8
OSTEOBLAST—HEMATOPOIETIC CELL INTERACTIONS

The observation that hematopoiesis occurs in close physical association with stromal bone marrow elements suggests that adhesion plays an important role in hematopoiesis (Simons et al., 1994). Indeed it now appears that intimate contact between hematopoietic cells and stromal cells is mediated by multiple, receptor-ligand events by cell adhesion molecules (CAMs) representing three adhesion superfamilies (integrins, selectins, immunoglobin supergene family). The microenvironment that is provided by the osteoblasts includes cell-cell contact and the adhesion molecules. These adhesive interactions are largely dependent upon alpha 4 beta 1 integrin expressed on the CD34 cells and VCAM-1 expressed by bone marrow stroma (reviewed in (Simons et al., 1994; Coombe et al., 1994; and Simmons et al., 1992). In addition, the extracellular matrix produced by stromal cells may mediate stem cell adhesion. Glycosaminoglycans such as heparin and heparin sulfate (Coombe et al., 1994) as well as other molecules including thrombospondin (Simmons et al., 1992), fibronectin and hemonectin (Campell et al., 1987) bind stem cells through beta 2 integrin, Mac-1, and CD45 receptors (Coombe et al., 1994). These events are regulated by cytokines and show marked heterogeneity in patients with myeloproliferative disorders illustrating that defective stromal cell adhesion may be important in clinical settings (Dittel et al., 1993 and Dowding et al., 1991).

It is likely that osteoblasts and osteoblast's extracellular matrix participate in hematopoiesis through similar adhesive events. In fact, we have observed a tight attachment of CD34$^+$ cells to osteoblasts in vitro. There is little doubt that osteoblasts regulate the attachment of osteoblasts to the bone mineralized substratum (Fuller et al., 1991). Apart from these interactions between osteoblasts and osteoblasts, however, nothing is known with regard to adhesive events between osteoblasts with other members of the hematopoietic system.

At present, the identities of all of the molecule(s) responsible for the maintenance and expansion of hematopoietic progenitors in culture is not known. It is likely that unique osteoblast-derived cytokines are involved. In addition, the CD34$^+$ cells become tightly adherent to osteoblasts in co-culture. Specific ligand-receptor interactions are likely responsible for the adhesive activity between CD34$^+$ cells and osteoblasts. These two observations combined, suggest that stem cell self renewal is influenced by either osteoblast-derived cytokines or adhesive interactions between the two cell types or possibly both.

As discussed above, osteoblasts stimulate the proliferation of CD34$^+$ and NFS-60 cells in co-culture, but osteoblast-conditioned medium does not appear to contain the same activity. Co-culture of CD34$^+$ cells with bone marrow stromal cells also stimulates CD34$^+$ cell proliferation. Like the osteoblast-derived activity, however, the stromal cell activity also is not detected in unconcentrated conditioned medium. Verfaillie et al recently found that soluble factor(s) produced by human marrow stroma that are undetected in unconcentrated conditioned medium induce the proliferation of hematopoietic cells when they are separated from stroma by a microporous membrane. These results suggest that stromal cell dependent hematopoiesis, at least in part, depends on short-lived soluble factors that require high local concentrations, or are present in conditioned medium below the level of detection (Verfaillie, 1992).

To determine if the osteoblast-derived factor(s) also requires high local concentrations to stimulate proliferation CD34$^+$ cells were co-cultured with osteoblasts but separated the blood cells from the osteoblasts by a porous membrane (TransWell$^R$, Costar). Over a two week period osteoblasts produce soluble factor(s) which pass through porous membranes to support the survival of hematopoietic cells. CD34+ bone marrow cells ($8\times10^4$) or NFS-60 ($1\times10^4$) were seeded into the top chamber of TransWell$^R$ (Costar) dual chambered 24 well plates (3 µM pore size) with confluent primary human osteoblasts (HOB) or MG-63 or SaOS-2 osteosarcoma cells in the bottom chamber. At 4 (B) and 14 (A) days, absolute hematopoietic cell numbers were determined by manual hemocytometer counting. In this system proliferation of the CD34+ cells comparable with what occurs during direct osteoblast-CD34+ cell contact has not been observed. However, NFS-60 cells co-cultured with primary human osteoblasts do proliferate in this dual chamber culture system. These results show that at least some osteoblast-derived activities do not require cell-to-cell contact to support either the proliferation or survival of hematopoietic cells.

Using this dual chambered co-culture system we have determined that NFS-60 proliferate in response to soluble factor(s) produced by primary human osteoblasts and the MG-63 and SaOS-2 osteosarcoma cell lines. Because the osteosarcoma cells also support CD34+ cell proliferation, and they produce a variety of cytokine mRNAs similar to primary human osteoblast, they are good models for osteoblast-hematopoietic proliferative interactions. The basis for the proliferative activity produced by osteoblasts using NFS-60 cells cultured in either recombinant cytokines or neutralizing antibodies has been studied. These data indicate that it is unlikely that the proliferative activity is due to soluble G-CSF, GM-CSF, c-kit ligand, Epo, IL-$1\alpha$, IL-$1\beta$, IL-3, IL-4, IL-5, IL-6, IL-7, IL-11, LIF, LT, M-CSF, MIP-$1\alpha$, PTH, TNF-$\alpha$, TGF-$\beta$, because NFS-60 cells do not grow in these recombinant cytokines. Furthermore, neutralizing antibodies to these cytokines do not inhibit the proliferation of the NFS-60 cells in dual chambered culture with MG-63 or SaOS-2 osteosarcoma cells. NFS-60 cells were plated at 20,000 cells/well in a dual chambered cultures with confluent MG-63 cells for 4 days. On average the cell number increased 5 fold to 100,000 cells/well. Daily addition of neutralizing antibodies at concentrations at or exceeding 5X the anticipated neutralizing doses caused no significant reductions in cell number/well as would be expected if MG-63-derived soluble factors stimulate NFS-60 proliferation. Interestingly, antibody to TGF-$\beta$ stimulated NFS-60 proliferation suggesting that TGF-$\beta$ inhibits NFS-60 proliferation. Control experiments with NFS-60 cells cultured with this antibody alone resulted in little proliferative effect (data not show). Similar data has been obtained from NFS-60\SAOS-2 co-cultures.

$2\times10^4$ NFS-60 cells were seeded into the top chamber of TransWell$^R$ 24 well plates (3 µM pore size) with confluent MG-63 osteosarcoma cells in the bottom chamber. Where indicated neutralizing rabbit polyclonal anti-human cytokine serum (or control) were added daily to test scores to a final concentration of 0.5 µg/ml IL-$1\alpha$, IL-$1\beta$, G-CSF, TNF-$\alpha$), 5 µg/ml (aFGF, LIF), 30 µg/ml (LT, IL-3, IL4, c-kit ligand, MIP-$1\alpha$) (R&D Systems or Genzyme). Murine monoclonal antibodies to GM-CSF, IL-6, TGF-beta or isotype matched control (MOPC21, Sigma) were added daily to the test samples to 30 µg/ml final concentrations. At 4 days absolute NFS-60 cell numbers were determined by manual hemocytometer counting. *Significant difference from control, $p<0.5$.

In vitro we have observed tight adhesion of CD34+ and NFS-60 cells to primary human osteoblasts as well as to MG-63 and SaOS-2 osteosarcoma cells. These observations, along with intriguing anatomic findings where hematopoietic cells are observed in close physical association with osteoblasts suggest unique cellular and molecular adhesive interactions between osteoblasts and hematopoietic cells (Hermans et al., 1989). To explore and evaluate these adhesive events, intercellular adhesion assays are performed.

For these investigations confluent human osteoblast monolayers or hematopoietic cells are incubated with a panel of monoclonal antibodies (or controls) directed at cell surface adhesion molecules (CAMs) that have been reported to mediate adhesive events between stromal cells (or the stromal matrix) and hematopoietic cells. These include, but are not limited to the alpha 4 beta 1, VCAM-1, beta 2 integrins, and Mac-1 and CD45 receptors (Coombe et al., 1994; Simmons et al., 1992; Clezardin et al., 1989; Dittel et al., 1993; and Dowding et al., 1991).

Initially NFS-60 cells are labeled with 100 µCi (Na)$_2^{51}$CrO$_2$/$10^6$ cells for 45 minutes to 1 hour at 37° C., washed once, and then re-incubated for an additional 30 minutes to reduce non-specific background radioactivity. The role of adhesion molecules on osteoblast or NFS-60 cells is investigated by incubation of the cells with saturating antibody concentrations (or control) prior to the co-culture adhesion assay (30 min, 25° C.). NFS-60 cell adhesion to osteoblast's extracellular matrix is addressed by non-enzymatic removal of the osteoblasts with 2 mM EDTA (30 min, 37° C.) prior to the initiation of the adhesion assay.

Labeled NFS-60 cells is applied to osteoblast monolayers or matrix (total volume 200 µ) and incubated for 30 mins at 25° C. Thereafter, the cultures are washed several times, to remove unattached NFS-60 cells, and the adhering NFS-60 cells are quantified against a standard curve by lysis of the cultures in 2% (vol/vol) Triton-100 to determine the radioactivity remaining in each culture (Taichman et al., 1991).

Whether adhesive events between osteoblasts and hematopoietic stem cells can be altered by proinflammatory stimuli is investigated. Specifically, whether osteoblast activation by IL-1 and TNF-$\alpha$ alters the pattern of adhesion between the blood\bone cells is determined. For these experiments, confluent primary human osteoblasts or osteosarcoma cell monolayers are pretreated with IL-$1\beta$ and TNF-$\alpha$ either alone or in combination (10 U/mL and 200 U/mL) for 4–6 hours at 37° C. prior to the addition of labeled hematopoietic cells. These particular inflammatory mediators are used because they enhance hematopoietic cell adhesion to several cell types of mesenchymal origin (Rice et al., 1990) and they alter the phenotypic expression of osteoblastic characteristics (Taichman and Hauschka, 1992).

The direct interaction of hematopoietic cells with stromal cells is important for maintaining hematopoiesis in vitro, although probably not an absolute requirement (Verfaillie et al., 1992). The mechanism(s) whereby adhesion of hematopoietic cells to the bone marrow stroma stimulates proliferation are not completely understood. It is likely that stromal cell-associated or extracellular matrix-associated factors stimulate blood cell proliferation. Recently, the adhesive event itself has been implicated in proliferation due in part to the de novo expression of stromal-derived cytokines following binding. This has been detailed for the induction of IL-7 mRNA in stromal cells following binding of an IL-7-dependent pre-B-lymphoid cell line (Sudo et al., 1989), and NFS-60 cell binding to MC3T3-G2/PA6 stromal cells induces G-CSF protein synthesis (Yoshikubo et al., 1994).

To determine if the binding of hematopoietic cells to osteoblasts induces de novo expression of hematopoietic growth factors. Co-culture assays are performed.

Hematopoietic cells are cultured in the presence or absence of osteoblast or stromal cell layers; either in direct contact with, or separated by a porous membrane (Verfaillie, 1992). Both mRNA and conditioned medium are collected from the cultures and assayed for cytokine expression by RT-PCR and ELISA assay as detailed in *Taichman and Emerson*, 1994. Where mRNA expression is detected without the detection of soluble protein, immunohistochemistry or medium concentration is performed as detailed. (Taichman and Emerson, 1994 and Guba, 1992).

Our data shows that osteoblasts stimulate the limited expansion of hematopoietic progenitors while supporting the expansion and maintenance of the LTC-IC compartment. Our ability to identify these activities has depended upon functional assays where progenitor\stem cells form colonies in cytokine supplemented methyl cellulose. The two assays are LTBMC (Long term bone marrow culture) and the LTC-IC assay (Long-term culture initiating cell assay). In these assays we make the following assumptions: that all colonies are derived from single cells, and that the culture conditions are permissive for each progenitor type to proliferate and differentiate (Eaves and Eaves, 1984). The morphologic effects of osteoblasts on hematopoietic cells were evaluated by Wright-Geimsa staining of hematopoietic cells that recovered from osteoblast co-cultures. After two weeks the majority of the recovered hematopoietic cells maintained an immature morphology.

Finally, to determine whether osteoblasts have a functional role in lineage commitment of $CD34^+$ cells restricted only to the myeloid system, whether osteoblasts participate in lymphopoiesis utilizing a model of lymphocytic differentiation is determined (Ryan et al., 1992). For these investigations $CD34^+$ cells are further depleted of $CD10^+$ B-cell precursors by immunoabsorption (CellPro). The $CD34^+$ $CD10^-$ cells are co-cultured in the presence or absence of osteoblasts and/or the presence or absence of exogenous IL-7. To evaluate lymphocytic lineage commitment, an immunohistochemistry assay based upon the expression of terminal deoxynucleotidyl transferase ($TdT^3$) are performed. $TdT^3$ is a specific marker for immature lymphoid cells undergoing immunoglobulin or T-cell antigen gene rearrangements (Kallenbach et al., 1989). $CD34^+$ cells are seeded onto confluent osteoblasts in eight-well Lab-Tek chamber slides (Nunc, Inc., Naperville, Ill.) for 14 days, in the presence or absence of IL-7. At the completion of the culture period the slides are centrifuged, the medium removed and air dried for 30 mins, and fixed in 100% methanol for 30 mins at 4° C. The slides are air dried again, and then the well chambers removed. The slides are incubated for 60 mins at room temperature with anti-TdT antibody (or control) (Supertecs, Bethesda, Md.) followed by FITC-conjugated goat anti-rabbit Ig. Cultures will be examined for $TdT^+$ cells or colonies under a fluorescence microscope (Ryan et al., 1992).

EXAMPLE 9
PURIFICATION AND CLONING OF NOVEL OSTEOBLAST-DERIVED PROLIFERATIVE HEMATOPOIETIC FACTORS

A cloning system based on expression of osteoblast-derived cDNAs in mammalian cells is utilized. The advantage of this system is that when combined with a sensitive biologic assay, novel factors can be identified independent of prior biochemical purification.

A primary human osteoblast cDNA library is obtained through commercial or collaborative sources. If this proves problematic a cDNA library from poly(A) mRNA obtained from primary human osteocalcin$^+$, c-kit ligand$^-$ osteoblasts by oligo(dT) primed reverse transcription using commercial cDNA synthesis kits (BRL or Amersham). Alternatively, a human cDNA library derived from the MG-63 osteosarcoma can be purchased (Clonetech, Palo Alto Calif.). Data obtained from the osteosarcoma cell line would necessitate verification with primary cells, but the MG-63 cells exhibit similar proliferative activity on $CD34^+$ and NFS-60 in vitro. In addition, ascorbate and $\beta$-glycerol phosphate induced MG-63 cells (and SaOS-2 cells) exhibit similar cytokine profiles to primary human osteoblasts. As such, the MG-63 (and SaOS-2) cell line are invaluable part as an alternative strategy to obtain sufficient quantity or quality of poly(A) mRNA for library construction.

To construct a primary cDNA library, poly(A) mRNA is selected from total RNA by affinity chromatography using oligo(dT)-cellulose (Wood et al., 1977 and Maniatis et al., 1982). Oligo(dT) primed reverse transcription using a commercial kit is employed to synthesize DNA complementary to the osteoblast mRNA. The resulting RNA-DNA hybrids is removed by treatment with NaOH (Maniatis et al., 1982 and Okayma et al., 1982). Second-strand synthesis is completed with T4 DNA polymerase I employing the hairpin loop produced by DNA polymerase I for priming. S1 nucleases treatment for cleavage of single stranded DNA eliminates the hairpin loop. The resulting blunted, double stranded cDNAs are adapted for phagemid insertion using commercial adapters and T4 DNA ligase. To remove unligated adaptors, the adapted cDNAs are passed over a Sepharose CL-4B column (Maniatis et al., 1982). A linearized pBK-RSK phagemid vector is utilized for cloning the cDNAs as it is useful for both procaryotic and eucaryotic expression (Stratagene). The pBK-RSV system allows for cDNAs expressed by SV40 T antigen producing monkey "COS" cells and blue/white color selection in *E. coli* (Kaufman, 1990). The primary human osteoblast cDNA library is screened prior to proceeding with expression experiments for G-CSF and TGF-$\beta$ by Northern hybridization of colony lifts with $^{32}P$ labeled oligonucleotide probes (Owen et al., 1987 and Fisher et al., 1990). Positive clones are removed to control for false positives (G-CSF) and to inhibitory signals produced by TGF-$\beta$, prior to pooling the cDNAs for transfection.

The growth of $CD34^+$ cells in co-culture with osteoblasts but separated by a porous membrane demonstrates that at least some of the osteoblast-derived factors are soluble (TransWell$^R$, Costar). In addition, this culture system provides a sensitive screening tool in which to detect soluble factors expressed in low levels or are short-lived. Use of NFS-60 cells as a model for detecting activities with action on primary human $CD34^+$ cells is justified in that i) NFS-60 cells do not proliferate response to known soluble osteoblast-derived factor(s) including G-CSF and ii) they eliminate the biologic variability observed between bone marrow donors.

For expression cloning the cDNA library is divided into pools of approximately 1000 clones, and cloned cDNAs isolated from each pool are used to transfect monkey COS-1 cells by DEAE-dextran-mediated DNA transfection with chloroquine treatment (Okayma et al., 1982) once G-CSF and TGF-$\beta$ clones have been removed. Supernatants or COS-1/NFS-60 co-cultures (separated from NFS-60 cells via porous membranes) are examined for their ability to stimulate the proliferation of NFS-60 cells. Individual COS-1 cells expressing cDNAs from those positive primary pools are reisolated from chromosomal DNA and rescreened by further subdivisions of the original positive pools (Wood et al., 1977 and Maniatis et al., 1982). This process of subdivision screenings of the transfected COS-1 pools is repeated until all wells are positive.

A biochemical approach for isolating the osteoblast-derived proliferative activities is an alternative strategy. Recently, Gutpa et al. used a biochemical strategy to isolate short-lived factors derived from stromal cells that may require high local concentrations for proliferative activity on hematopoietic cells (Gupta et al., 1993).

We have observed that osteoblast-derived factor(s) stimulate the proliferation of $CD34^+$ and NFS-60 cells in co-culture, but unconcentrated conditioned medium does not. One approach to increase sensitivity of NFS-60 cells to osteoblast conditioned medium is to enhance the sensitivity of the bioassay system by obtaining an subclone with augmented sensitivity to osteoblast-derived proliferative factors. Alternative approaches include i) medium concentration of ostcoblast-conditioned medium, ii) stimulated production of ostcoblast-derived proliferative activities and, iii) the removal of inhibitory factors from osteoblast conditioned medium. All three of these approaches can be utilized together.

Aliquots of conditioned serum-free medium are concentrated 10–20 fold by centrifugation at 1,000 g in a fixed angle JA-17 rotor (Beckman, Palo Alto, Calif.) in Centricon concentrators at 4° C. (Amicon Division of W. R. Grace and Co, Danvers, Mass.) until the desired volume is reached. Stability of the osteoblast-derived hematopoietic activities following the concentration procedure is confirmed by NFS-60 proliferation assays.

We have observed that 25 μg/ml $E.\ coli$ LPS significantly increases the production of a NFS-60 proliferative activity in some, but not by all primary human osteoblasts as well as in the MG-63 and SaOS-2 osteosarcoma. The stimulated activity need not be the same activity basally produced by osteoblasts. However, this activity is not yet fully characterized as NFS-60 cells do not grown in either recombinant bFGF, c-kit ligand, EGF, Epo, GM-CSF, IL-1α, IL-1β, IL-3, IL-4, IL-5, IL-6, IL-7, IL-11, LIF, LT, M-CSF, MIP-1α, PTH, or TNF alone or in combination with G-CSF. Osteoblasts can be stimulated with LPS to enhance the production by osteoblasts of the hematopoietic proliferative activity. If medium from LPS stimulated osteoblasts is to be utilized for biopurification, then removal of soluble G-CSF by methods herein described below is performed as G-CSF levels as high as 21 pg/ml/24 hour/$10^4$ cells of have been observed in our system following LPS stimulation (Taichman and Emerson, 1994).

For hematopoietic cell proliferation to occur in vivo, stimulatory signals must be present in either sufficient quantity or quality to overcome inhibition. Based on our work in the LTC-IC system, LTC-IC maintenance is due at least in part to the production of differentiation/proliferation inhibitory factors.

To determine whether removal of TGF-β would "amplify" osteoblast-derived NFS-60 proliferative activities, we examined whether the proliferation of NFS-60 cells could be enhanced in co-culture with osteoblasts by the inclusion of an neutralizing antibody to TGF-β. Addition of neutralizing TGF-β antibody to NFS-60/MG-63 or SaOS-2 dual chambered cultures stimulated the proliferation of NFS-60 cells above the stimulating activity of the osteosarcoma cells alone.

Thereafter the immune complexes is removed by immunoabsorption with goat anti-murine IgG coupled to CNBr-activated Sepharose by centrifugation (1500 rpm) at 4° C. for 10 min (Pharmacia, Piscataway N.J.) following a 1 hour incubation at 4° C. TGF-β levels will be monitored in osteoblast-conditioned medium following immunoabsorption by ELISA and if necessary the procedure is repeated until below the detection limit of the assay (range: 0.1–4 ng/ml)(Genzyme Diagnostics, Cambridge Mass.).

Thus far, the osteoblast-derived hematopoietic proliferative activity has been detected in direct-contact cultures or when NFS-60 cells are separated by membrane, but not in unconcentrated conditioned medium. Therefore, rapid degradation may be an important component of its biology. Stability and chemical studies are performed which will provide further details on how best to purify and store the activity.

For physical stability studies, 50 μl of osteoblast-conditioned medium obtained after DEAE chromatography is heated to 60° C. for 10 to 30 mins, lyophilized for 24 hours and reconstituted with PBS, or frozen at −20° C. and −70° C. for 24 hours. The samples are then assayed for activity in the NFS-60 proliferation assay.

To determine whether the activity is stable in mild oxidizing agents, 1 mM potassium ferricyanide and 0.5 mM cystine is utilized. Stability in mild reducing agents is evaluated using 10 mM dithiothreitol and 10 mM sodium dithionite. 10 mM phenylglyoxal and 10 mM phenylmethylsulfonyl fluoride (PMSF) is utilized to determine the stability of the factor to arginine modifying agents and serine proteases. Additionally, whether the factor is acid stable or sensitive to trypsin or pronase and whether the activity is heparin binding is determined. Following these treatments the resulting activity is evaluated in the NFS-60 proliferation assay.

To determine whether glycosylation is a significant feature of the factor(s) activity, osteoblast-conditioned medium is passaged through lectin-agarose columns. These will include Con A (carbohydrates specificities; α-D-mannosyl, α-D-glucosyl), peanut agglutinin (β-D-gal(1–3)-D-galNAc, β-D-galactosyl), Ricinus communis agglutinin I (D-galactosyl) and wheat germ agglutinin ((β-N-acetlglucosaminyl)$_2$ sialic acid). Carbohydrate modifications is determined by evaluating the activity in both the filtrate and eluate after passage of the specific carbohydrate buffers through the columns (Vector Laboratories).

Purification of osteoblast-derived hematopoietic proliferative activity is determined as follows. Osteoblast conditioned medium is clarified by centrifugation and passaged through a either a DEAE column or Centricon concentrators at 4° C. (Amicon Division of W. R. Grace and Co, Danvers, Mass.) until desired volume are reached. The concentrated conditioned medium is then applied to a PBS precalibrated Bio-Gel P-60 column. Elution with PBS is performed at a flow rate of 7 ml/hour and fractions of 1.0 ml are collected and stored at −70° C. The column is calibrated with known protein standards including BSA (mol wt 66,000), carbonic anhydrase (29,000) cytochrome C (12,400), aprotinin (6,500). Protein concentration are determined by measuring optical density by colorimetric assay. Column fractions are tested at a dilution of 1:4 by NFS-60 $^3$H-thymidine incorporation. The m.w. of the ostcoblast-derived hematopoietic proliferative activity is estimated from a plot of $K_{av}$ vs log(m.w.).

Alternatively, after filtering the medium through a Millipore filter conditioned medium is concentrated 10 fold and applied to Sephadex G-75 column equilibrated with 150 mmol/L NaCl solutions containing Tris-HCl (pH 7.4), 0.02% sodium azide, and 0.02% Tween-20 for column chromatography. Fractions of 5.0 ml are collected and, 0.05-ml samples are utilized to determine final protein concentrations. For desalting and removal of sodium azide, the protein fractions are dialyzed against PBS containing antibiotics in dialysis membranes of an appropriate pore size. Following dialysis, the retentates are sterile filtered and tested for activity by NFS-60 $^3$H-thyroidine incorporation assay. Several active fractions from Bio-Gel chromatographic runs or Sephadex G-75 columns can be pooled, concentrated and applied to DAEA ion-exchange chromatographic columns equilibrated with Tris-glycine buffer (p.H. 8.2). The NFS-60 proliferative activity is eluted from the DEAE column with a gradient of 0–200 mM sodium acetate in Tris-glycine buffer. A flow rate of 15 ml/hour is utilized with 1.5 ml fraction collection.

Active fractions from DEAE ion-exchange chromatography are pooled, concentrated and prepared for reverse-phase column HPLC (RP-HPLC) purification described in Dewherst et al (Dewherst et al., 1986). Alternatively, sodium dodecyl sulfate polyacrylamide gel electrophoresis (SDS-PAGE) is performed on active DEAE fractions as described by in Taichman et al (1) using standard 20 lane 160×140× 0.75-mM gels. Final protein purification will be achieved by cutting out protein bands of proteins electrotransferred to Immobilon-P membranes (Millipore Corp, Bedford, Mass.). Proteins are visualized by Coomassie blue or Ponceau-S (Bio-Rad).

RP-HPLC fractions containing NFS-60 proliferative activity (verified for proliferative activity on CD34$^+$ cells) or protein bound to Immobilon-P membranes are prepared for sequential Edman degradation analysis in the presence of 1.5 mg polybrene on an Applied Biosystems Incorporated gas phase micro sequencer. NH$_2$-terminal sequence analysis is utilized to design degenerative oligonucleotides for hybridizing and screening an osteoblast cDNA library (Wozney, 1990).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

Aronow, M. A., L. C. Gerstenfeld, T. A. Owne, Tassinari, G. S. Stein, and J. B. Jane. 1990. Factors that promote progressive development of the osteoblast phenotype in cultured fetal rat calvaria cells. *J. Cell. Phys.* 143:213–221.

Ashton, B. A., T. D. Allen, C. R. Howelett, C. C. Eaglesom, A. HAttori, and M. Owen. 1994. Formation of bone mand cartilage by bone marrow stromal cells in diffusion chambers in vivo. *Clinical Orthopedic Related Research* 151:294–307.

Bellows, C. G., J. E. Aubin, J. N. M. Hersche, and M. E. Antosz. 1986. Mineralized nodules formed in vitro from enzymatically released rat calvarial cell populations. *Calcif. Tiss. Intl.* 38:143–154.

Benayahu, D., A. Fried, D. Zipori, and S. Wientroub. 1991. Subpopulations of marrow stromal cells share a variety of osteoblast markers. *Calcif. Tiss. Intl.* 49:202–207.

Benayahu, D., M. Horowitz, D. Zipori, and S. Weintroub. 1992. Hematopoietic functions of marrow-derived osteogenic cells. *Calcif. Tiss. Intl.* 51:195–201.

Berardi, A. C., A. Wang, J. D. Levine, P. Lopez and D. T. Scadden. 1995. Functional Isolation and Characterization of Human Hematopoietic Stem Cells, *Science*, 267: 104–108.

Birch, M. A., A. F. Ginty, C. A. Walsh, W. D. Fraser, J. A. Gallagher, and G. Bilbe. 1993. PCR detection of cytokines in normal human and pagetic osteoblast-like cells. *J. Bone and Min. Res.* 8:1155–1162.

Broxmeyer, H. E., D. E. Williams, E. Lu, S. Cooper, S. L. Anderson, G. S. Beyer, R. Hoffman, and B. Y. Rubin. 1986. The suppressive influences of human tumor necrosis factor on bone marrow hematopoietic progenitor cells from normal donors and patients with leukemia: synergism of tumor necrosis factor and interferon-gamma. *J. Immunol.* 136:4487–4495.

Brühl, P., H. G. Mergenthaler, and Dörmer. 1988. Haematopoietic inductive capacity of irradiated stromal cell layers in human micro long-term bone marrow culture. *Cell Tissue Kenet* 21:411–417.

Caldwell, J., B. O. Polsson, B. Locey, and S. E. Emerson. 1994. Culture perfusion schedules influence the metabolic activity and granulocyte-macrophage colony-stimulating factor production rates of human bone marrow stromal cells. *J. Cell. Phys.* 147:344–353.

Campell, A. D., M. W. Long, and M. S. Wicha. 1987. Haemonectin, a bone marrow adhesion protein specific for cells of granulocyte lineage. *Nature* 329:744–746.

Caruana, G., L. K. Ashman, J. Fujita, and T. J. Gonda. 1993. Responses of the murine myeloid cell line FDC-P1 to soluble and membrane -bound forms of steel factor (SLF). *Exp. Hematol.* 21:761–768.

Celest, A. J., V. Rosen, J. L. Buecker, R. Kris, E. A. Wang, and J. M. Wozney. 1986. Isolation of the human gene for bone gla protein utilizing mouse and rat cDNA clones. *EMBO J.* 5:1885–1890.

Chaudhary, L. R., T. C Spelsberg, and B. L. Riggs. 1992. Production of various cytokines by normal human osteoblast-like cells in response to interleukin-1 beta and tumor necrosis factor-alpha: lack or regulation by 17 beta-estradiol. *Endocrinology*. 130:2528–2534.

Chomcynski, P. and N. Sacchi. 1987. Single step method of RNA isolation by acid guanidinium thiocyanate-phenol-chloroform extraction. *Analytical Biochem.* 162:156–159.

Clezardin, P., H. Jeouishomme, P. Chacassieux, and P. J. Marie. 1989. Thrombospondin is synthesized and secreted by human osteoblasts and osteosarcoma cells. A model to study the different effects of thrombospondin in cell adhesion. *Eur. J. Biochem.* 181:721–726.

Coombe, D. R., S. M. Watt, and C. R. Parish. 1994. Mac-1 (CD11b/CD18) and CD45 mediate the adhesion of hematopoietic progenitor cells to stromal cell elements via recognition of stromal heparan sulfate. *Blood* 84:739–52.

Derynck, R., J. A. Jarret, E. Y. Chen, D. H. Eaton, J. R. Bell, R. K. Assoian, A. B. Roberts, M. B. Sporn, and D. V. Goeddel. 1985. Human transforming growth factor-β complementary DNA sequence and expression in normal and transformed cells. *Nature* 316:701–705.

Dewhirst, F. E., P. P. Stashenko, J. E. Mole, and T. Tsurumachi. 1986. Purification and partial sequence of human osteoclast-activating factor: Identity with interleukin-1β. *J. Immunol.* 135:2562–2568. (Abstr.)

Dexter, T. M. and E. Spooncer. 1987. Growth and differentiation in the hemopoietic system. *Ann. Rev. Cell. Biol.* 3:432–441.

Dexter, T. M. and L. G. Lajtha. 1974. Proliferation of hematopoietic stem cells in vitro. *Br. J. Haematol.* 28:525–530.

Dexter, T. M., L. H. Coutinhot, E. Spooncer, C. M. Heyworth, C. P. Daniel, R. Schirot, J. Chang, and T. D. Allen. 1990. Stromal cells in haemopoiesis. In Molecular Control of Haemopoiesis. Ciba Foundation Symposium, 76 pp.

Dexter, T. M., T. D Allen, and L. G. Lajtha. 1977. Conditions controlling the proliferation of haemopoietic stem cells in vitro. *J. Cell Phys.* 91:335–344.

Dittel, B. N., J. B. McCarthy, E. A. Wayner, and T. W. LeBien. 1993. Regulation of human B-cell prcursor adhesion to bone marrow stromal cells by cytokines that exert opposing effects on the expression of vascular cell adhesion molecule (VCAM-1). *Blood* 81:2272–2282.

Dodds, R. A., K. Mactry, A. Littlewood, and M. Gowen. 1994. Expression of mRNA for IL1$\beta$, IL6 and TGF$\beta$1 in developing human bone and cartilage. *J. Histochem. Cytochem.* 42:733–744.

Doestghman, T. G., H. Elstetter, M. Katz, W. Schmidt, and R. Kemler. 1985. In vitro development of blastoeyst-derived embryonic stem cell lines: formation of visceral yolk sac, blood islands and myocardium. *J. Embrol. Exp. Morph.* 87:27–45.

Dorheim, M. A., M. Sullivan, V. Dandapani, X. Wu, I. Hudson, P. R. Segarini, D. M. Rosen, A. L. Aulthouse, and J. M. Gimble. 1993. Osteoblastic gene expression during adiposegenesis in hematopoietic supporting murine bone marrow stroma cells. *J. Cell Phys.* 154:317–328.

Dowding, C., A. P. Guo, J. Osterholz, M. Siczkowski, J. Goldman, and M. Gordon. 1991. Interferon-alpha overrides the deficient adhesion of chronic myeloid leukemia primative progenitor cells to bone marrow stromal cells. *Blood* 78:499–505.

Duke, r. C. and J. J. Cohn. 1986. IL-2 addiction: withdrawl of growth factor activities a suicide program in dependent T-cells. *Lymphokine Res.* 5:289–299.

Eastman, C. E. and F. W. Ruscetti. 1984. Evaluation of hematopoiesis in long-term bone marrow culture:comparison of species differences. In Long-term bone marrow culture. D. G. Wright and J. S. Greenberger, editors. Allen R Liss., New York. 97–100.

Eaves, A. C. and C. J. Eaves. 1984. Erythropoiesis in culture. In Clinics in Hematology: Cell Culture Techniques. E. A. McCulloch, editor. W. B. Saunders Company., Philadelphia. 393–404.

Eaves, C. J., J. D. Cashman, and A. V. Eaves. 1991. Methodology of long-term culture of human hemopoietic cells. *J. Tiss. Cult. Methods* 13:55–58.

Eaves, C. J., H. J. Sutherland, J. D. Cashman, T. Otsuka, P. M. Lansdorp, P. K. Humphties, A. C. Eaves, and D. E. Hogge. 1991. Regulation of human hematopoietic cells in long-term marrow culture. *Seminars in Hematology* 28:126–131.

Elford, P. R., R. Felex, M. Cecchini, U. Treschel, and H. Fleisch. 1987. Murine osteoblast-like cells and osteogenic cell MC3T3-E1 release a macrophage colony-stimulating activity in culture. *Cal Tissue. Intl.* 41: 151–156.

Emerson, S. G., S. Thomas, J. Ferarra, and J. L. Greenstein. 1989. The developmental regulation of erythropoiesis by hematopoietic growth factors: analysis on populations of BFU-E from bone marrow, peripheral blood, and fetal liver. *Blood* 74:49–55.

Fava, R. A. and D. B. McClure. 1987. Fibronectin-associated transforming growth factor. *J. Cell. Phys.* 131:184–189.

Feinberg, A. P. and B. Vogelstein. 1984. A technique for radiolabeling DNA restriction endonuclease fragments to a high specific activity. *Analytical Biochem.* 137:266–267.

Felix, R., M. G. Cecehini, W. Hofstetter, H. L. Guenther, and H. Fleisch. 1991. Production of granulocyte-macrophage (GM-CSF) and granulocyte colony-stimulating factor (G-CSF) by rat clonal osteoblastic cell population CRP 10/30 and the immortalized cell line IRC10/30-myc 1 stimulated by tumor necrosis factor-$\alpha$. *Endocrinology* 128:661–667.

Felix, R., P. R. Elford, C. Stoeckle, M. Cecchini, U. T. Wetterwalk, H. Fleisch, and B. M. Stadler. 1988. Production of hemopoietic growth factors by bone tissue and bone cells in culture. *J. Bone and Min. Res.* 3:27–36.

Feyen, J. H. M., P. ELford, F. E DiPadova, and U. Trechsel. 1989. Interleukin-6 is produced by bone and modulated by parthyroid hormone. *J. Bone and Min. Res.* 4:633–638.

Fibbe, W. E., J. van Damme, A. Billiau, H. M. Goselink, P. J. Voogt, G. van Eden, P. Ralph, B. W. Altrock, and J. H. F. Falkenbur. 1988. Interleukin 1 induces human marrow stromal cells in long-term culture to produce granulocyte colony-stimulating factor. *Blood* 71:430–435.

Fisher, I. M., O. W. McBride, J. D. Termine, and M. F. Young. 1990. Human bone sialoprotein: deduced protein sequence and chromosomal localization. *J. Biol. Chem.* 265:2347–2351.

Franceschi, R. T. 1992. The role of ascorbic acid in mesenchymal differentiation. *Nutr. Rev.* 50:65–70.

Franceschi, R. T., S. I. Bhanumathi, and C. Yingqi. 1994. Effects of ascorbic acid on collagen matrix fromation and osteoblast differentiation in murine MC3T3-E1 cells. *J. Bone and Min. Res.* 9:843–854.

Friedenstein, A. J. and R. K. Chailakhjan. 1970. The development of fibroblast colonies in monolayer cultures of guinea pig bone marrow and spleen cells. *Cell Tissue Kenet* 3:393–402.

Fuller, K., A. C. Gallagher, and T. J. Chambers. 1991. Osteoclast resorption: stimulating activity is associated with the osteoblast cell surface and/or the extracellular matrix. Biochem. Biophys. Res. Comm. 181:67–73.

Gartner, S. and H. S. Kaplan. 1990. Long-term culture of human bone marrow cells. *Proc. Natl. Acad. Sci. U.S.A.* 77:4756–4769.

Gerstenfeld, L. C., S. D. Chipman, J. Glowacki, and J. B. Lian. 1987. Expression of differentiated function by mineralizing cultures of chicken osteoblasts. *Dev. Bio.* 122:49–60.

Gimble, J. M., J. Hudson, J. Henthorn, X. Hua, and S. A. Burstein. 1991. Regulation of interleukin 6 expression in murine bone marrow stromal cells. *Exper Hematology* 19:1055–1066.

Gordon, M. Y., A. D. Bearpark, and D. Clark. 1988. Extracellular matrix glycoproteins may regulate the local concentrations of different hemopoietic growth factors. In Experimental Hematology Today. S. J. Baum, K. A. Kicke, and E. Lotzova, editors. Springer-Verlag, New York. 31–35.

Gordon, M. Y., A. M. Ford, and M. F. Greaves. 1993. Interactions of hematopoietic progenitor cells with extracellular matrix. In The Hematopoietic Microenvironment: Functional Basis of Blood Cell Development. M. W. Long and M. S. Wicha, editors. John Hopkins University Press, Baltimore. 152–174.

Gordon, M. Y., G. P. Riley, S. M. Watt, and M. F. Greaves. 1987. Compartmentalization of a haematopoietic growth factor (GM-CSF) by glycoseaminoglycans in the bone marrow microenvironment. *Nature* 326:403–405.

Gowen, M., K. Chapman, A. Littlewood, D. Hughes, D. Evans, and R. G. G. Russell. 1990. Production of TNF by human osteoblasts is modulated by other cytokines, but not by osteopetroietic hormones. *Endocrinology.* 126:1250–1255.

Gray, P. W., B. B. Aggarwal, C. V. Beton, T. S. Bringman, W. J. Henzel, J. A. jarrett, D. W. Leung, B. Moffat, P. Ng, L. P. Seversky, M. A. Palladino, and G. E. Neddwin. 1984. Cloning and expression of cDNA for human lymphokine with tumor necrosis activity. *Nature* 312:721–724.

Greenfield E. M., S. A. Gornik, M. C. Horrowitz, H. J. Donahue and S. M. Shaw. 1993. Regulation of cytokine expression in osteoblasts by parathyroid hormone: Rappid stimulation of interleukin-6 and leukemia Inhibitory factor mRNA. J. Bone. Min. Res. 8:1163.

Grey, P. W., D. W. Leung, D. Pennica, E. Ylverton, R. Najarian, C. C. Simonsen, R. Derynek, P. J. Sherwood, D. M. Wallace, S. L. Berger, A. D. Levinson, and D. V. Goeddel. 1982. Expression of human immune interferon cDNA in *E. coli* and monkey cells. *Nature* 295:503–508.

Grigoriadis, A. E., N. J. Heersehe, and J. E. Aubin. 1988. DIfferentiation of muscle, fat, cartilage and bone from progenitor cells present in a bone derived clonal cell population: effect of dexamethasone. *J. Cell. Phys.* 106:2139–2151.

Guba, S. C., C. I. Sartor, L. R. Gottschalk, J. Ye-Hu, T. Mulligan, and S. C. Emerson. 1992. Bone marrow stromal fibroblasts secrete interleukin-6 and granulocyte-macrophage colony-stimulating factor in the absence of inflammatory stimulation: Demonstration by serum-free bioassay, enzyme-linked immunoabsorbant assay and reverse transeriptase polymerase chain reaction. *Blood* 80:1190–1198.

Gupta, P., J. B. McCarthy, and C. M. Veraillie. 1993. Stromal derived, anionie maeromolcule(s) in combination with subliminal amounts of cytokines support the in vitro maintenance and differentiation of primitive human LTC-IC. *Blood* 82:21a.(Abstr.)

Hanazawa, S., S. Amano, K. Nakada, Y. Ohmori, T. Miyoshi, K. Hirose, and S. Kitano. 1987. Biological characterization of interleukin-1-like cytokine produced by bone cells from newborn mouse calvaria. *Calcif. Tiss. Intl.* 41:31–37.

Hanazawa, S., Y. Ohmori, S. Amano, T. Miyoshi, M. Kumegawa, and S. Kitano. 1985. Spontaneous production of interleukin-1-like cytokine from a mouse osteoblastic cell line (MC3T3-E1). *Biochem. Biophys. Res. Comm.* 131:774–779.

Hauschka, P. V. 1989. Growth factor effects in bone. In Bone a treatise: The osteoblast and the osteocyte. B. D. Hull, editor. Telford Press, Caldwell N.J. 103–107.

Hauschka P. V., J. B. Lian, D. C. Cole and C. M. Gundberg. 1989. Osteocalcin and matrix Gla protein: Vitamin K-dependent proteins of bone. Physiologic Reviews. 69:990.

Heard, J. M., S. Fichelson, and B. Varet. 1986. Role of colony stimulating activity in murine long-term bone marrow culures: Evidence for its production and consumption by adherent cells. *Blood* 59:761–767.

Hermans, M. N., H. Hartsuiker, and D. Opstelten. 1989. An in situ study of B-lymphocytopoiesis in rat bone marrow. Topographical arrangement of terminal deoxynucleotidyl transferase-positive cells and pre-B cells. *J. Immunol.* 142:67–73.

Hirano, T., K. Yasukawa, H. Harada, T. Taga, Y. Watanabe, T. Matsuda, S. I. Kashiwamura, K. Nakajima, K. Koyama, A. Iwamatsu, S. Tsunasawa, F. Saldyama, H. Matsui, Y. Takahara, T. Taniguchi, and T. Kisimoto. 1986. Complementary DNA for a novel interleukin (BSF-2) that induces B lymphocytes to produce immunoglobin. Nature 234:73–76.

Horowitz, M. C., D. L. Coleman, J. T. Tyaby, and T. A. Einhorn. 1989. Osteotropic agents induce the differential secretion of granulocyte-macrophage colony-stimulating factor by the osteoblast cell line MC3T3-E1. *J. Bone and Min. Res.* 4:911–921.

Horrowitz, M. C., D. L. Coleman, P. M. Flood, T. S. Kupper, and R. L. Jilka. 1989. Parathyroid hormone and lippopolysacaride induce murine osteoblast-like cells to secrete a cytokine indistinguishable from granulocyte-macrophage stimulating facor. *Clin. Invest.* 83:149–157.

Horowitz, M. C., T. A. Einhorn, W. Philbrick, and R. L. Jilka. 1989. Functional and molecular changes in colony stimulating factor secretion by osteoblasts. *Conn. Tiss. Res.* 20:159–168.

Huang, E., K. Nocka, D. R. Beier, T. Y. Chu, J. Buck, H. M. Lahm, D. Wellner, P. Leder, and P. Besmer. 1990. The hematopoietic growth factor KL is encoded by the Sl locus ans is the ligand of the c-kit receptor, the gene product of the W locus. *Cell* 63:225–233.

Huange, S. and L. W. M. M. Terstappen. 1992. Formation of haematopoietic microenvironment and haematopoietie stem cells from single human bone marrow stem cells. *Nature* 360:745–749.

Ibaraki, K., J. D. Termine, W. Whitson, and M. F. Young. 1992. Bone matrix mRNA expression in differentiating fetal osteoblasts. *J. Bone and Min. Res.* 7:743–754.

Ishimi, Y., C. Miyaura, C. H. Jin, T. Akatsu, E. Abe, Y. Nakamura, A. Yamaguchi, S. Yoskik, T. Matsuda, T. Hirano, T. Kishimo to, and T. Suda. 1990. IL-6 is produced by osteoblasts and induces bone resorption. *J. Immunol.* 145:3297–3303.

Jirillo, E., P. Decandia, M. R. Ribaud, B. Cannuscio, C. De Simone, and S. Antonaci. 1992. Enhancement of polymorphonuclear cell phagocytosis by lipid A-activated monocytes via cell-to-cell contact. A possible role for membrane-associated cytokines. *Immunopharmacol. Immunotoxicol.* 14:343–354.

Johnson, A. and K. Dorshkind. 1986. Stromal cells in myeloid and lymphoid long-term bone marrow cultures can support multiple hemopoietic lineages and modulate their production of hemopoietic growth factors. *Blood* 68:1348–1354.

Kallenbach, S., N. Doyen, M. Fanton d'Andon, and F. Rougeon. 1992. Three lymphoid-specific factors account for all junctional diversity characteristic of somatic assembly of T-cell receptor and immunoglobin genes. *Proc. Natl. Acad. Sci. USA.* 89:2799–2803.

Kaufman, R. J. 1990. Vectors used for expression of mammalian cells. In Methods in Enzymology: Gene Expression Technology. D. V. Goeddel, editor. Academic Press, Inc., New York. 487–511.

Keeling, P. E., L. Rifas, S. A. Harris, D. S. Colvard, T. C. Spelsberg, W. A. Peck, and B. L. Riggs. 1991. Evidence for interleukin-1β production by cultured normal human osteoblast-like cells. *J. Bone and Min. Res.* 6:827–833.

Kincade, P. W., K. Medina, C. E. Petrangeli, S. I. Hayashi, and A. E. Namen. 1991. Stromal cell lines which support lymphocyte growth II. Characteristics of a suppressive subclone. In Mechanisms of lymphocyte activation and immune regulation III. S. Gupta, editor. Plenum Press, New York. 227–234.

Kincade, P. W., P. L. Witte, and K. S. Landreth. 1987. Stromal cell and factor-dependent B lymphopoieisis in culture. *Current Topics in Microbiology and Immunology* 135:1–21.

Kittler, E. and P. J. Quesenberry. 1993. Stromal cells and clinical implications. In The hematopoietic microenvironment: functional basis of blood cell development. M. W. Long and M. S. Wicha, editors. John Hopkins University Press, Baltimore. 49–76.

Kittler, E. L. W., H. McGrath, D. Temeles, R. B. Crittenden, V. K. Kister, and P. J. Quesenberry. 1992. Biologic significance of constitutive and subliminal growth factor production by bone marrow stroma. *Blood* 79:3168–3178.

Kurt-Jones, E. A., D. I Beller, S. B. Mizel, and E. R. Unanue. 1985. Identification of a membrane bound interleukin-1. *Proc. Natl. Acad. Sci. USA.* 82: 1204–1208.

Kurtz, D. T. and C. R. Nicodemus. 1981. Cloning of α2u globin cDNA using a high efficiency technique for the cloning of trace messenger RNAs. *Gene* 13:148–152.

Kyoizumi, S., C. M. Baum, H. Kaneshima, J. M. McCune, E. J. Yee, and R. Namikawa. 1992. Implantation and maintenence of functional human bone marrow in SCID-hu mice. *Blood* 79:1704–1711.

Lee, G., L. R. Ellingworth, S. Gillis, R. Wall, and P. W. Kincade. 1986. Transforming growth factor beta's are potiential regulators of B-lymphopoiesis. *J. Exp. Med.* 166:1290.

Levinson, A. 1990. Exression of heterologous genes in mammalian cells. In Methods In Enzymology: Gene Expression Technology. D. V. Goeddel, editor. Academic Press,Inc., New York. 485–486.

Linkhart, T. A., S. G. Linkhart, D. C. MacCharles, D. L. Long, and D. D. Strong. 1991. Interleukin-6 messenger RNA expression and interleukin-6 protein secretion in cells isolated from normal human bone: regulation by intefieukin-1. *J. Bone and Min. Res.* 6:1285–1294.

Littlewood, A. J., D. E. Hughes, L. A. Aardent, R. G. G. Russell, and M. Gowen. 1990. Cytokines but not osteotropic hormones induce IL-6 release from human osteoblast-like cells in vitro. *Bone* 11:215–216.

Long, M. W., L. J. Williams, and K. G. Mann. 1990. Expression of human bone-related proteins in the hematopoietic microenvironment. *J. Clin. Invest.* 86:1387–1397.

Lord B. I. 1990. The architecture of bone marrow cell populations. Int'l. J. of Cell Cloning 8:317.

Majeska, R. J. and G. A. Rodan. 1988. Culture and activity of osteoblasts and osteoblast-like cells. In Cell and Molecular Biology of Vertebrate Hard Tissues. CIBA Foundation Symposium 136. Wiley, New York. 279–285.

Maniatis, T., E. F. Fritsch, and J. Sambrook. 1982. Molecular Cloning: A Laboratory Manual. Cold Spring Harbor Laboratory, Cold Spring Harbor, N.Y.

March, C. J., B. Mosley, A. Larsen, D. P. Cerretti, G. Braedtice, S. Gillis, S. C. Henney, S. R. Kronheim, K. Grabsetin, P. J. Conlon, T. P. Hopp, and D. Cosman. 1985. Cloning, sequence and expression of two distinct human interleukin-1 complementary cDNA's. *Nature* 315:641–647.

Marie, P. J., M. Hott, J. M. Launay, A. M. Grraulet, and J. Gueris. 1993. In Vitro production of cytokines by bone surface-derived osteoblastic cells in normal and osteoporotic postmenopausa women: Relationship with cell proliferation. *J Clin. Endocrinol. Metab.* 77:824–830.

Marmenout, A., L. Fransen, J. Traverier, J. Van Der Heyden, R. Tizard, E. Kawashima, A. Shaw, M-J. Johnson, D. Semon, Muller, M-R. Ruysschaert, A. Van Vliet, and W. Fiers. 1985. Molecular cloning and expression of human tumor necrosis factor and comparison with mouse tumor necrosis factor. *Eur. J. Biochem.* 152:515–522.

Marusic, A., J. F. Kalinowski, S. Jastrzebski, and J. A. Lorenzo. 1993. Production of leukemia inhibitory factor mRNA and protein by malignant and immortalizod bone cells. *J. Bone and Min. Res.* 8:617–624.

Masatsugu, O., J. S. Greenberger, P. ndlesarea, A. Bassols, and J. Massaugue. 1987. Two forms of transforming growth factor-β distinguished by multipotient haematopoietic progenitor cells. *Nature* 329:539–541.

Mathieu, E. and J. M. Merregaert. 1992. Characterization of the stromal osteogenic cell line MN7: effects of PTH, 1,25(OH)2D3 and 17β-E2 at the mRNA level. *Calcif. Tiss. Intl.* 50:A14.

Mayani, H., L. J. Guilbert, and A. Jamowska-Wieczorek. 1992. Biology of the hemopoietic microenvironment. *Eur. J. Hatmat.* 49:225–233.

Metcalf, D. 1988. The molecular control of blood cells. Harvard University Press, Cambridge Mass. 1 pp.

Miller, S. C. and W. S. Jee. 1987. The bone lining cell: a distinct phenotype? *Calcif. Tiss. Intl.* 41:1–5.

Motoyama, T., T. Hotta, H. Watanabe, T. Kumanishi, T. Ichikawa, and M. Seldguehi. 1993. Differential production of interleukin 6 in human osteosarcoma cell lines and the possible effects on neoplastic bone metabolism. *Virchows Archiv. B. Cell. Pathol.* 63:277–281.

Nagata, S. 1990. Granulocyte colony stimulating factor. In Handbook of experimental pharmacology. M. B. Sporn and A. B. Roberts, editors. Springer-Verlag, Heidelberg.

Nagata, S., M. Tsuchiya, S. Asano, Y. Kaziro, T. Tamazaki, and M. Ono. 1986. Molecular cloning and expression of cDNA for human granulocyte colony-stimulating factor. *Nature* 319:415–418.

Nicola, N. A. 1989. Hematopoietic cell growth factors and their receptors. *Ann. Rev. Biochem.* 58:45–77.

Ohtsuki, T., S. Suzu, N. Nagata, and K. Motoyshi. 1992. A osteoblastic cell line, MG-63, produces two molecular typos of macrophage-colony-stimulating factor. *Biochim. Biophys. Acta.* 1136:297–301.

Ohtsuki, T., S. Suzu, K. Hatake, N. Nagata, Y. Miuri, and K. Motoyoshi. 1993. A proteoglycan form of macrophage colony-stimulating factor that binds to bone-derived collagens and can be extracted from bone matrix. *Biochem. Biophys. Res. Comm.* 190:215–22.

Ohtsuki, T., S. Suzu, N. Nagata, and K. Motoyoshi. 1992. A human osteoblastic cell line, MG-63, produces two molecular typos of macrophage-colony-stimulating factor. *Biochim. Biophys. Acta.* 1136:297–301.

Okayma, H. and P. Berg. 1982. High-efficiency cloning of full length cDNA. *MoL Cell. Biol.* 2:161–170.

Owen, T. A., M. Aronow, V. Shalhoub, L. M. Barone, L. Wilming, M. S. Tassinari, M. B. Kennedy, S. Pockwinse, J. B. Lian, and G. S. Stein. 1990. Progressive development of the rat osteoblast phenotype in vitro: reciprocal relationships in expression of genes associated with osteoblast proliferation and differentiation during formation of the bone extracellular matrix. *J. Cell. Phys.* 143:420–430.

Pirruccello, S. J., J. D. Jackson, M. S. Lang, J. DeBoer, S. Mann, D. Crouse, W. P. Vaughan, K. A. Dicke, and J. G. Sharp. 1992. OML-AML-I: A leukemic myeloid cell line with CD34+ progenitor and CD15+ spontaneous differentiating cell compartments. *Blood* 80:1026–1032.

Ponte, P., S. Y. Ng, J. Engel, P. Gunning, and L. Kedes. 1984. Evolutionary conservation in the untranslated regions of actin mRNAs:DNA sequence of a human beta-actin cDNA. *Nucleic Acids Res.* 12:1687–1696.

Poo, W. J., L. Conrad, and C. A. Janeway. 1988. Receptor-directed focusing of lymphokine release by helper T-cells. *Nature* 332:278–380.

Quesenberry, P. J. 1989. Stromal cells in long-term bone marrow cultures. In Handbook of the hematopoietic microenvironment. M Tavassoli, editor. Humana Press, Clifton, N.J. 253–285.

Ralston, S. H. 1994. Analysis of gene expression in human bone biopsies by polymerase chain reaction: Evidence for enhanced cytokine expression in postmenopausal osteoporosis. *J. Bone and Min. Res.* 9:883–890.

Reddi, A. H. and K. E. Huettner. 1981. Vascular invasion of cartilage: Correlation of morphology with lysozyme, glycosaminoglycans, protease, and protease-inhibitory activity during endocondral bone development. *Dev. Bio.* 832:217–223.

Reddi, A. H. and C. H. Huggins. 1972. Biochemical sequences in the transformation of normal fibroblasts in adolescent rats. *Proc. Natl. Acad. Sci. USA.* 69:1601–1604.

Rice, G. E., J. M. Munro, and M. P. Bevilacqua. 1990. Inducible cell adhesion molecule 110 (INCAM-110) is an endothelial receptor for lymphocytes: A CD11/CD18-independent adhesion mechanism. *J. Exp. Med.* 171:1369–1374.

Roberts, R., J. Gallagher, E. Spooncer, T. D. Allen, F. Bloomfield, and T. M. Dexter. 1988. Heparan sulfate bound growth factors: a mechanism for stromal cell mediated haemopoiesis. *Nature* 332:376–378.

Robey, P. G., M. F. Young, K. C. Flanders, N. S. Roche, P. Kondaiah, A. H. Reddi, J. D. Termine, M. D. Sporn, and A. B. Roberts. 1987. Osteoblasts synthesize and respond to transforming growth factor-type β (TGF-β) in vitro. *J. Cell. Biol.* 105:457–463.

Robey, P. G. and J. D. Termine. 1985. Human bone cells in vitro. *Calcif. Tiss. Intl.* 37:453–460.

Ryan, D. H., B. L. Nuccie, and C. N. Abboud. 1992. Inhibition of human bone marrow lymphoid progenitor colonies by antibodies to VLA integrins. *J. Immunol.* 149:3759–3764.

Schwartz, R. M., S. E. Emerson, M. F. Clark, and B. O. Polson. 1991. In vitro myelopoiesis stimulated by rappid medium exchange and supplementation with hematopoietic growth factors. *Blood* 78:3155–3166.

Schwartz, R. M., B. O. Polson, and S. E. Emerson. 1991. Rappid medium perfusion rate siginificantly increases the productivity and longevity of human marrow cultures. *P.N.A.S. USA.* 88:6760–6764.

Shinner, D. and G. A. Rodan. 1993. Relationships and interactions between bone and bone marrow. In The hematopoietic microenvironment: Functional basis of blood cell development. M. W. Long and M. S. Wicha, editors. John Hopkins University Press, 70–109.

Shirafuji, N., S. Asano, S. Matsuda K. Watari, F. Takaku, and S. Nagata. 1989. A new biodassay for humanulocyte colony-stimulating factor (hG-CSF) using murine myeloblastic NFS-60 cells as targets and estimation of its levels in sera from normal healthy persons and patients with infectous and hematological disorders. *Exp. Hematol.* 17:116–119.

Simmons, P. J., B. Masinovsky, B. M. Longenecker, R. Berenson, B. Torok-Storb, and W. M. Gallatin. 1992. Vascular cell adhesion molecule-1 expressed by bone marrow stromal cells mediates the binding of hematopoietic progenitor cells. *Blood* 80:388–395.

Simons, P. J., A. Zannettino, S. Gronthos, and D. Leavesley. 1994. Potential adhesion mechanisms for localization of hematopoietic progenitors to bone marrow stroma. *Leukemia and Lymphoma* 12:353–63.

Singer, J. W. 1994. Recombinant human interleukin-6 (rhIL-6) stimulates anchorage independent growth of marrow stroma cell (MSC) colonies which can be expanded as adherent lines that costitutively produce high levels of colony stimulating activity (CSA). *Blood* 74:Suppl 1:13A.(Abstr.).

Singer J. W., J. L. Slack, M. B. Lilly and D. F. Andrews. 1993. Marrow stromal cells, response to cytokines and control of gene expression. The Hematopoietic Microenvironment: Functional basis of blood cell development. M. W. Long and M. S. Wicha, editors. John Hopkins University Press. 127–151.

Srour, E. F., J. E. Brandt, R. A. Briddell, S. Grigsby, T. Leemhuis, and R. Hoffman. 1993. Long-term generation and expansion of human hematopoietic progenitor cells in vitro. *Blood* 81:661–669.

Stein, J., G. V. Bortizllo, and C. V. Rettenmier. 1990. Direct stimulation of cells expressing receptors for macrophage colony stinulating factor (CSF-1) by a plasma membrane bound precursor of human CSF-1. *Blood* 76:1308–1314.

Sudo, T., M. Ito, Y. Ogawa, M. Iizuka, H. Kodama, T. Kunisada, S-I. Hayashi, M. Ogawa, K. Sakai, S. Nishikawa, and S-I. Nishikawa. 1989. Interleukin-7 production and function in stromal cell-dependent B cell development. *J. Exp. Med.* 170:333–338.

Sutherland, H. J., P Lansdorp, M., D. H. Henkelman, A. V. Eaves, and C. F. Eaves. 1990. Functional characterization of individual human hematopoietic stem cells cultured at limiting dilution on supportive marrow stromal layers. *P.N.A.S. USA.* 87:3584–3588.

Taichman, R. S. and S. G. Emerson. 1994. Human osteoblasts support hematopoiesis through the production of granulocyte colony-stimulating factor. *J. Exp. Med.* 179:1677–1682.

Taichman, R. S., T. Torigoe, S. Tanaka, T. Miyashita, and J. C. Reed. 1992. Gene transfer investigations of p56-LCK function in IL-2-dependent T-cell lines: implications for mechanisms of IL-2-signal transduction. *Cytokine* 4:441–453.

Taichman, R. S., I. Merida, T. Torigo, G. Gulton, and J. C. Reed. 1993. Evidence that protein tyrosine p56-Lck regulates the activity of phosphatidylinositol-3'-kinase in interleukin-2-dependent T-cells. *J. Biol. Chem.* 268:20031–20036.

Taichman, R. S. and P. V. Hauschka. 1992. Effects of interleukin-1β and tumor necrosis factor-α on osteoblastic expression of osteocalcin and mineralized extracellular matrix in vitro. *Inflammation* 16:587–601.

Taichman, D. B., M. I. Cybulsky, I. Djaffar, B. M. Longenecker, J. Teixido, G. E. Rice, A. Aruffo, and M. P. Bevilacqua. 1991. Tumor cell surface alpha 4 beta 1 integrin mediates adhesion to vascular endotheium: demonstration of an interaction with the N-terminal domains of INCAM-110/VCAM-1. *Cell Regulation* 2:347–355.

Tavassoli, M. and C. L. Hardy. 1993. The molecular mechanism for recognition of intravenously transplanted progenitor cells. In The Hematopoietic Microenvironment: The Functional Basis of Blood Cell Development. M. W. Long and M. S. Wicha, editors. John Hopkins University Press, Baltimore. 217–231.

Trentin, J. J. 1989. Hematopoietic micorenvironments: Historical perspectives, status, projections. In Handbook of the Hemataopoietic Microenvironment. M. Tavassoli, editor. Humana Press, Clifton N.J.

Theis, R. S., M. Bauduy, B. A. Ashton, L. Kurtzerg, J. M. Wozney, and V. Rosen. 1992. Recombinant human bone morphogenic protein-2 induces osteogenic differentiation in W-20-17 stromal cells. *Endocrinology* 130:1318–1324.

Toksoz, D., K. M. Zsebo, K. A. Smith, S. Hu, D. Brankow, S. V. Suggs, F. H. Martin, and D. A. Williams. 1992. Support of human hematopoiesis in long-term bone marrow cultures by murine stromal cells selectively expressing the membrane-bound and secreted forms of the human homolog of the steel gene product, stem cell factor. *Proc. Natl. Acad. Sci. USA.* 89:7350–7354.

Torigoe, T., J. A. Millan, K. W. H. Chan, R. Taichman, A. A. Brian, and J. C. Reed. 1994. Protein tyrosine kinase p56-Lck regulates lymphocyte function-associated 1 adhesion molecule expression, granule exocytosis, and cytolytic effector function in a cloned T cell. *J. Exp. Med.* 180:1115–1127.

Urist, M. R., R. DeLange, and G. A. M. Feinerman. 1983. Bone cell differentiation and growth factors. *Science* 220:680–686.

Verfaillie, C. M. 1992. Direct contact between human primitive hematopoietic progenitors and bone marrow stroma is not required for long-term in vitro hematopoiesis. *Blood* 79:2821–2826.

Weir, E. C., K. L. Insogna, and M. C. Horowitz. 1989. Osteoblast-like cells secrete granulocyte-macrophage colony-stimulating factor in response to parathyroid hormone and lippopolysaccaride. *Endocrinology.* 124:899–904.

Whitlock, C. A. and O. N. Witte. 1982. Long-term culture of B lymphocytes and their precursors from murine bone marrow. *Proc. Natl. Acad. Sci. USA.* 79:3608–3612.

Wong, G. C., J. S. Witek, P. A. Temple, K. M. Wilkens, A. C. Leary, D. P. Luxenberg, S. S. Jones, E. L. Brown, R. M. Kay, and E. C. Orr. 1985. Human GM-CSF: Molecular cloning of the complementary DNA and purification of the natural and recombinant proteins. *Science* 228:810–815.

Wood, T. G. and J. B. Lingerel. 1977. Purification of biologically active globin mRNA using cDNA-cellulose affinity chromatography. *J. Biol. Chem.* 252:457–463.

Wozney, J. M. 1990. Using purified protein to clone its gene. In Methods In Enzymology: Guild to Protein Purification. M. P. Deutscher, editor. Academic Press, INC., New York. 738–750.

Wutier, R. E. and T. C. Register. 1988. Role of alkaline phosphatase a polyfunctional enzyme in mineralizing tissues. In The Chemistry and Biology of Mineralized Tissues. W. T. Butler, editor. EBESCO Media, Birmingham. 112–121.

Wyllie, A. H., R. G. Morris, A. L. Smith, and D. Dunlop. 1984. Chromatin cleavage in apoptosis: association with condensed chromatin, morphology and dependence on macromolecular synthesis. *J. Pathol.* 142:67–77.

Yang, T. C., A. B. Ciarletta, P. A. Temple, M. P. Chung, S. Kovacic, J. S. Witek-Giannotti, A. C. Leary, R. Kritz, R. E. Donahue, G. G. Wong, and S. C. Clark. 1986. Human IL-3 (Multi-CSF): Identification by expression cloning of a novel hematopoietic growth factor related to murine IL-3. *Cell* 47:3–10.

Yoshikubo, T., K. Ozawa, K., Takahashi, M. Nishikawa, N. Horiuchi, A. Tojo, K. Tani, H. Kodama, and S. Asano. 1994. Adhesion of NFS-60 myeloid leukemia cells to MC3T3-G2/PA6 stromal cells induces granulocyte colony-stimulating factor production. *Blood* 84:415–420.

Zheng, M. H., D. J. Wood, S. Wysocki, J. M. Papadimitriou, and E. A. Wang. 1994. Recombinant human bone morphogenic protein-2 enhances expression of interleukin-6 and transforming growth factor-beta 1 genes in normal human osteoblast-like cells. *J. Cell. Phys.* 159:76–82.

Zipori, D. 1992. Regulation of hemopoiesis by cytokines that restrict options for growth and differentiation. *Cancer Cells* 2:205–211.

Zipori, D. and F. Lee. 1988. Introduction of interleukin-3 gene into stromal cells from the bone marrow alters hematopoietic differentiation but does not modify stem cell renewal. *Blood* 77:586–599.

Zipori, D., M. Tamir, J. Toledo, and T. Oren. 1986. Differentiation stage and lineage-specific inhibitor from the stroma of mouse bone marrow that restricts lymphoma cell growth. *Proceedings National Academy Science USA* 83:4547–4551.

Dexter, T. M., T. D. Allen, and L. G. Lajtha. 1977. Conditions for proliferation of hematopoietic stem cells in vitro. *J. Cell. Phys.* 91:335–344.

Dexter, T. M. and L. G. Lajatha. 1974. Proliferation of haematopoietic stem cells in vitro. *Br. J. Haematol.* 28:525–530.

Gowen, M., K. Chapman, A. Littlewood, D. Hughes, D. Evans, and R. G. G. Russell. 1990. Production of TNF by human osteoblasts is modulated by other cytokines but not by osteopetrotic hormones. *Endocrinology* 126:1250–1255.

Ryan, D. H., B. L. Nuccie, and C. N. Abboud. 1992. Inhibition of human bone marrow lymphoid progenitor colonies by antibodies to VLA integrins. *J. Immunol.* 149:3759–3764.

Shirafuji N., S. Asano, M. Matsuda, K. Watari, F. Takaku, S. Nagata. 1989. A new bioassay for human granulocyte colony-stimulating factor (hG-CSF) using murine myeloblastic NFS-60 cells as targets and estimation of its levels in sera from normal healthy persons and patients with infectious and hematological disease. Exp. Hematology. 17:116.

Toksoz, D., K. M. Zsebo, K. A. Smith, S. Hu, S. V. Suggs, F. N. Martin, and D. A. Williams. 1992. Support of human hematopoiesis in long-term bone marrow cultures by murine stromal cells selectively expressing the membrane-bound and secreted froms of the human homolog of the steel gene product, stem cell factor. *Proc. Natl. Acad. Sci. USA.* 89:7350–7354.

---

What is claimed:

1. A process for propagating and maintaining the immature morphology of mammalian hematopoietic cells, said immature morphology being defined as $CD34^+$, $HLA-DR^+$, $Thy-1^+$ and $Lin^-$, the process comprising the steps of:
   (a) obtaining an enriched population of mammalian hematopoietic cells having the immature morphology of $CD34^+$, $HLA-DR^+$, $Thy-1^+$ and $Lin^-$;
   (b) co-culturing said enriched population of mammalian hematopoietic cells in the presence of osteoblast cells for a time period of between about 2 weeks and about 8 weeks; and
   (c) collecting mammalian hematopoietic cells having the immature morphology of $CD34^+$, $HLA-DR^+$, $Thy-1^+$ and $Lin^-$ maintained by the process of step (b).

2. The process of claim 1, wherein said enriched population of mammalian hematopoietic cells is obtained from mammalian bone marrow cells, umbilical cord cells, liver cells, spleen cells or peripheral blood stem cells.

3. The process of claim 2, wherein said enriched population of mammalian hematopoietic cells is obtained from mammalian bone marrow cells.

4. The process of claim 3, wherein said mammalian bone marrow cells are human bone marrow cells.

5. The process of claim 1, wherein said enriched population of mammalian hematopoietic cells is obtained by equilibrium-density centrifugation of mammalian cells to provide cells with a density of between about 1.010 and about 1.090 grams/cm$^3$.

6. The process of claim 5, wherein said enriched population of mammalian hematopoietic cells is obtained by equilibrium-density centrifugation of mammalian cells to provide cells with a density of between about 1.040 and about 1.090 grams/cm$^3$.

7. The process of claim 6, wherein said enriched population of mammalian hematopoietic cells is obtained by equilibrium-density centrifugation of mammalian cells to provide cells with a density of between about 1.040 and about 1.080 grams/cm$^3$.

8. The process of claim 7, wherein said enriched population of mammalian hematopoietic cells is obtained by equilibrium-density centrifugation of mammalian cells to provide cells with a density of between about 1.070 and about 1.080 grams/cm$^3$.

9. The process of claim 1, wherein said enriched population of mammalian hematopoietic cells is obtained by exposing mammalian cells to an adherent surface and removing adherent cells.

10. The process of claim 9, wherein said adherent surface is tissue culture plastic or tissue culture glass.

11. The process of claim 1, wherein said enriched population of mammalian hematopoietic cells is obtained by exposing mammalian cells to a first hematopoietic cell antibody immunoreactive with a hematopoietic cell antigen and removing mammalian cells that do not immunoreact with the hematopoietic cell antibody.

12. The process of claim 11, wherein said first hematopoietic cell antibody is an anti-CD34 antibody.

13. The process of claim 11, wherein said first hematopoietic cell antibody is an anti-HLA-DR antibody.

14. The process of claim 11, wherein said first hematopoietic cell antibody is an anti-Thy-1 antibody.

15. The process of claim 11, wherein said enriched population of mammalian hematopoietic cells is obtained by exposing mammalian cells to a first and second hematopoietic cell antibody immunoreactive with a first and second hematopoietic cell antigen; and removing mammalian cells that do not immunoreact with the first and second hematopoietic cell antibodies.

16. The process of claim 11, wherein said enriched population of mammalian hematopoietic cells is obtained by exposing mammalian cells to a first hematopoietic cell antibody immunoreactive with a hematopoietic cell antigen; and by isolating the mammalian hematopoietic cells that bind to said first hematopoietic cell antibody using a secondary antibody that is immunoreactive with said first hematopoietic cell antibody.

17. The process of claim 1, wherein said enriched population of mammalian hematopoietic cells is obtained from a population of mammalian cells by stimulating the growth of cells that have already differentiated into more mature blood cells with a cytokine and by exposing said cells that have already differentiated into more mature blood cells to an antimetabolite that kills the more mature blood cells.

18. The process of claim 17, wherein said cytokine is c-Kit ligand or interleukin-3.

19. The process of claim 17, wherein said antimetabolite is 5-fluorouracil or 4-hydroxycyclophosphamide.

20. The process of claim 1, wherein said enriched population of mammalian hematopoietic cells is obtained by equilibrium-density centrifugation of mammalian cells to provide cells with a density of between about 1.010 and about 1.090 grams/cm$^3$; by exposing said mammalian cells to an adherent surface to remove adherent cells; and by exposing said mammalian cells to a hematopoietic cell antibody immunoreactive with a hematopoietic cell antigen and removing mammalian cells which do not immunoreact with the hematopoietic cell antibody.

21. The process of claim 20, wherein said enriched population of mammalian hematopoietic cells is obtained by equilibrium-density centrifugation of mammalian cells to provide cells with a density of between about 1.010 and about 1.090 grams/cm$^3$; by exposing said mammalian cells to an adherent surface to remove adherent cells; and by exposing said mammalian cells to an anti-CD34 antibody immunoreactive with the hematopoietic cell antigen CD34 and removing mammalian cells that do not immunoreact with the anti-CD34 antibody.

22. The process of claim 1, wherein said osteoblast cells produce a cytokine.

23. The process of claim 22, wherein said osteoblast cells produce the cytokine granulocyte colony stimulating factor, granulocyte macrophage colony stimulating factor, or stem cell factor.

24. The process of claim 1, wherein co-culturing said enriched population of mammalian hematopoietic cells in the presence of osteoblast cells comprises the steps of:
  (a) culturing the osteoblasts in a calcium containing media to provide an osteoblast culture; and
  (b) adding said enriched population of mammalian hematopoietic cells to the osteoblast culture to co-culture the enriched population of mammalian hematopoietic cells in the presence of osteoblast cells.

25. The process of claim 24, wherein said enriched population of mammalian hematopoietic cells is added to a confluent osteoblast culture.

26. The process of claim 26, wherein said enriched population of mammalian hematopoietic cells is co-cultured in the presence of osteoblast cells for a time period of between about 2 weeks and about 6 weeks.

27. The process of claim 26, wherein said enriched population of mammalian hematopoietic cells is co-cultured in the presence of osteoblast cells for a time period of between about 2 weeks and about 4 weeks.

28. The process of claim 1, further comprising the steps of separating the co-cultured mammalian hematopoietic cells from the osteoblast cells and collecting the co-cultured hematopoietic cells.

29. The process of claim 1, wherein co-culturing said enriched population of mammalian hematopoietic cells in the presence of osteoblast cells comprises the steps of:
  (a) culturing osteoblasts in a calcium-containing media to provide a confluent osteoblast culture that produces the cytokine granulocyte colony stimulating factor, granulocyte macrophage colony stimulating factor or stem cell factor;
  (b) adding the enriched population of mammalian hematopoietic cells to the cytokine-immunoreact producing confluent osteoblast culture to co-culture the enriched population of mammalian hematopoietic cells in the presence of confluent, cytokine-producing osteoblast cells; and
  (c) separating the co-cultured mammalian hematopoietic cells from the confluent, cytokine-producing osteoblast cells and collecting the co-cultured hematopoietic cells.

30. A process for propagating mammalian hematopoietic cells that maintain an immature morphology defined as $CD34^+$, $HLA\text{-}DR^+$, $Thy\text{-}1^+$ and $Lin^-$, the process comprising the steps of:
  (a) obtaining an enriched population of mammalian hematopoietic cells having the immature morphology of $CD34^+$, $HLA\text{-}DR^+$, $Thy\text{-}1^+$ and $Lin^-$ by a method comprising the enrichment processes of:
    (i) subjecting mammalian bone marrow cells to equilibrium-density centrifugation to provide centrifuged cells with a density of between about 1.010 and about 1.090 grams/cm$^3$; and
    (ii) exposing the centrifuged cells to an anti-CD34 antibody immunoreactive with the hematopoietic cell antigen CD34, and removing cells that do not immunoreact with the anti-CD34 antibody;
  (b) co-culturing said enriched population of mammalian hematopoietic cells in the presence of osteoblast cells for a time period of between about 2 weeks and about 8 weeks; and
  (c) collecting mammalian hematopoietic cells having the immature morphology of $CD34^+$, $HLA\text{-}DR^+$, $Thy\text{-}1^+$ and $Lin^-$ maintained by the process of step (b).

31. The process of claim 30, wherein the equilibrium-density centrifugation enrichment process of step (a) is conducted prior to the anti-CD34 antibody immunoreactivity enrichment process of step (a).

32. The process of claim 30, wherein the anti-CD34 antibody immunoreactivity enrichment process of step (a) is conducted prior to the equilibrium-density centrifugation enrichment process of step (a).

33. The process of claim 30, wherein the step (a) comprises, in sequence, the enrichment processes of:
  (i) subjecting mammalian bone marrow cells to a first equilibrium-density centrifugation to provide first centrifuged cells with a density of between about 1.040 and about 1.080 grams/cm$^3$; and
  (ii) exposing the first centrifuged cells to an anti-CD34 antibody immunoreactive with the hematopoietic cell antigen CD34, and removing cells that do not immunoreact with the anti-CD34 antibody to provide centrifuged, immunoreactive cells; and
  (iii) subjecting the centrifuged, immunoreactive cells to a second equilibrium-density centrifugation to provide second centrifuged cells with a density of between about 1.040 and about 1.080 grams/cm$^3$.

34. The process of claim 30, wherein the co-culturing of step (b) is conducted for a period of between about 2 weeks and about 6 weeks.

35. The process of claim 30, wherein the co-culturing of step (b) is conducted for a period of between about 2 weeks and about 4 weeks.

36. A process for propagating mammalian hematopoietic cells that maintain the immature morphology defined as $CD34^+$, $HLA\text{-}DR^+$, $Thy\text{-}1^+$ and $Lin^-$, the process comprising the steps of:
  (a) obtaining an enriched population of mammalian hematopoietic cells having the immature morphology of $CD34^+$, $HLA\text{-}DR^+$, $Thy\text{-}1^+$ and $Lin^-$ by a method comprising the enrichment processes of:
    (i) subjecting mammalian bone marrow cells to equilibrium-density centrifugation to provide centrifuged cells with a density of between about 1.040 and about 1.080 grams/cm$^3$;
    (ii) exposing the centrifuged cells to an adherent surface, and removing adherent cells to provide centrifuged, non-adherent cells; and
    (iii) exposing the centrifuged, non-adherent cells to an anti-CD34 antibody immunoreactive with the hematopoietic cell antigen CD34, and removing cells that do not immunoreact with the anti-CD34 antibody;
  (b) co-culturing said enriched population of mammalian hematopoietic cells in the presence of osteoblast cells for a time period of between about 2 weeks and about 8 weeks; and
  (c) collecting mammalian hematopoietic cells having the immature morphology of $CD34^+$, $HLA\text{-}DR^+$, $Thy\text{-}1^+$ and $Lin^-$ maintained by the process of step (b).

37. A purified population of mammalian hematopoietic cells that maintain the immature morphology of $CD34^+$, $HLA\text{-}DR^+$, $Thy\text{-}1^+$ and $Lin^-$ for a time period of between about 2 weeks and about 8 weeks, said hematopoietic cells having a density of between about 1.010 gm/cm$^3$ and about 1.090 gm/cm$^3$ and being prepared by a process comprising the steps of:

(a) obtaining an enriched population of mammalian hematopoietic cells having the immature morphology of $CD34^+$, $HLA-DR^+$, $Thy-1^+$ and $Lin^-$;

(b) co-culturing said enriched population of mammalian hematopoietic cells in the presence of osteoblast cells for a time period of between about 2 weeks and about 8 weeks; and (c) obtaining therefrom a population of mammalian hematopoietic cells that have maintained the immature morphology of $CD34^+$, $HLA-DR^+$, $Thy-1^+$ and $Lin^-$ and have a density of between about 1.010 gm/cm$^3$ and about 1.090 gm/cm$^3$.

38. The purified population of mammalian hematopoietic cells of claim 37 which, upon maturity, differentiate to provide an erythrocyte, platelet, monocyte, neutrophil, basophil, eosinophil, lymphocyte, or a mast cell.

39. A process of infusing mammalian hematopoietic cells into a human in need of hematopoietic cells, the process comprising the steps of:

(a) obtaining a purified population of mammalian hematopoietic cells of immature morphology, as defined in claim 37; and (b) introducing said mammalian hematopoietic cells into said human.

40. The process of claim 39, wherein the mammalian hematopoietic cells are introduced into said human by injecting the mammalian hematopoietic cells into the bloodstream.

41. The process of claim 39, wherein the mammalian hematopoietic cells are introduced into said human by introducing the mammalian hematopoietic cells into the marrow cavity of a bone.

* * * * *

UNITED STATES PATENT AND TRADEMARK OFFICE
CERTIFICATE OF CORRECTION

PATENT NO. : 5,733,541

DATED : March 31, 1998

INVENTOR(S) : Taichman *et al.*

It is certified that error appears in the above-identified patent and that said Letters Patent is hereby corrected as shown below:

In claim 26, column 69, line 18, delete "of claim 26, wherein" and insert -- of claim 1, wherein -- therefor.

In claim 29 (b), column 69, line 39, delete "cytokine-immunoreact producing" and insert -- cytokine-producing -- therefor.

Signed and Sealed this

Seventh Day of July, 1998

Attest:

BRUCE LEHMAN

*Attesting Officer*     *Commissioner of Patents and Trademarks*